US011097951B2

(12) United States Patent
Kowal et al.

(10) Patent No.: US 11,097,951 B2
(45) Date of Patent: Aug. 24, 2021

(54) PRODUCTION OF CARBON-BASED OXIDE AND REDUCED CARBON-BASED OXIDE ON A LARGE SCALE

(71) Applicant: The Regents of the University of California, Oakland, CA (US)

(72) Inventors: Matthew Kowal, Los Angeles, CA (US); Richard B. Kaner, Pacific Palisades, CA (US); Maher F. El-Kady, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 299 days.

(21) Appl. No.: 15/630,758

(22) Filed: Jun. 22, 2017

(65) Prior Publication Data

US 2017/0369323 A1    Dec. 28, 2017

Related U.S. Application Data

(60) Provisional application No. 62/354,439, filed on Jun. 24, 2016, provisional application No. 62/510,021, filed on May 23, 2017.

(51) Int. Cl.
*C01B 32/23* (2017.01)
*C01B 32/198* (2017.01)
(Continued)

(52) U.S. Cl.
CPC .............. *C01B 32/23* (2017.08); *C01B 7/00* (2013.01); *C01B 32/192* (2017.08);
(Continued)

(58) Field of Classification Search
CPC ....... C01B 32/23; C01B 7/00; C01B 2204/28; C01B 32/198; C01B 32/192;
(Continued)

(56) References Cited

U.S. PATENT DOCUMENTS 2,800,616 A   7/1957  Becker
3,288,641 A   11/1966 Rightmire
(Continued)

FOREIGN PATENT DOCUMENTS

CN   100372035 C    2/2008
CN   101723310 A    6/2010
(Continued)

OTHER PUBLICATIONS

Kang, et al., Hidden Second Oxidation Step of Hummers Method, Chem. Mater. 2016; 28: 756-764 (hereinafter "Kang at_") with Supporting Information, pp. S1-S17 ("Kang SI at_") (published Dec. 31, 2015) (Year: 2015).*
(Continued)

*Primary Examiner* — Daniel C. McCracken
(74) *Attorney, Agent, or Firm* — Withrow & Terranova, P.L.L.C.

(57) ABSTRACT

Provided herein are carbon-based oxide (CBO) materials and reduced carbon-based oxide (rCBO) materials, fabrication processes, and devices with improved performance and a high throughput. In some embodiments, the present disclosure provides materials and methods for synthesizing CBO and rCBO materials. Such methods avoid the shortcomings of current synthesizing methods to facilitate facile, high-throughput production of CBO and rCBO materials.

24 Claims, 14 Drawing Sheets

(51) Int. Cl.
    *C01B 32/192* (2017.01)
    *C01B 7/00* (2006.01)
    *C07D 307/62* (2006.01)
(52) U.S. Cl.
    CPC .......... *C01B 32/198* (2017.08); *C07D 307/62* (2013.01); *C01B 2204/28* (2013.01)
(58) Field of Classification Search
    CPC .............. C01B 32/182; C01B 2204/00; C01B 2204/02; C01B 2204/04; C01B 2204/06; C01B 2204/065; C01B 2204/20; C01B 2204/22; C01B 2204/24; C01B 2204/26; C01B 2204/30; C01B 2204/32; C07D 307/62
    See application file for complete search history.

(56) References Cited

U.S. PATENT DOCUMENTS

| | | |
|---|---|---|
| 3,536,963 A | 10/1970 | Boos |
| 3,652,902 A | 3/1972 | Hart et al. |
| 4,327,157 A | 4/1982 | Himy et al. |
| 4,645,713 A | 2/1987 | Shioya et al. |
| 5,143,709 A | 9/1992 | Labes |
| 5,225,296 A | 7/1993 | Ohsawa et al. |
| 5,442,197 A | 8/1995 | Andrieu et al. |
| 5,744,258 A | 4/1998 | Bai et al. |
| 6,043,630 A | 3/2000 | Koenck et al. |
| 6,117,585 A | 9/2000 | Anani et al. |
| 6,252,762 B1 | 6/2001 | Amatucci |
| 6,356,433 B1 | 3/2002 | Shi et al. |
| 6,451,074 B2 | 9/2002 | Bluvstein et al. |
| 6,510,043 B1 | 1/2003 | Shiue et al. |
| 6,522,522 B2 | 2/2003 | Yu et al. |
| 6,982,517 B2 | 1/2006 | Reineke et al. |
| 7,623,340 B1 | 11/2009 | Song et al. |
| 7,833,663 B2 | 11/2010 | Phillips et al. |
| 7,875,219 B2 | 1/2011 | Zhamu et al. |
| 8,315,039 B2 | 11/2012 | Zhamu et al. |
| 8,503,161 B1 | 8/2013 | Chang et al. |
| 8,593,714 B2 | 11/2013 | Agrawal et al. |
| 8,753,772 B2 | 6/2014 | Liu et al. |
| 8,771,630 B2 | 7/2014 | Wu et al. |
| 8,828,608 B2 | 9/2014 | Sun et al. |
| 8,906,495 B2 | 12/2014 | Chen |
| 8,951,675 B2 | 2/2015 | Bhardwaj et al. |
| 9,118,078 B2 | 8/2015 | Huang et al. |
| 9,295,537 B2 | 3/2016 | Cao |
| 9,437,372 B1 | 9/2016 | Zhamu et al. |
| 2002/0136881 A1 | 9/2002 | Yanagisawa et al. |
| 2002/0160257 A1 | 10/2002 | Lee et al. |
| 2003/0013012 A1 | 1/2003 | Ahn et al. |
| 2003/0169560 A1 | 9/2003 | Welsch et al. |
| 2004/0090736 A1 | 5/2004 | Bendale et al. |
| 2004/0099641 A1 | 5/2004 | Mathieu et al. |
| 2004/0131889 A1 | 7/2004 | Leddy et al. |
| 2005/0153130 A1 | 7/2005 | Long et al. |
| 2006/0121342 A1 | 6/2006 | Sano et al. |
| 2006/0201801 A1 | 9/2006 | Bartlett et al. |
| 2006/0207878 A1 | 9/2006 | Myung et al. |
| 2006/0269834 A1 | 11/2006 | West et al. |
| 2007/0172739 A1 | 7/2007 | Visco et al. |
| 2007/0204447 A1 | 9/2007 | Bernstein et al. |
| 2008/0090141 A1 | 4/2008 | Meitav et al. |
| 2008/0158778 A1 | 7/2008 | Lipka et al. |
| 2008/0180883 A1 | 7/2008 | Palusinski et al. |
| 2008/0199737 A1 | 8/2008 | Kazaryan et al. |
| 2008/0220293 A1 | 9/2008 | Marmaropoulos et al. |
| 2008/0265219 A1 | 10/2008 | Whitehead et al. |
| 2009/0059474 A1 | 3/2009 | Zhamu et al. |
| 2009/0117467 A1 | 5/2009 | Zhamu et al. |
| 2009/0289328 A1 | 11/2009 | Tanioku |
| 2009/0290287 A1 | 11/2009 | Lipka et al. |
| 2010/0159346 A1 | 6/2010 | Hinago et al. |
| 2010/0159366 A1 | 6/2010 | Shao-Horn et al. |
| 2010/0195269 A1 | 8/2010 | Kim et al. |
| 2010/0203362 A1 | 8/2010 | Lam et al. |
| 2010/0221508 A1 | 9/2010 | Huang et al. |
| 2010/0226066 A1 | 9/2010 | Sweeney et al. |
| 2010/0237296 A1 | 9/2010 | Gilje |
| 2010/0266964 A1 | 10/2010 | Gilje |
| 2010/0273051 A1 | 10/2010 | Choi et al. |
| 2010/0317790 A1 | 12/2010 | Jang et al. |
| 2011/0026189 A1 | 2/2011 | Wei et al. |
| 2011/0111283 A1 | 5/2011 | Rust et al. |
| 2011/0111299 A1 | 5/2011 | Liu et al. |
| 2011/0143101 A1 | 6/2011 | Sandhu |
| 2011/0159372 A1 | 6/2011 | Zhamu et al. |
| 2011/0163274 A1 | 7/2011 | Plee et al. |
| 2011/0163699 A1 | 7/2011 | Elder et al. |
| 2011/0183180 A1 | 7/2011 | Yu et al. |
| 2011/0227000 A1 | 9/2011 | Ruoff et al. |
| 2011/0242730 A1 | 10/2011 | Zhou et al. |
| 2011/0256454 A1 | 10/2011 | Nicolas et al. |
| 2011/0318257 A1 | 12/2011 | Sokolov et al. |
| 2012/0111730 A1 | 5/2012 | Choi et al. |
| 2012/0129736 A1* | 5/2012 | Tour ...................... B82Y 30/00 507/140 |
| 2012/0134072 A1 | 5/2012 | Bae et al. |
| 2012/0145234 A1 | 6/2012 | Roy-Mayhew et al. |
| 2012/0300364 A1 | 11/2012 | Cai et al. |
| 2012/0313591 A1 | 12/2012 | Brambilla et al. |
| 2013/0026409 A1 | 1/2013 | Baker et al. |
| 2013/0048949 A1 | 2/2013 | Xia et al. |
| 2013/0056346 A1 | 3/2013 | Sundara et al. |
| 2013/0056703 A1 | 3/2013 | Elian et al. |
| 2013/0100581 A1 | 4/2013 | Jung et al. |
| 2013/0155578 A1 | 6/2013 | Tsai et al. |
| 2013/0161570 A1 | 6/2013 | Hwang et al. |
| 2013/0168611 A1 | 7/2013 | Zhou et al. |
| 2013/0171502 A1 | 7/2013 | Chen et al. |
| 2013/0180912 A1 | 7/2013 | Li |
| 2013/0182373 A1 | 7/2013 | Yu et al. |
| 2013/0189602 A1 | 7/2013 | Lahiri et al. |
| 2013/0217289 A1 | 8/2013 | Nayfeh et al. |
| 2013/0230747 A1 | 9/2013 | Patolsky et al. |
| 2013/0264041 A1 | 10/2013 | Zhamu et al. |
| 2013/0266858 A1 | 10/2013 | Inoue et al. |
| 2013/0280601 A1 | 10/2013 | Geramita et al. |
| 2013/0314844 A1 | 11/2013 | Chen et al. |
| 2013/0330617 A1 | 12/2013 | Yoshimura et al. |
| 2014/0029161 A1 | 1/2014 | Beidaghi et al. |
| 2014/0030590 A1 | 1/2014 | Wang et al. |
| 2014/0045058 A1 | 2/2014 | Zhao et al. |
| 2014/0050947 A1 | 2/2014 | Donnelly |
| 2014/0065447 A1 | 3/2014 | Liu et al. |
| 2014/0099558 A1 | 4/2014 | Itakura et al. |
| 2014/0118883 A1 | 5/2014 | Xie |
| 2014/0120453 A1 | 5/2014 | Ajayan et al. |
| 2014/0134503 A1 | 5/2014 | Lockett et al. |
| 2014/0154164 A1 | 6/2014 | Chen et al. |
| 2014/0170476 A1 | 6/2014 | Tan et al. |
| 2014/0178763 A1 | 6/2014 | Mettan |
| 2014/0205841 A1 | 7/2014 | Qiu et al. |
| 2014/0255776 A1 | 9/2014 | Song et al. |
| 2014/0255785 A1 | 9/2014 | Do et al. |
| 2014/0287308 A1 | 9/2014 | Okada et al. |
| 2014/0313636 A1 | 10/2014 | Tour et al. |
| 2014/0323596 A1 | 10/2014 | Jeong et al. |
| 2015/0050554 A1 | 2/2015 | Fukumine et al. |
| 2015/0098167 A1 | 4/2015 | El-Kady et al. |
| 2015/0103469 A1 | 4/2015 | Lee et al. |
| 2015/0111449 A1 | 4/2015 | Cruz-Silva et al. |
| 2015/0218002 A1 | 8/2015 | Plomb et al. |
| 2015/0218003 A1 | 8/2015 | Zhamu et al. |
| 2015/0235776 A1 | 8/2015 | Miller |
| 2015/0259212 A1 | 9/2015 | Li et al. |
| 2015/0287544 A1 | 10/2015 | Irazoqui et al. |
| 2015/0311504 A1 | 10/2015 | Hong et al. |
| 2015/0332868 A1 | 11/2015 | Jung et al. |
| 2015/0340171 A1 | 11/2015 | Li et al. |
| 2015/0364738 A1 | 12/2015 | Pope et al. |
| 2015/0364755 A1 | 12/2015 | Liu et al. |

(56) References Cited

U.S. PATENT DOCUMENTS

| | | |
|---|---|---|
| 2016/0035498 A1 | 2/2016 | Honma et al. |
| 2016/0055983 A1 | 2/2016 | Kurungot et al. |
| 2016/0077074 A1 | 3/2016 | Strong et al. |
| 2016/0099116 A1 | 4/2016 | Yang |
| 2016/0133396 A1 | 5/2016 | Hsieh |
| 2016/0148759 A1 | 5/2016 | El-Kady et al. |
| 2017/0062821 A1 | 3/2017 | Tour et al. |
| 2017/0240424 A1 | 8/2017 | Roberts et al. |
| 2017/0338472 A1 | 11/2017 | Zhamu et al. |
| 2018/0366280 A1 | 12/2018 | Hwang et al. |
| 2019/0006675 A1 | 1/2019 | Cheng et al. |
| 2019/0088420 A1 | 3/2019 | Tour et al. |
| 2019/0237752 A1 | 8/2019 | El-Kady et al. |

FOREIGN PATENT DOCUMENTS

| | | |
|---|---|---|
| CN | 101894679 A | 11/2010 |
| CN | 102187413 A | 9/2011 |
| CN | 102509632 A | 6/2012 |
| CN | 102543483 A | 7/2012 |
| CN | 102923698 A | 2/2013 |
| CN | 103208373 A | 7/2013 |
| CN | 103723715 A | 4/2014 |
| CN | 203839212 U | 9/2014 |
| CN | 104299794 A | 1/2015 |
| CN | 104355306 A | 2/2015 |
| CN | 104617300 A | 5/2015 |
| CN | 104637694 A | 5/2015 |
| CN | 105062074 A | 11/2015 |
| CO | 2011026153 A | 2/2011 |
| EP | 1262579 A2 | 12/2002 |
| EP | 1843362 A1 | 10/2007 |
| EP | 2088637 A2 | 8/2009 |
| EP | 2933229 A1 | 10/2015 |
| JP | S61010855 A | 1/1986 |
| JP | S62287568 A | 12/1987 |
| JP | 2002063894 A | 2/2002 |
| JP | 2003217575 A | 7/2003 |
| JP | 2004039491 A | 2/2004 |
| JP | 2004055541 A | 2/2004 |
| JP | 2004063297 A | 2/2004 |
| JP | 2005138204 A | 6/2005 |
| JP | 2005199267 A | 7/2005 |
| JP | 20050317902 A | 11/2005 |
| JP | 2006252902 A | 9/2006 |
| JP | 2007160151 A | 6/2007 |
| JP | 2009525247 A | 7/2009 |
| JP | 2010222245 A | 10/2010 |
| JP | 2011165680 A | 8/2011 |
| JP | 2012169576 A | 9/2012 |
| JP | 2012188484 A | 10/2012 |
| JP | 2013534686 A | 9/2013 |
| JP | 2014053209 A | 3/2014 |
| JP | 2014201492 A | 10/2014 |
| JP | 2015218085 A | 12/2015 |
| KR | 20070083691 A | 8/2007 |
| KR | 20080064967 A | 7/2008 |
| KR | 10-2009-0107498 A | 10/2009 |
| KR | 1020100114827 B1 | 4/2017 |
| WO | 9632618 A1 | 10/1996 |
| WO | 2011019431 A1 | 2/2011 |
| WO | 2011021982 A1 | 2/2011 |
| WO | 2011072213 A2 | 6/2011 |
| WO | 2012006657 A1 | 1/2012 |
| WO | 2012087698 A1 | 6/2012 |
| WO | 2012138302 A1 | 10/2012 |
| WO | 2013024727 A1 | 2/2013 |
| WO | 2013040636 A1 | 3/2013 |
| WO | 2013066474 A2 | 5/2013 |
| WO | 2013070989 A1 | 5/2013 |
| WO | 2013128082 A1 | 9/2013 |
| WO | 2013155276 A1 | 10/2013 |
| WO | 2014011722 A2 | 1/2014 |
| WO | 2014028978 A1 | 2/2014 |
| WO | 2014062133 A1 | 4/2014 |
| WO | 2014072877 A2 | 5/2014 |
| WO | 2014134663 A1 | 9/2014 |
| WO | 2014181763 A1 | 11/2014 |
| WO | 2015023974 A1 | 2/2015 |
| WO | 2015069332 A1 | 5/2015 |
| WO | 2015153895 A1 | 10/2015 |
| WO | 2015195700 A1 | 12/2015 |
| WO | 2016094551 A1 | 6/2016 |
| WO | 2016133571 A2 | 8/2016 |
| WO | 2016190225 A1 | 12/2016 |
| WO | 2017035462 A1 | 3/2017 |

OTHER PUBLICATIONS

Sulfuric Acid—Density, accessed online at https://www.engineeringtoolbox.com/indsulfuric-acid-density-d_2163.html on Apr. 10, 2020 (Year: 2020).*
Kang, et al., Hidden Second Oxidation Step of Hummers Method, Chem. Mater. 2016; 28: 756-764 (Year: 2016).*
Fernandez-Merino, et al., Vitamin C Is an Ideal Substitute for Hydrazine in the Reduction of Graphene Oxide Suspensions, J. Phys. Chem. C. 2010; 114: 6426-6432 (Year: 2010).*
Sulfuric Acid—Density, accessed online at https://www.engineeringtoolbox.com/indsulfuric-acid-density-d_2163.html on Apr. 10, 2020, to show a state of fact (Year: 2020).*
Examination Report for European Patent Application No. 12874989.2, dated Mar. 5, 2019, 5 pages.
Non-Final Office Action for U.S. Appl. No. 16/029,930, dated Jan. 14, 2019, 8 pages.
Office Action for Canadian Patent Application No. 2,866,250, dated Jan. 11, 2019, 3 pages.
Corrected Notice of Allowability for U.S. Appl. No. 15/319,286, dated Jan. 18, 2019, 5 pages.
Notice of Reasons for Rejection for Japanese Patent Application No. 2016-573846, dated Feb. 26, 2019, 8 pages.
Search Report for Japanese Patent Application No. 2016-573846, dated Feb. 28, 2019, 44 pages.
Non-Final Office Action for U.S. Appl. No. 14/945,232, dated Jan. 9, 2019, 7 pages.
Examination Report No. 1 for Australian Patent Application No. 2015349949, dated Mar. 8, 2019, 4 pages.
Final Office Action for U.S. Appl. No. 15/382,871, dated Jan. 25, 2019, 16 pages.
Final Office Action for U.S. Appl. No. 15/410,404, dated Feb. 21, 2019, 9 pages.
Final Office Action for U.S. Appl. No. 15/472,409, dated Jan. 18, 2019, 12 pages.
International Preliminary Report on Patentability for International Patent Application No. PCT/US2017/048883, dated Mar. 14, 2019, 7 pages.
International Preliminary Report on Patentability for International Patent Application No. PCT/US2017/038992, dated Jan. 3, 2019, 10 pages.
Non-Final Office Action for U.S. Appl. No. 15/427,210, dated Feb. 28, 2019, 17 pages.
Gao, Yu et al., "High power supercapcitor electrodes based on flexible TiC-CDC nano-felts," Journal of Power Sources, vol. 201, Issue 1, Mar. 2012, Elsevier B.V., pp. 368-375.
Gao, Lijun et al., "Power Enhancement of an Actively Controlled Battery/Ultracapacitor Hybrid," IEEE Transactions on Power Electronics, vol. 20, Issue 1, Jan. 2005, IEEE, pp. 236-243.
Ghasemi, S. et al., "Enhancement of electron transfer kinetics on a polyaniline-modified electrode in the presence of anionic dopants," Journal of Solid State Electrochemistry, vol. 12, Issue 3, Jul. 28, 2007, Springer-Verlag, pp. 259-268.
Ghidiu, Michael et al., "Conductive two-dimensional titanium carbide 'clay' with high volumetric capacitance," Nature, vol. 516, Dec. 4, 2014, Macmillan Publishers Limited, pp. 78-81.
Gilje, Scott et al., "A Chemical Route to Graphene for Device Applications," Nano Letters, vol. 7, Issue 11, Oct. 18, 2007, American Chemical Society, pp. 3394-3398.
Gilje, Scott et al., "Photothermal Deoxygenation of Graphene Oxide for Patterning and Distributed Ignition Applications," Advanced

(56) References Cited

OTHER PUBLICATIONS

Materials, vol. 22, Issue 3, Oct. 26, 2009, Wiley-VCH Verlag GmbH & Co. KGaA, Weinheim, Germany, pp. 419-423.
Glavin, M.E et al, "A Stand-alone Photovoltaic Supercapacitor Battery Hybrid Energy Storage System," Proceedings of the 13th International Power Electronics and Motion Control Conference (EPE-PEMC), Sep. 1-3, 2008, Poznań, Poland, IEEE, pp. 1688-1695.
Gogotsi, Y. et al., "True Performance Metrics in Electrochemical Energy Storage," Science Magazine, vol. 334, Issue 6058, Nov. 18, 2011, 4 pages.
Gracia, J. et al., "Corrugated layered heptazine-based carbon nitride: the lowest energy modifications of $C_3N_4$ ground state," Journal of Materials Chemistry, vol. 19, 2009, pp. 3013-3019.
Griffiths, Katie et al., "Laser-scribed graphene presents an opportunity to print a new generation of disposable electrochemical sensors," Nanoscale, vol. 6, Sep. 22, 2014, The Royal Society of Chemistry, pp. 13613-13622.
Guardia, L. et al., "UV light exposure of aqueous graphene oxide suspensions to promote their direct reduction, formation of graphene-metal nanoparticle hybrids and dye degradation," Carbon, vol. 50, Issue 3, Oct. 12, 2011, Elsevier Ltd., pp. 1014-1024.
Guerrero-Contreras, Jesus et al., "Graphene oxide powders with different oxidation degree, prepared by synthesis variations of the Hummers method," Materials Chemistry and Physics, vol. 153, Mar. 1, 2015, Elsevier B.V., pp. 1-12.
Günes, Fethullah et al., "Layer-by-Layer Doping of Few-Layer Graphene Film," ACS Nano, vol. 4, Issue 8, Jul. 27, 2010, American Chemical Society, pp. 4595-4600.
He, Xinping et al., "A new nanocomposite: Carbon cloth based polyaniline for an electrochemical supercapacitor," Electrochimica Acta, vol. 111, Aug. 17, 2013, Elsevier Ltd., pp. 210-215.
Hu, Liangbing et al., "Symmetrical $MnO_2$-Carbon Nanotube-Textile Nanostructures for Wearable Pseudocapacitors with High Mass Loading," ACS Nano, vol. 5, Issue 11, Sep. 16, 2011, American Chemical Society, pp. 8904-8913.
Huang, Yi et al., "An Overview of the Applications of Graphene-Based Materials in Supercapacitors," Small, vol. 8, Issue 12, Jun. 25, 2012, Wiley-VCH Verlag GmbH & Co. KGaA, Weinheim, pp. 1-30.
Huang, Ming et al., "Self-Assembly of Mesoporous Nanotubes Assembled from Interwoven Ultrathin Birnessite-type $MnO_2$ Nanosheets for Asymmetric Supercapacitors," Scientific Reports, vol. 4, Issue 3878, Jan. 27, 2014, ww.nature.com/scientificreports, pp. 1-8.
Hwang, Jee Y. et al., "Direct preparation and processing of graphene/$RuO_2$ nanocomposite electrodes for high-performance capacitive energy storage," Nano Energy, vol. 18, Sep. 25, 2015, Elsevier B.V., pp. 57-70.
Jana, Milan et al., "Non-covalent functionalization of reduced graphene oxide using sulfanilic acid azocromotrop and its application as a supercapacitor electrode material," Journal of Materials Chemistry A, vol. 3, Issue 14, Feb. 24, 2015, The Royal Society of Chemistry, pp. 7323-7331.
Ji, Junyi et al., "Nanoporous $Ni(OH)_2$ Thin Film on 3D Ultrathin-Graphite Foam for Asymmetric Supercapacitor," ACS Nano, vol. 7, Issue 7, Jun. 11, 2013, American Chemical Society, pp. 6237-6243.
Jimbo, "Transistors," Sparkfun, https://learn.sparkfun.com/tutorials/transistors/extending-the-water-analogy/, accessed Dec. 14, 2015, SparkFun Electronics, 3 pages.
Jin, H. Y. et al., "Controllable functionalized carbon fabric for high-performance all-carbon-based supercapacitors," RSC Advances, vol. 4, Issue 62, Jul. 15, 2014, The Royal Society of Chemistry, pp. 33022-33028.
Kang, Yu Jin et al., "All-solid-state flexible supercapacitors based on papers coated with carbon nanotubes and ionic-liquid-based gel electrolytes," Nanotechnology, vol. 23, Issue 6, Jan. 17, 2012, IOP Publishing Ltd, pp. 1-6.
Khaligh, Alireza et al., "Battery, Ultracapacitor, Fuel Cell, and Hybrid Energy Storage Systems for Electric, Hybrid Electric, Fuel Cell, and Plug-In Hybrid Electric Vehicles: State of the Art," IEEE Transactions on Vehicular Technology, vol. 59, Issue 6, Jul. 2010, IEEE, pp. 2806-2814.
Khomenko, V. et al., "Optimisation of an asymmetric manganese oxide/activated carbon capacitor working at 2 V in aqueous medium," Journal of Power Sources, vol. 153, Issue 1, Mar. 14, 2005, Elsevier B.V., pp. 183-190.
Kiani, Mohammad Ali et al., "Fabrication of High Power $LiNi0.5Mn1.5O4$ Battery Cathodes by Nanostructuring of Electrode Materials," RSC Advances, vol. 5, Issue 62, May 26, 2015, The Royal Society of Chemistry, pp. 1-6.
Kiani, M.A. et al., "Size effect investigation on battery performance: Comparison between micro- and nano-particles of $3-Ni(OH)_2$ as nickel battery cathode material," Journal of Power Sources, vol. 195, Issue 17, Apr. 2, 2010, Elsevier B.V., pp. 5794-5800.
Kiani, M.A. et al., "Synthesis of Nano- and Micro-Particles of $LiMn_2O_4$: Electrochemical Investigation and Assessment as a Cathode in Li Battery," International Journal of Electrochemical Science, vol. 6, Issue 7, Jul. 1, 2011, ESG, pp. 2581-2595.
Kovtyukhova, Nina, I. et al., "Layer-by-Layer Assembly of Ultrathin Composite Films from Micron-Sized Graphite Oxide Sheets and Polycations," Kovtyukhova, et al, Chemistry of Materials, vol. 11, Issue 3, Jan. 28, 1999, American Chemical Society, pp. 771-778.
Lam, L.T. et al., "Development of ultra-battery for hybrid-electric vehicle applications," Journal of Power Sources, vol. 158, Issue 2, May 2, 2006, Elsevier B.V., pp. 1140-1148.
Lang, Xingyou et al., "Nanoporous metal/oxide hybrid electrodes for electrochemical supercapacitors," Nature Nanotechnology, vol. 6, Apr. 2011, Macmillan Publishers Limited, pp. 232-236.
Lee, Kyu Hyung et al., "Large scale production of highly conductive reduced graphene oxide sheets by a solvent-free low temperature reduction," Carbon, vol. 69, Dec. 16, 2013, Elsevier Ltd., pp. 327-335.
Lee, Kyoung, G. et al, "Sonochemical-assisted synthesis of 3D graphene/nanoparticle foams and their application in supercapacitor," Ultrasonics Sonochemistry, vol. 22, May 2, 2014, Elsevier B.V., pp. 422-428.
Lee, Seung Woo et al., "Carbon Nanotube/Manganese Oxide Ultrathin Film Electrodes for Electrochemical Capacitors," ACS Nano, vol. 4, Issue 7, Jun. 16, 2010, American Chemical Society, pp. 3889-3896.
Lei, Zhibin et al., "Platelet CMK-5 as an Excellent Mesoporous Carbon to Enhance the Pseudocapacitance of Polyaniline," ACS Applied Materials & Interfaces, vol. 5, Issue 15, Jul. 12, 2013, American Chemical Society, pp. 7501-7508.
Li, Dan et al., "Processable aqueous dispersions of graphene nanosheets," Nature Nanotechnology, vol. 3, -Feb. 2008, Nature Publishing Group, pp. 101-105.
Li, Lei et al., "Nanocomposite of Polyaniline Nanorods Grown on Graphene Nanoribbons for Highly Capacitive Pseudocapacitors," ACS Applied Materials and Interfaces, vol. 5, Issue 14, Jun. 21, 2013, American Chemical Society, 6 pages.
Li, Peixu et al., "Core-Double-Shell, Carbon Nanotube@Polypyrrole@$MnO_2$ Sponge as Freestanding, Compressible Supercapacitor Electrode," ACS Applied Materials and Interfaces, vol. 6, Issue 7, Mar. 12, 2014, American chemical Society, pp. 5228-5234.
Li, Qi et al., "Design and Synthesis of $MnO_2$/Mn/$MnO_2$ Sandwich-Structured Nanotube Arrays with High Supercapacitive Performance for Electrochemical Energy Storage," Nano Letters, vol. 12, Issue 7, Jun. 25, 2012, American Chemical Society, pp. 3803-3807.
Li, Yingzhi et al., "Oriented Arrays of Polyaniline Nanorods Grown on Graphite Nanosheets for an Electrochemical Supercapacitor," Langmuir, vol. 29, Issue 1, Dec. 3, 2012, American Chemical Society, 8 pages.
Li, Zhe-Fei et al., "Fabrication of high-surface-area graphene/polyaniline nanocomposites and their application in supercapacitors," ACS Applied Materials & Interfaces, vol. 5, Issue 7, Mar. 12, 2013, American Chemical Society, pp. 1-25.
Lin, Jian et al., "3-Dimensional Graphene Carbon Nanotube Carpet-Based Microsupercapacitors with High Electrochemical Performance," Nano Letters, vol. 13, Issue 1, Dec. 13, 2012, American Chemical Society, pp. 72-78.

(56) References Cited

OTHER PUBLICATIONS

Linden, David et al., "Handbook of Batteries," McGraw-Hill Handbooks, Third Edition, 2010, New York, The McGraw-Hill Companies, Inc., 1,454 pages.
Liu, Wenwen et al., "Novel and high-performance asymmetric micro-supercapacitors based on graphene quantum dots and polyaniline nanofibers," Nanoscale, vol. 5, Apr. 24, 2013, The Royal Society of Chemistry, pp. 6053-6062.
Liu, Wen-Wen et al., "Superior Micro-Supercapacitors Based on Graphene Quantum Dots," Advanced Functional Materials, vol. 23, Issue 33, Mar. 26, 2013, Wiley-VCH Verlag GmbH & Co. KGaA, Weinheim, pp. 4111-4122.
Liu, Yongfeng et al., "Advanced hydrogen storage alloys for Ni/MH rechargeable batteries," Journal of Materials Chemistry, vol. 21, Issue 11, Dec. 15, 2010, The Royal Society of Chemistry, pp. 4743-4755.
Long, Jeffrey W. et al., "Asymmetric electrochemical capacitors—Stretching the limits of aqueous electrolytes," MRS Bulletin, vol. 36, Jul. 2011, Materials Research Society, pp. 513-522.
Lu, Xihong et al., "Stabilized TiN Nanowire Arrays for High-Performance and Flexible Supercapacitors," Nano Letters, vol. 12, Issue 10, Sep. 4, 2012, American Chemical Society, 6 pages.
Lukatskaya, Maria R. et al., "Cation Intercalation and High Volumetric Capacitance of Two-Dimensional Titanium Carbide," Science, vol. 341, Issue 6153, Sep. 27, 2013, American Association for the Advancement of Science, pp. 1502-1505.
Lukic, Srdjam, M. et al., "Power Management of an Ultracapacitor/Battery Hybrid Energy Storage System in an HEV," IEEE Vehicle Power and Propulsion Conference (VPPC), Sep. 6-8, 2006, IEEE, 6 pages.
Invitation to Pay Additional Fees for International Patent Application No. PCT/US2017/048883, dated Sep. 29, 2017, 2 pages.
Wang, Xu et al., "Manganese Oxide Micro-Supercapacitors with Ultra-high Areal Capacitance," Electronic Supplementary Material (ESI) for Nanoscale, vol. 5, Mar. 21, 2013, The Royal Society of Chemistry, 6 pages.
Wang, Xuebin et al., "Three-dimensional strutted graphene grown by substrate-free sugar blowing for high-power-density supercapacitors," Nature Communications, vol. 4, Issue 2905, Dec. 16, 2013, Macmillan Publishers Limited, pp. 1-8.
Wassei, Jonathan K. et al., "Oh the Places You'll Go with Graphene", Accounts of Chemical Research, Dec. 20, 2012, Vers. 9, 11 pages.
Weng, Zhe et al., "Graphene-Cellulose Paper Flexible Supercapacitors," Advanced Energy Materials, vol. 1, Issue 5, Aug. 10, 2011, Wiley-VCH Verlag GmbH & Co., pp. 917-922.
Wu, Zhong-Shuai et al., "Graphene Anchored with $Co_3O_4$ Nanoparticles as Anode of Lithium Ion Batteries with Enhanced Reversible Capacity and Cyclic Performance," ACS Nano, vol. 4, Issue 6, May 10, 2010, American Chemical Society, pp. 3187-3194.
Xie, Guoxin, "Direct Electrochemical Synthesis of Reduced Graphene Oxide (rGO)/Copper Composite Films and Their Electrical/Electroactive Properties," Applied Materials & Interfaces, vol. 6, Issue 10, May 1, 2014, American Chemical Society, pp. 7444-7455.
Xu, Bin et al., "Sustainable nitrogen-doped porous carbon with high surface areas prepared from gelatin for supercapacitors," Journal of Materials Chemistry, vol. 22, Issue 36, Jul. 25, 2012, The Royal Society of Chemistry, pp. 19088-19093.
Xu, Jing et al., "Flexible Asymmetric Supercapacitors Based upon $Co_9S_8$ Nanorod//$Co_3O_4$@$RuO_2$ Nanosheet Arrays on Carbon Cloth," ACS Nano, vol. 7, Issue 6, May 6, 2013, American Chemical Society, pp. 5453-5462.
Xu, Yuxi et al., "Flexible Solid-State Supercapacitors Based on Three-Dimensional Graphene Hydrogel Films," ACS Nano, vol. 7, Issue 5, Apr. 4, 2013, American Chemical Society, 8 pages.
Xu, Zhanwei et al., "Electrochemical Supercapacitor Electrodes from Sponge-like Graphene Nanoarchitectures with Ultrahigh Power Density," The Journal of Physical Chemistry Letters, vol. 3, Issue 20, Sep. 25, 2012, American Chemical Society, pp. 2928-2933.

Yan, Jun et al., "Fast and reversible surface redox reaction of graphene-MnO2composites as supercapacitor electrodes," Carbon, vol. 48, Issue 13, Jun. 25, 2010, Elsevier Ltd., pp. 3825-3833.
Yan, Jun et al., "Recent Advances in Design and Fabrication of Electrochemical Supercapacitors with High Energy Densities," Advanced Energy Materials, vol. 4, Issue 4, 1300816, Dec. 23, 2013, Wiley-VCH Verlag GmbH & Co., pp. 1-43.
Yang, Xiaowei et al, "Bioinspired Effective Prevention of Restacking in Multilayered Graphene Films: Towards the Next Generation of High-Performance Supercapacitors," Advanced Materials, vol. 23, Issue 25, May 10, 2011, Wiley-VCH Verlag GmbH & Co., pp. 2833-2838.
Yang, Peihua et al., "Low-Cost High-Performance Solid-State Asymmetric Supercapacitors Based on $MnO_2$ Nanowires and $Fe_2O_3$ Nanotubes," Nano Letters, vol. 14, Issue 2, Jan. 1, 2014, American Chemical Society, pp. 731-736.
Yang, Xiaowei et al, "Liquid-Mediated Dense Integration of Graphene Materials for Compact Capacitive Energy Storage," Science, vol. 341, Issue 6145, Aug. 2, 2013, American Association for the Advancement of Science, 5 pages.
Yoo, Eunjoo et al., "Large Reversible Li Storage of Graphene Nanosheet Families for Use in Rechargeable Lithium Ion Batteries," Nano Letters, vol. 8, Issue 8, Jul. 24, 2008, American Chemical Society, pp. 2277-2282.
Yoo, Jung Joon et al., "Ultrathin Planar Graphene Supercapacitors," Nano Letters, vol. 11, Issue 4, Mar. 7, 2011, American Chemical Society, pp. 1423-1427.
Yu, Dingshan et al., "Scalable synthesis of hierarchically structured carbon nanotube-graphene fibres for capacitive energy storage," Nature Nanotechnology, vol. 9, Issue 7, May 11, 2014, Macmillan Publishers Limited, pp. 1-8.
Yu, Guihua et al., "Solution-Processed Graphene/$MnO_2$Nanostructured Textiles for High-Performance Electrochemical Capacitors," Nano Letters, vol. 11, Issue 7, Jun. 13, 2011, American Chemical Society, pp. 2905-2911.
Yu, Pingping et al., "Graphene-Wrapped Polyaniline Nanowire Arrays on Nitrogen-Doped Carbon Fabric as Novel Flexible Hybrid Electrode Materials for High-Performance Supercapacitor," Langmuir, vol. 30, Issue 18, Apr. 24, 2014, American Chemical Society, pp. 5306-5313.
Yu, Pingping et al., "Polyaniline Nanowire Arrays Aligned on Nitrogen-Doped Carbon Fabric for High-Performance Flexible Superc. apacitors," Langmuir, vol. 29, Issue 38, Aug. 28, 2013, American Chemical Society, 8 pages.
Yu, Zenan et al., "Supercapacitor electrode materials: nanostructures from 0 to 3 dimensions," Energy & Environmental Science, vol. 8, Issue 3, Dec. 3, 2014, The Royal Society of Chemistry, pp. 702-730.
Zhang, Jintao et al., "A high-performance asymmetric supercapacitor fabricated with graphene-based electrodes," Energy & Environmental Science, vol. 4, Issue 10, Aug. 2, 2011, The Royal Society of Chemistry, pp. 4009-4015.
Zhang, Li et al., "High Voltage Super-capacitors for Energy Storage Devices Applications," 14th Symposium on Electromagnetic Launch Technology, Jun. 10-13, 2008, IEEE, pp. 1-4.
Zhang, Long et al., "Porous 3D graphene-based bulk materials with exceptional high surface area and excellent conductivity for supercapacitors," Scientific Reports, vol. 3, Issue 1408, Mar. 11, 2013, Nature Publishing Group, pp. 1-9.
Zhang, Yonglai et al., "Direct imprinting of microcircuits on graphene oxides film by femtosecond laser reduction," Nano Today, vol. 5, Issue 1, Jan. 19, 2010, Elsevier Ltd., pp. 15-20.
Zhang, Zheye et al., "Facile Synthesis of 3D $MnO_2$-Graphene and Carbon Nanotube-Graphene Composite Networks for High-Performance, Flexible, All-Solid-State Asymmetric Supercapacitors," Advanced Energy Materials, vol. 4, Issue 10, Jul. 15, 2014, Wiley-VCH Verlag GmbH & Co. KGaA, Weinheim, pp. 1-9.
Zhang, Zhongshen et al., "A New-Type Ordered Mesoporous Carbon/Polyaniline Composites Prepared by a Two-step Nanocasting Method for High Performance Supercapacitor Applications," Journal of Materials Chemistry A, vol. 2, Issue 39, Aug. 13, 2014, Royal Society of Chemistry, pp. 1-25.
Zhao, Xin et al., "Incorporation of Manganese Dioxide within Ultraporous Activated Graphene for High-Performance Electro-

(56) References Cited

OTHER PUBLICATIONS chemical Capacitors," ACS Nano, vol. 6, Issue 6, May 3, 2012, American Chemical Society, pp. 5404-5412.
Zhi, Mingjia et al, "Nanostructured carbon-metal oxide composite electrodes for supercapacitors: a review," Nanoscale, vol. 5, Issue 1, Oct. 23, 2012,The Royal Society of Chemistry, pp. 72-88.
Zhou, Chuanqiang et al., "Synthesis of Polyaniline Hierarchical Structures in a Dilute SDS/HCl Solution: Nanostructure-Covered Rectangular Tubes," Macromolecules, vol. 42, Issue 4, Jan. 27, 2009, American Chemical Society, pp. 1252-1257.
Zhou, Guangmin et al., "Graphene-Wrapped $Fe_3O_4$ Anode Material with Improved Reversible Capacity and Cyclic Stability for Lithium Ion Batteries," Chemistry of Materials, vol. 22, Issue 18, Aug. 26, 2010, American Chemical Society, pp. 5306-5313.
Zhu, Xianjun et al., "Nanostructured Reduced Graphene Oxide/ $Fe_2O_3$ Composite as a High-Performance Anode Material for Lithium Ion Batteries," ACS Nano, vol. 5, Issue 4, Mar. 28, 2011, American Chemical Society, pp. 3333-3338.
Zhu, Yanwu et al., "Carbon-Based Supercapacitors Produced by Activation of Graphene," Science, vol. 332, May 12, 2011, www.sciencemag.org, pp. 1537-1541.
Zoski, Cynthia G., "Handbook of Electrochemistry," First Edition, 2007, Las Cruces, New Mexico, USA, Elsevier B.V., 935 pages.
Non-Final Office Action for U.S. Appl. No. 13/725,073, dated Apr. 15, 2016, 32 pages.
Final Office Action for U.S. Appl. No. 13/725,073, dated Oct. 4, 2016, 38 pages.
First Examination Report for Australian Patent Application No. 2012378149, dated Jul. 28, 2016, 3 pages.
First Office Action for Chinese Patent Application No. 201280070343.4, dated Jul. 23, 2015, 29 pages.
Second Office Action for Chinese Patent Application No. 201280070343.4, dated Apr. 6, 2016, 8 pages.
Third Office Action for Chinese Patent Application No. 201280070343.4, dated Sep. 7, 2016, 25 pages..
Extended European Search Report for European Patent Application No. 12874989.2, dated Jun. 17, 2015, 6 pages.
Notice of Reason for Rejection for Japanese Patent Application No. 2014-548972, dated Feb. 7, 2017, 5 pages.
International Search Report and Written Opinion for PCT/US2012/071407, dated Nov. 12, 2013, 9 pages.
International Preliminary Report on Patentability for PCT/US2012/071407 dated Jul. 3, 2014, 6 pages.
Non-Final Office Action for U.S. Appl. No. 14/382,463, dated Jan. 6, 2017, 23 pages.
Notice of Allowance for U.S. Appl. No. 14/382,463, dated Apr. 6, 2017, 7 pages.
First Examination Report for Australian Patent Application No. 2013230195, dated May 27, 2016, 4 pages.
First Office Action and Search Report for Chinese Patent Application No. 201380023699.7, dated Nov. 21, 2016, 21 pages.
Extended European Search Report for European Patent Application No. 13757195.6, dated Jul. 1, 2015, 9 pages.
Huang, L. et al., "Pulsed laser assisted reduction of graphene oxide," Carbon, vol. 49, 2011, Elsevier, pp. 2431-2436.
Kumar, P. et al., "Graphene produced by radiation-induced reduction of graphene oxide," Sep. 26, 2010, DOI: DOI:10.1142/S0219581X11008824, 23 pages.
Notice of Preliminary Rejection for Korean Patent Application No. 10-2014-7020353, dated Apr. 15, 2019, 11 pages.
Non-Final Office Action for U.S. Appl. No. 16/029,930, dated Apr. 3, 2019, 13 pages.
Examination Report No. 1 for Australian Patent Application No. 2015277264, dated Mar. 7, 2019, 4 pages.
Interview Summary for U.S. Appl. No. 14/945,232, dated Apr. 11, 2019, 3 pages.
Notification of the Second Office Action for Chinese Patent Application No. 201580072540.3, dated Mar. 7, 2019, 12 pages.
Official Action for Eurasian Patent Application No. 201791078, dated Mar. 27, 2019, 5 pages.

Interview Summary for U.S. Appl. No. 15/382,871, dated Apr. 1, 2019, 10 pages.
Advisory Action for U.S. Appl. No. 15/382,871, dated Apr. 24, 2019, 3 pages.
Non-Final Office Action for U.S. Appl. No. 15/688,342, dated Mar. 26, 2019, 9 pages.
Luo, Zhi-Jia et al., "A timesaving, low-cost, high-yield method for the synthesis of ultrasmall uniform graphene oxide nanosheets and their application in surfactants," Nanotechnology, vol. 27, Issue 5, Dec. 16, 2015, IOP Publishing Ltd, pp. 1-8.
Maiti, Sandipan et al., "Interconnected Network of $MnO_2$ Nanowires with a "Cocoonlike" Morphology: Redox Couple-Mediated Performance Enhancement in Symmetric Aqueous Supercapacitor," ACS Applied Materials & Interfaces, vol. 6, Issue 13, Jun. 16, 2014, American Chemical Society, pp. 10754-10762.
Maiti, Uday Narayan et al., "Three-Dimensional Shape Engineered, Interfacial Gelation of Reduced Graphene Oxide for High Rate, Large Capacity Supercapacitors," vol. 26, Issue 4, Jan. 29, 2014, Wiley-VCH Verlag GmbH & Co., pp. 615-619.
Mao, Lu et al., "Surfactant-stabilized graphene/polyaniline nanofiber composites for high performance supercapacitor electrode," Journal of Materials Chemistry, vol. 22, Issue 1, Oct. 12, 2011, The Royal Society of Chemistry, pp. 80-85.
Marcano, Daniela C. et al., "Improved Synthesis of Graphene Oxide," ACS Nano, vol. 4, Issue 8, Jul. 22, 2010, American Chemical Society, pp. 4806-4814.
Miller, John R. et al., "Electrochemical Capacitors for Energy Management," Materials Science, vol. 321, Aug. 1, 2008, AAAS, pp. 651-652.
Moosavifard, Seyyed E. et al., "Designing 3D highly ordered nanoporous CuO electrodes for high-performance asymmetric supercapacitors," ACS Applied Materials & Interfaces, vol. 7, Issue 8, American Chemical Society, 13 pages.
Moussa, Mahmoud et al, "Free-Standing Composite Hydrogel Film for Superior Volumetric Capacitance," Journal of Materials Chemistry A, vol. 3, Issue 30, Jun. 19, 2015, The Royal Society of Chemistry, pp. 1-8.
Naoi, Katsuhiko et al., "Second generation 'nanohybrid supercapacitor': Evolution of capacitive energy storage devices," Energy & Environmental Science, vol. 5, Issue 11, Sep. 14, 2012, The Royal Society of Chemistry, pp. 9363-9373.
Nathan, Arokia et al., "Flexible Electronics: The Next Ubiquitous Platform," Proceedings of the IEEE, vol. 100, Special Centennial Issue, May 13, 2012, IEEE, pp. 1486-1517.
Niu, Zhiqiang et al., "A Leavening Strategy to Prepare Reduced Graphene Oxide Foams," Advanced Materials, vol. 24, Issue 30, Aug. 8, 2012, Wiley-VCH Verlag GmbH & Co., pp. 1-7.
Oudenhoven, Jos F. M. et al., "All-Solid-State Lithium-Ion Microbatteries: A Review of Various Three-Dimensional Concepts," Advanced Energy Matterials, vol. 1, Issue 1, Wiley-VCH Verlag GmbH & Co. KGaA, Weinheim, pp. 10-33.
Paravannoor, Anjali et al., "High voltage supercapacitors based on carbon-grafted NiO nanowires interfaced with an aprotic ionic liquid," Chemical Communications, vol. 51, Issue 28, Feb. 26, 2015, The Royal Society of Chemistry, pp. 1-4.
Patel, Mehul N. et al., "Hybrid $MnO_2$-disordered mesoporous carbon nanocomposites: synthesis and characterization as electrochemical pseudocapacitor electrodes," Journal of Materials Chemistry, vol. 20, Issue 2, Nov. 11, 2009, The Royal Society of Chemistry, pp. 390-398.
Pech, David et al, "Ultrahigh-power micrometre-sized supercapacitors based on onion-like carbon," Nature Nanotechnology, vol. 5, Sep. 2010, Macmillan Publishers Limited, 10 pages.
Pendashteh, Afshin et al., "Fabrication of anchored copper oxide nanoparticles on graphene oxide nanosheets via an electrostatic coprecipitation and its application as supercapacitor," Electrochimica Acta, vol. 88, Oct. 29, 2012, Elsevier Ltd., pp. 347-357.
Pendashteh, Afshin et al., "Facile synthesis of nanostructured $CuCo_2O_4$ as a novel electrode material for high-rate supercapacitors," vol. 50, Issue 16, Dec. 17, 2013, The Royal Society of Chemistry, 4 pages.
Pendashteh, Afshin et al., "Highly Ordered Mesoporous $CuCo_2O_4$ Nanowires, a Promising Solution for High-Performance Supercapaci-

(56) References Cited

OTHER PUBLICATIONS tors," Chemistry of Materials, vol. 27, Issue 11, Apr. 20, 2015, American Chemical Society, pp. 1-11.
Qing, Xutang et al., "P/N/O co-doped carbonaceous materials based supercapacitor with voltage up to 1.9 V in the aqueous electrolyte," RSC Advances, vol. 4, Issue 99, Oct. 21, 2014, Royal Society of Chemistry, pp. 1-22.
Qiu, Ling et al., "Controllable Corrugation of Chemically Converted Graphene Sheets in Water and Potential Application for Nanofiltration," Chemical Communications, vol. 47, 2011, pp. 5810-5812.
Qu, Qunting et al., "Core-Shell Structure of Polypyrrole Grown on $V_2O_5$ Nanoribbon as High Performance Anode Material for Supercapacitors," Advanced Energy Materials, vol. 2, Issue 8, 2012, Wiley-VCH Verlag GmbH & Co., pp. 1-6.
Raccichini, Rinaldo et al., "The role of graphene for electrochemical energy storage," Nature Materials, vol. 14, Issue 3, Dec. 22, 2014, Macmillan Publishers Limited, pp. 1-9.
Samitsu, Sadaki et al., "Flash freezing route to mesoporous polymer nanofibre networks," Nature Communications, vol. 4, Issue 2653, Oct. 22, 2013, Macmillan Publishers Limited, pp. 1-7.
Shae, Yuanlong et al., "Fabrication of large-area and high-crystallinity photoreduced graphene oxide films via reconstructed two-dimensional multilayer structures," NPG Asia Materials, vol. 6, Issue 8, e119, Aug. 15, 2014, Nature Publishing Group, pp. 1-9.
Shao, Yuanlong et al., "Graphene-based materials for flexible supercapacitors," Chemical Society Review, vol. 44, Issue 11, Apr. 22, 2015, The Royal Society of Chemistry, 27 pages.
Shao, Yuanlong et al., "High-performance flexible asymmetric supercapacitors based on 3D porous graphene/$MnO_2$ nanorod and graphene/Ag hybrid thin-film electrodes," Journal of Materials Chemistry C, vol. 1, Dec. 5, 2012, The Royal Society of Chemistry, pp. 1245-1251.
Sheats, James R., "Manufacturing and commercialization issues in organic electronics," Journal of Materials Research, vol. 19, Issue 7, Jul. 2004, Materials Research Society, pp. 1974-1989.
Shen, Caiwei et al., "A high-energy-density micro supercapacitor of asymmetric $MnO_2$-carbon configuration by using micro-fabrication technologies," Journal of Power Sources, vol. 234, Feb. 9, 2013, Elsevier B.V., pp. 302-309.
Shen, Jiali et al., "High-Performance Asymmetric Supercapacitor Based on Nano-architectured Polyaniline/Graphene/Carbon Nanotube and Activated Graphene Electrodes," ACS Applied Materials & Interfaces, vol. 5, Issue 17, Aug. 9, 2013, American Chemical Society, 36 pages.
Shown, Indrajit et al., "Conducting polymer-based flexible supercapacitor," Energy Science & Engineering, vol. 3, Issue 1, Nov. 19, 2014, Society of Chemical Industry and John Wiley & Sons Ltd., pp. 1-25.
Simon, P. et al., "Capacitive Energy Storage in Nanostructured Carbon-Electrolyte Systems," Accounts of Chemical Research, vol. 46, Issue 5, Jun. 6, 2012, American Chemical Society, 10 pages.
Simon, Patrice et al., "Materials for electrochemical capacitors," Nature Materials, vol. 7, Issue 11, Nov. 2008, Macmillan Publishers Limited, pp. 845-854.
Simon, Patrice et al., "Where Do Batteries End and Supercapacitors Begin?" Science, vol. 343, Issue 6176, Mar. 14, 2014, American Association for the Advancement of Science, 3 pages.
Snook, Graeme A. et al., "Conducting-polymer-based supercapacitor devices and electrodes," Journal of Power Sources, vol. 196, Jul. 15, 2010, Elsevier B.V., pp. 1-12.
Stoller, Meryl D. et al., "Graphene-Based Ultracapacitors," Nano Letters, vol. 8, Issue 10, Sep. 13, 2008, American Chemical Society, pp. 3498-3502.
Strong, Veronica et al., "Patterning and Electronic Tuning of Laser Scribed Graphene for Flexible All-Carbon Devices," ACS Nano, vol. 6, Issue 2, Jan. 13, 2012, American Chemical Society, p. 1395-1403.
Su, Zijin et al., "Scalable fabrication of $MnO_2$ nanostructure deposited on free-standing Ni nanocone arrays for ultrathin, flexible, high-performance micro-supercapacitor," Energy and Environmental Science, vol. 7, May 28, 2014, The Royal Society of Chemistry, pp. 2652-2659.
Sumboja, Afriyanti et al., "Large Areal Mass, Flexible and Free-Standing Reduced Graphene Oxide/Manganese Dioxide Paper for Asymmetric Supercapacitor Device," Advanced Materials, vol. 25, Issue 20, May 28, 2013, Wiley-VCH Verlag GmbH & Co. KGaA, Weinheim, pp. 2809-2815.
Tian, Yuyu et al., "Synergy of $W_{18}O_{49}$ and Polyaniline for Smart Supercapacitor Electrode Integrated with Energy Level Indicating Functionality," Nano Letters, vol. 14, Issue 4, Mar. 4, 2014, American Chemical Society, pp. 2150-2156.
Toupin, Mathieu et al., "Charge Storage Mechanism of $MnO_2$ Electrode Used in Aqueous Electrochemical Capacitor," Chemistry of Materials, vol. 16, Issue 16, Jul. 16, 2004, American Chemical Society, pp. 3184-3190.
Tran, Henry D. et al., "The oxidation of aniline to produce "polyaniline": a process yielding many different nanoscale structures," Journal of Materials Chemistry, vol. 21, Issue 11, Nov. 25, 2010, The Royal Society of Chemistry, pp. 3534-3550.
Viculis, Lisa M. et al., "A Chemical Route to Carbon Nanoscrolls," Science, vol. 299, Issue 5611, Feb. 28, 2003, American Association for the Advancement of Science, 2 pages.
Vonlanthen, David et al., "A Stable Polyaniline-Benzoquinone-Hydroquinone Supercapacitor," Advanced Materials, vol. 26, Issue 30, Jun. 13, 2014, Wiley-VCH Verlag GmbH & Co., pp. 1-6.
Wallace, Gordon G. et al., "Processable aqueous dispersions of graphene nanosheets," Nature Nanotechnology, vol. 3, Issue 2, 2008, Nature Publishing Group, pp. 101-105.
Wang, Gongkai et al., "Flexible Pillared Graphene-Paper Electrodes for High-Performance Electrochemical Supercapacitors," Small, vol. 8, Issue 3, Dec. 8, 2011, pp. 452-459.
Wang, Guoping et al, "A review of electrode materials for electrochemical supercapacitors," Chemical Society Reviews, vol. 41, Jul. 21, 2011, The Royal Society of Chemistry, pp. 797-828.
Wang, Guoxiu et al., "Graphene nanosheets for enhanced lithium storage in lithium ion batteries," Carbon, vol. 47, Issue 8, Apr. 1, 2009, Elsevier Ltd., pp. 2049-2053.
Wang, Hailiang et al., "$Mn_3O_4$-Graphene Hybrid as a High-Capacity Anode Material for Lithium Ion Batteries," Journal of the American Chemical Society, vol. 132, Issue 40, Oct. 13, 2010, American Chemical Society, pp. 13978-13980.
Wang, Huanlei et al., "Graphene—Nickel Cobaltite Nanocomposite Asymmetrical Supercapacitor with Commercial Level Mass Loading," Nano Research, vol. 5, Issue 9, Sep. 2012, Tsinghua University Press and Springer-Verlag Berlin Heidelberg, pp. 605-617.
Wang, Kai et al., "Flexible supercapacitors based on cloth-supported electrodes of conducting polymer nanowire array/SWCNT composites," Journal of Materials Chemistry, vol. 21, Issue 41, Sep. 20, 2011, The Royal Society of Chemistry, pp. 16373-16378.
Notice of Reasons for Rejection for Japanese Patent Application No. 2014-561017, dated Mar. 21, 2017, 10 pages.
International Search Report and Written Opinion for PCT/US2013/029022, dated Jun. 26, 2013, 13 pages.
International Preliminary Report on Patentability for PCT/US2013/029022 dated Sep. 18, 2014, 9 pages.
International Search Report and Written Opinion for International Patent Application No. PCT/US2015/036082, dated Aug. 27, 2015, 15 pages.
International Preliminary Report on Patentability for International Patent Application No. PCT/US2015/036082, dated Dec. 29, 2016, 12 pages.
International Search Report and Written Opinion for International Patent Application No. PCT/US2015/061400, dated Mar. 29, 2016, 20 pages.
Invitation to Pay Additional Fees for International Patent Application No. PCT/US2016/067468, dated Feb. 13, 2017, 2 pages.
Conway, B. E., "Chapter 2: Similarities and Differences between Supercapacitors and Batteries for Storing Electrical Energy," Electrochemical Supercapacitors: Scientific Fundamentals and Technological Applications (book), 1999, New York, Springer Science + Business Media, pp. 11-12.

(56) References Cited

OTHER PUBLICATIONS

Conway, B. E., "Chapter 3: Energetics and Elements of the Kinetics of Electrode Processes," Electrochemical Supercapacitors: Scientific Fundamentals and Technological Applications (book), 1999, New York, Springer Science + Business Media, pp. 33-34.
Ozawa, Kazunori, "Lithium-Cell System—Nonaqueous Electrolyte System," Lithium Ion Rechargeable Batteries (book), Chapter 1: General Concepts, Section 1.1.2, 2009, Wiley-VCH Verlag GmbH & Co. KGaA, 5 pages.
Root, Michael, "Electric Vehicles," The TAB™ Battery Book: An In-Depth Guide to Construction, Design, and Use (book), Chapter 2: The Many Uses of Batteries, 2011, The McGraw-Hill Companies, 4 pages.
Kaewsongpol, Tanon et al., "High-performance supercapacitor of electrodeposited porous 3Dpolyaniline nanorods on functionalized carbon fiber paper: Effects of hydrophobic and hydrophilic surfaces of conductive carbon paper substrates," Materials Today Communications, vol. 4, Aug. 19, 2015, Elsevier Ltd., pp. 176-185.
Yan, Jun et al., "Preparation of graphene nanosheet/carbon nanotube/polyaniline composite as electrode material for supercapacitors," Journal of Power Sources, vol. 195, Issue 9, Nov. 11, 2009, Elsevier B.V., pp. 3041-3045.
Non-Final Office Action for U.S. Appl. No. 13/725,073, dated Aug. 28, 2017, 41 pages.
Fourth Office Action for Chinese Patent Application No. 201280070343.4, dated Apr. 26, 2017, 22 pages.
Examination Report for European Patent Application No. 12874989.2, dated Jul. 24, 2017, 5 pages.
Notice of Reason for Rejection for Japanese Patent Application No. 2014-548972, dated May 23, 2017, 4 pages.
Second Office Action for Chinese Patent Application No. 201380023699.7, dated Aug. 9, 2017, 8 pages.
Communication pursuant to Article 94(3) EPC for European Patent Application No. 13757195.6, dated Jul. 6, 2017, 3 pages.
International Preliminary Report on Patentability for International Patent Application No. PCT/US2015/061400, dated Jun. 1, 2017, 16 pages.
International Search Report and Written Opinion for International Patent Application No. PCT/US2016/067468, dated Apr. 21, 2017, 10 pages.
International Search Report and Written Opinion for International Patent Application No. PCT/US2017/014126, dated Apr. 20, 2017, 13 pages.
International Search Report and Written Opinion for International Patent Application No. PCT/US2017/024716, dated Jun. 20, 2017, 13 pages.
International Search Report and Written Opinion for International Patent Application No. PCT/US2017/023632, dated May 31, 2017, 11 pages.
First Office Action for Canadian Patent Application No. 2,862,806, dated Nov. 22, 2018, 5 pages.
Notification of the First Office Action for Chinese Patent Application No. 201580043429.1, dated Oct. 29, 2018, 19 pages.
International Search Report and Written Opinion for International Patent Application No. PCT/US2018/041728, dated Nov. 9, 2018, 10 pages.
Corrected Notice of Allowability for U.S. Appl. No. 15/319,286, dated Nov. 30, 2018, 5 pages.
Final Office Action for U.S. Appl. No. 14/945,232, dated Aug. 10, 2018, 7 pages.
Notification of the First Office Action for Chinese Patent Application No. 201580072540.3, dated Jun. 25, 2018, 14 pages.
International Preliminary Report on Patentability for International Patent Application No. PCT/US2017/014126, dated Aug. 2, 2018, 10 pages.
International Search Report and Written Opinion for International Patent Application No. PCT/US2017/048883, dated Dec. 26, 2017, 10 pages.
Non-Final Office Action for U.S. Appl. No. 14/945,232, dated Jan. 29, 2018, 9 pages.
Extended European Search Report for European Patent Application No. 15809519.0, dated Feb. 5, 2018, 10 pages.
Decision on Rejection for Chinese Patent Application No. 201280070343.4, dated Jan. 5, 2018, 18 pages. X.
Non-Final Office Action for U.S. Appl. No. 15/612,405, dated Feb. 9, 2018, 9 pages.
Decision to Grant a Patent for Japanese Patent Application No. 2014-561017, dated Mar. 13, 2018, 4 pages.
Park, S. et al., "Colloidal Suspensions of Highly Reduced Graphene Oxide in a Wide Variety of Organic Solvents," Nano Letters, vol. 9, No. 4, 2009, American Chemical Society, pp. 1593-1597.
Applicant-Initiated Interview Summary for U.S. Appl. No. 15/427,210, dated May 29, 2019, 3 pages.
Notice of Reexamination for Chinese Patent Application No. 201280070343.4, dated Jun. 27, 2019, 14 pages.
Non-Final Office Action for U.S. Appl. No. 15/612,405, dated Jun. 18, 2019, 12 pages.
Notification of the Second Office Action for Chinese Patent Application No. 201580043429.1, dated Jun. 20, 2019, 9 pages.
Final Office Action for U.S. Appl. No. 14/945,232, dated Jul. 17, 2019, 8 pages.
Notice of Acceptance for Australian Patent Application No. 2015349949, dated Jul. 12, 2019, 3 pages.
Notice of Allowance for U.S. Appl. No. 15/382,871, dated May 17, 2019, 10 pages.
Extended European Search Report for European Patent Application No. 16879927.8, dated Jul. 9, 2019, 14 pages.
Partial Supplementary European Search Report for European Patent Application No. 17741923.1, dated Jul. 23, 2019, 13 pages.
Non-Final Office Action for U.S. Appl. No. 15/472,409, dated May 31, 2019, 12 pages.
Non-Final Office Action for U.S. Appl. No. 15/466,425, dated Jul. 10, 2019, 8 pages.
Non-Final Office Action for U.S. Appl. No. 15/410,404, dated May 24, 2019, 9 pages.
Decision on Rejection for Chinese Patent Application No. 201380023699.7, dated Aug. 16, 2018, 11 pages.
International Preliminary Report on Patentability for International Patent Application No. PCT/US2017/024716, dated Oct. 11, 2018, 10 pages.
International Preliminary Report on Patentability for International Patent Application No. PCT/US2017/023632, dated Oct. 4, 2018, 8 pages.
Invitation to Pay Additional Fees for International Patent Application No. PCT/US2018/041728, dated Sep. 12, 2018, 2 pages.
Notice of Allowance for U.S. Appl. No. 15/319,286, dated Oct. 1, 2018, 8 pages.
Non-Final Office Action for U.S. Appl. No. 15/410,404, dated Sep. 27, 2018, 9 pages.
Advisory Action for U.S. Appl. No. 14/945,232, dated Oct. 15, 2018, 3 pages.
Braz, Elton P., et al., "Effects of Gamma Irradiation in Graphene/Poly(ethylene Oxide) Nanocomposites," 2013 International Nuclear Atlantic Conference—INAC 2013, Nov. 24-29, 2013, Recife, PE, Brazil, 7 pages.
Hu, Liangbing, et al., "Lithium-Ion Textile Batteries with Large Areal Mass Loading," Advanced Energy Materials, vol. 1, Issue 6, Oct. 6, 2011, pp. 1012-1017.
Extended European Search Report for European Patent Application No. 15861794.4, dated Oct. 2, 2018, 13 pages.
Corrected Notice of Allowability for U.S. Appl. No. 15/319,286, dated Oct. 29, 2018, 5 pages.
Final Office Action for U.S. Appl. No. 13/725,073, dated Apr. 6, 2018, 37 pages.
Notice of Allowance for U.S. Appl. No. 15/612,405, dated May 16, 2018, 8 pages.
Third Office Action and Search Report for Chinese Patent Application No. 201380023699.7, dated Mar. 9, 2018, 16 pages.
International Search Report and Written Opinion for International Patent Application No. PCT/US2017/038992, dated Sep. 21, 2017, 12 pages.
Examination Report for European Patent Application No. 13757195.6, dated Jun. 13, 2018, 7 pages.

(56) References Cited

OTHER PUBLICATIONS

Partial Supplementary European Search Report for European Patent Application No. 15861794.4, dated Jun. 28, 2018, 16 pages.
International Preliminary Report on Patentability for International Patent Application No. PCT/US2016/067468, dated Jul. 5, 2018, 7 pages.
Non-Final Office Action for U.S. Appl. No. 15/319,286, dated Jun. 27, 2018, 9 pages.
Non-Final Office Action for U.S. Appl. No. 15/382,871, dated Jun. 27, 2018, 11 pages.
Non-Final Office Action for U.S. Appl. No. 15/472,409, dated Jun. 29, 2018, 11 pages.
Acerce, Muharrem et al., "Metallic 1T phase $MoS_2$ nanosheets as supercapacitor electrode materials," Nature Nanotechnology, vol. 10, Mar. 23, 2015, Macmillan Publishers Limited, pp. 1-6.
Allen, Matthew J. et al., "Honeycomb Carbon: A Review of Graphene," Chemical Reviews, vol. 110, Issue 1, Jul. 17, 2009, American Chemical Society, pp. 132-145.
Augustyn, Veronica et al., "High-rate electrochemical energy storage through $Li^+$ intercalation pseudocapacitance," Nature Materials, vol. 12, Jun. 2013, www.nature.com/naturematerials, Macmillan Publishers Limited, pp. 518-522.
Author Unknown, "125 Volt Transportation Module," Maxwell Technologies, retrieved Apr. 13, 2016, website last modified Mar. 14, 2013, www.maxwell.com/products/ultracapacitors/125v-tranmodules, Maxwell Technologies, Inc., 2 pages.
Author Unknown, "ELTON: Super Capactions," www.elton-cap.com/, Retrieved Apr. 15, 2016, ELTON, 1 page.
Author Unknown, "ELTON: Products and Technology," https://web.archive.org/web/20160306044847/http:/www.elton-cap.com/products/, dated Mar. 6, 2016, retrieved Mar. 15, 2017, ELTON, 2 pages.
Author Unknown, "Monthly battery sales statistics," Battery Association of Japan (BAJ), retrieved Apr. 13, 2016, website last modified Dec. 2010, web.archive.org/web/20110311224259/http://www.baj.or.jp/e/statistics/02.php, Battery Association of Japan, 1 page.
Author Unknown, "Turnigy Graphene Batteries," Batteries & Accessories, https://hobbyking.com/en_us/batteries-accessories/tumigy-graphene-2.html, retrieved Apr. 3, 2017, HobbyKing, 39 pages.
Arthur, Timothy, S. et al., "Three-dimensional electrodes and battery architectures," MRS Bulletin, vol. 36, Jul. 2011, Materials Research Society, pp. 523-531.
Bai, Ming-Hua et al., "Electrodeposition of vanadium oxide-polyaniline composite nanowire electrodes for high energy density supercapacitors," Journal of Materials Chemistry A, vol. 2, Issue 28, Jan. 29, 2014, The Royal Society of Chemistry, pp. 10882-10888.
Beidaghi, Majid, et al., "Capacitive energy storage in micro-scale devices: recent advances in design and fabrication of micro-supercapacitors," Energy and Environmental Science, vol. 7, Issue 3, Jan. 2, 2014, Royal Society of Chemistry, pp. 867-884.
Beidaghi, Majid et al., "Micro-Supercapacitors Based on Interdigital Electrodes of Reduced Graphene Oxide and Carbon Nanotube Composites with Ultra high Power Handling Performance," Advanced Functional Materials, vol. 22, Issue 21, Nov. 2, 2012, Wiley-VCH Verlag GmbH & Co. KGaA, Weinheim, pp. 4501-4510.
Beidaghi, Majid et al.,"Micro-supercapacitors based on three dimensional interdigital polypyrrole/C-MEMS electrodes," Electrochimica Acta, vol. 56, Issue 25, Oct. 30, 2011, Elsevier Ltd., pp. 9508-9514.
Bélanger, Daniel et al., "Manganese Oxides: Battery Materials Make the Leap to Electrochemical Capacitors," Electrochemical Society Interface, vol. 17, Issue 1, Spring 2008, The Electrochemical Society, pp. 49-52.
Bian, Li-Jun et al., "Self-doped polyaniline on functionalized carbon cloth as electroactive materials for supercapacitor," Electrochimica Acta, vol. 64, Dec. 29, 2011, Elsevier Ltd., pp. 17-22.
Bouville, Florian et al., "Strong, tough and stiff bioinspired ceramics from brittle constituents," Nature Materials, vol. 13, Issue 5, Mar. 23, 2014, Macmillan Publishers Limited, pp. 1-7.

Brain, Marshall et al., "How Batteries Work," Battery Arrangement and Power—HowStuffWorks, http://electronics.howstuffworks.com/everyday-tech/battery6.htm/printable, accessed Dec. 14, 2015, HowStuffWorks, 4 pages.
Brodie, B.C., "Ueber das Atomgewicht des Graphits," Justus Liebigs Annalen der Chemie, vol. 114, Issue 1, 1860, Wiley-VCH Verlag GmbH & Co. KGaA, Weinheim, pp. 6-24.
Burke, Andrew, "R&D considerations for the performance and application of electrochemical capacitors," Electrochimica Acta, vol. 53, Jan. 26, 2007, Elsevier Ltd., pp. 1083-1091.
Cao, Liujun et al., "Direct Laser-Patterned Micro-Supercapacitors from Paintable $MoS_2$ Films," Small, vol. 9, Issue 17, Apr. 16, 2013, Wiley-VCH Verlag GmbH & Co. KGaA, Weinheim, pp. 2905-2910.
Chan, Candace K. et al, "High-performance lithium battery anodes using silicon nanowires," Nature Nanotechnology, vol. 3, Issue 1, Jan. 2008, Nature Publishing Group, pp. 31-35.
Chen, Cheng-Meng et al., "Macroporous 'bubble' graphene film via template-directed ordered-assembly for high rate supercapacitors," Chemical Communications, vol. 48, Issue 57, May 15, 2012, The Royal Society of Chemistry, pp. 1-3.
Chen, Ji et al., "High-yield preparation of graphene oxide from small graphite flakes via an improved Hummers method with a simple purification process," Carbon, vol. 81, Jan. 2015, Elsevier Ltd., pp. 1-9.
Chen, L. Y. et al., "Toward the Theoretical Capacitance of $RuO_2$ Reinforced by Highly Conductive Nanoporous Gold," Advanced Energy Materials, vol. 3, Issue 7, Jul. 2014, Wiley-VCH Verlag GmbH & Co. KGaA, Weinheim, pp. 351-856.
Chen, Wei et al., "High-Performance Nanostructured Supercapacitors on a Sponge," Nano Letters, vol. 11, Issue 12, Sep. 16, 2011, American Chemical Society, 22 pages.
Chen, Zongping et al, "Three-dimensional flexible and conductive interconnected graphene networks grown by chemical vapour deposition," Nature Materials, vol. 10, Issue 6, Jun. 2011, Macmillan Publishers Limited, pp. 424-428.
Cheng, Yingwen et al., "Synergistic Effects from Graphene and Carbon Nanotubes EnableFlexible and Robust Electrodes for High-PerformanceSupercapacitors," Nano Letters, vol. 12, Issue 8, Jul. 23, 2012, American Chemical Society, pp. 4206-4211.
Chi, Kai et al., "Freestanding Graphene Paper Supported Three-Dimensional Porous Graphene-Polyaniline Nanocomposite Synthesized by Inkjet Printing and in Flexible All-Solid-State Supercapacitor," ACS Applied Materials & Interfaces, vol. 6, Issue 18, Sep. 10, 2014, American Chemical Society, 8 pages.
Chmiola, John et al., "Monolithic Carbide-Derived Carbon Films for Micro-Supercapacitors," Science, vol. 328, Issue 5977, Apr. 2010, American Association for the Advancement of Science, 4 pages.
Choi, Bong Gill et al., "3D Macroporous Graphene Frameworks for Supercapacitors with High Energy and Power Densities," ACS Nano, vol. 6, Issue 5, Apr. 23, 2012, American Chemical Society, pp. 4020-4028.
Cooper, A. et al., "The UltraBattery—A new battery design for a new beginning in hybrid electric vehicle energy storage," Journal of Power Sources, vol. 188, Issue 2, Dec. 6, 2008, Elsevier B.V. pp. 642-649.
Deville, Sylvain, "Freeze-Casting of Porous Ceramics: A Review of Current Achievements and Issues," Advanced Engineering Materials, vol. 10, Issue 3, Mar. 20, 2008, Wiley-VCH Verlag GmbH & Co., pp. 155-169.
Deville, Sylvain, "Metastable and unstable cellular solidification of colloidal suspensions," Nature Materials, vol. 8, Dec. 2009, Macmillan Publishers Limited, pp. 966-972.
De Volder, Michael et al., "Corrugated Carbon Nanotube Microstructures with Geometrically Tunable Compliance," ACS Nano, vol. 5, Issue 9, Aug. 1, 2011, pp. 7310-7317.
Dunn, Bruce et al., "Electrical Energy Storage for the Grid: A Battery of Choices," Science, vol. 334, Issue 928, Nov. 18, 2011, American Association for the Advancement of Science, pp. 928-935.

(56) References Cited

OTHER PUBLICATIONS

Eda, Goki et al., "Chemically Derived Graphene Oxide: Towards Large-Area Thin-Film Electronics and Optoelectronics," Advanced Materials, vol. 22, Issue 22, Apr. 28, 2010, Wiley-VCH Verlag GmbH & Co., pp. 2392-2415.
El-Kady, Maher F. et al., "Engineering Three-Dimensional Hybrid Supercapacitors and Micro-Supercapacitors for High-Performance Integrated Energy Storage," Proceedings of the National Academy of Sciences of the United States of America, vol. 112, Issue 14, Apr. 7, 2015, National Academy of Sciences, pp. 4233-4238.
El-Kady, Maher F. et al., "Laser Scribing of High-Performance and Flexible Graphene-Based Electrochemical Capacitors," Science Magazine, Mar. 16, 2012, vol. 335, No. 6074, 6 pages.
El-Kady, Maher F. et al., "Laser Scribing of High-Performance and Flexibile Graphene-Based Electrochemical Capacitors," Science, vol. 335, Issue 6074, Mar. 16, 2012, www.sciencemag.org/cgi/content/full/335/6074/1326/DC1, American Association for the Advancement of Science, 25 pages.
El-Kady, Maher F. et al., "Scalable Fabrication of High-Power Graphene Micro-Supercapacitors for Flexible and On-Chip Energy Storage," Nature Communications, vol. 4, Issue 1475, Feb. 12, 2013, Macmillan Publishers Limited, pp. 1-9.
El-Kady, Maher F. et al., "Supplementary Information: Scalable Fabrication of High-Power Graphene Micro-Supercapacitors for Flexible and On-Chip Energy Storage", Nature Communications, Submitted for Publication: Oct. 1, 2012, 23 pages.
Fan, Zhuangjun et al., "Asymmetric Supercapacitors Based on Graphene/$MnO_2$ and Activated Carbon Nanofiber Electrodes with High Power and Energy Density," Advanced Functional Materials, vol. 21, Issue 12, Jun. 21, 2011, Wiley-VCH Verlag GmbH & Co. KGaA, Weinheim, pp. 2366-2375.
Feng, Jun et al., "Metallic Few-Layered $VS_2$ Ultrathin Nanosheets: High Two-Dimensional Conductivity for In-Plane Supercapacitors," Journal of the American Chemical Society, vol. 133, Issue 44, Sep. 27, 2011, American Chemical Society, pp. 17832-17838.
Fischer, Anne E. et al., "Incorporation of Homogeneous, Nanoscale $MnO_2$ within Ultraporous Carbon Structures via Self-Limiting Electroless Deposition: Implications for Electrochemical Capacitors," Nano Letters, vol. 7, Issue 2, Jan. 13, 2007, American Chemical Society, pp. 281-286.
Foo, Ce Yao et al., "Flexible and Highly Scalable $V_2O_5$-rGO Electrodes in an Organic Electrolyte for Supercapacitor Devices," Advanced Energy Materials, vol. 4, Issue 12, Aug. 26, 2014, Wiley-VCH Verlag GmbH & Co. KGaA, Weinheim, pp. 1-7.
Gan, Shiyu et al., "Spontaneous and Fast Growth of Large-Area Graphene Nanofilms Facilitated by Oil/Water Interfaces," Advanced Materials, vol. 24, Issue 29, Jun. 12, 2012, Wiley-VCH Verlag GmbH & Co, pp. 3958-3964.
Gao, Wei et al., "Direct laser writing of micro-supercapacitors on hydrated graphite oxide films," Nature Nanotechnology, vol. 6, Issue 8, Jul. 2011, Macmillan Publishers Limited, p. 496-500.
Gao, Wei et al., "Direct laser writing of micro-supercapacitors on hydrated graphite oxide films," Supplementary Information, Nature Nanotechnology, vol. 6, Issue 8, Jul. 2011, Macmillan Publishers Limited, 15 pages.
Gao, Hongcai et al., "Flexible All-Solid-State Asymmetric Supercapacitors Based on Free-Standing Carbon Nanotube/Graphene and $Mn_3O_4$ Nanoparticle/Graphene Paper Electrodes," Applied Materials & Interfaces, vol. 4, Issue 12, Nov. 20, 2012, American Chemical Society, pp. 7020-7026.
Gao, Hongcai et al., "High-Performance Asymmetric Supercapacitor Based on Graphene Hydrogel and Nanostructured $MnO_2$," ACS Applied Materials and Interfaces, vol. 4, Issue 5, Apr. 30, 2012, American Chemical Society, pp. 2801-2810.
Vranes, M. et al., "Physicochemical Characterization of 1-Butyl-3-methylimidazolium and 1-Butyl-1-methylpyrrolidinium Bis{trifluoromethylsulfonyl}imide," Journal of Chemical & Engineering Data, vol. 57, Mar. 7, 2012, American Chemical Society, pp. 1072-1077.

Notice of Allowance for U.S. Appl. No. 15/427,210, dated Dec. 18, 2019, 9 pages.
Final Office Action for U.S. Appl. No. 15/612,405, dated Dec. 27, 2019, 17 pages.
Notice of Allowance for U.S. Appl. No. 14/945,232, dated Dec. 20, 2019, 9 pages.
Applicant-Initiated Interview Summary for U.S. Appl. No. 15/382,871, dated Dec. 31, 2019, 5 pages.
Corrected Notice of Allowability for U.S. Appl. No. 15/410, 404, dated Dec. 3, 2019, 6 pages.
Non-Final Office Action for U.S. Appl. No. 16/692,123, dated Dec. 27, 2019, 11 pages.
Notice of Allowance for U.S. Appl. No. 15/472,409, dated Dec. 11, 2019, 11 pages.
Office Action for Canadian Patent Application No. 2,862,806, dated Sep. 30, 2019, 3 pages.
Decision of Rejection for Japanese Patent Application No. 2016-573846, dated Oct. 29, 2019, 9 pages.
First Office Action for Chinese Patent Application No. 2016800753323, dated Aug. 27, 2019, 15 pages.
Extended European Search Report for European Patent Application No. 17741923.1, dated Nov. 15, 2019, 18 pages.
Extended European Search Report for European Patent Application No. 17776536.9, dated Oct. 30, 2019, 8 pages.
Extended European Search Report for European Patent Application No. 17771081.1, dated Oct. 22, 2019, 6 pages.
Supplemental Notice of Allowability for U.S. Appl. No. 14/945,232, dated Feb. 26, 2020, 5 pages.
Cannarella et al., "Mechanical Properties of a Battery Separator under Compression and Tension," Journal of the Electrochemical Society, vol. 161, No. 11, Sep. 26, 2014, pp. F3117-F3122.
Non-Final Office Action for U.S. Appl. No. 15/427,210, dated Sep. 3, 2019, 16 pages.
Applicant-Initiated Interview Summary for U.S. Appl. No. 16/029,930, dated Jul. 29, 2019, 4 pages.
Notice of Preliminary Rejection for Korean Patent Application No. 10-2014-7028084, dated Aug. 22, 2019, 30 pages.
Notice of Acceptance for Australian Patent Application No. 2015277264, dated Jul. 31, 2019, 3 pages.
Non-Final Office Action for U.S. Appl. No. 14/945,232, dated Sep. 3, 2019, 8 pages.
Notification of the Third Office Action for Chinese Patent Application No. 201580072540.3, dated Jul. 17, 2019, 9 pages.
Notification of Reasons for Rejection for Japanese Patent Application No. 2017-526533, dated Aug. 20, 2019, 4 pages.
Non-Final Office Action for U.S. Appl. No. 15/382,871, dated Sep. 16, 2019, 9 pages.
Non-Final Office Action for U.S. Appl. No. 16/428,409, dated Sep. 16, 2019, 12 pages.
Examination Report for European Patent Application No. 13757195.6, dated Jan. 29, 2020, 4 pages.
Office Action for Brazilian Patent Application No. 112016029468, dated Jan. 21, 2020, 6 pages.
Third Office Action for Chinese Patent Application No. 201580043429.1, dated Jan. 3, 2020, 20 pages.
Office Action for Israeli Patent Application No. 249506, dated Dec. 3, 2019, 8 pages.
Office Action for Brazilian Patent Application No. 112017010257, dated Jan. 28, 2020, 7 pages.
First Office Action for Chinese Patent Application No. 2017800076125, dated Nov. 28, 2019, 20 pages.
International Preliminary Report on Patentability for International Patent Application No. PCT/US2018/041728, dated Jan. 23, 2020, 7 pages.
Lu, J. et al., "Advanced applications of ionic liquids in polymer science," Progress in Polymer Science, vol. 34, 2009, Elsevier Ltd., pp. 431-448.
Yan, Jun et al., "High-performance supercapacitor electrodes based on highly corrugated graphene sheets," Carbon, vol. 50, 2012, Elsevier Ltd., pp. 2179-2188.
Final Office Action for U.S. Appl. No. 16/029,930, dated Nov. 15, 2019, 16 pages.

(56) References Cited

OTHER PUBLICATIONS

Notice of Allowance and Examiner-Initiated Interview Summary for U.S. Appl. No. 15/410,404, dated Oct. 25, 2019, 11 pages.
Final Office Action for U.S. Appl. No. 15/688,342, dated Oct. 17, 2019, 11 pages.
Applicant-Initiated Interview Summary for U.S. Appl. No. 15/466,425, dated Oct. 22, 2019, 3 pages.
Gao, C. et al., "Superior Cycling Performance of SiOx/C Composite with Arrayed Mesoporous Architecture as Anode Material for Lithium-Ion Batteries," Journal of the Electrochemical Society, vol. 161, No. 14, 2014, The Electrochemical Society, pp. A2216-A2221.
Grant of Patent for Korean Patent Application No. 10-2014-7020353, dated Oct. 29, 2019, 3 pages.
Office Action for Canadian Patent Application No. 2,866,250, dated Dec. 17, 2019, 3 pages.
Examination Report for European Patent Application No. 15809519.0, dated Dec. 9, 2019, 7 pages.
Official Action for Eurasian Patent Application No. 201791078, dated Nov. 6, 2019, 4 pages.
Official Action for Eurasian Patent Application No. 201892199, dated Nov. 28, 2019, 6 pages.
Extended European Search Report for European Paetnt Application No. 17816292.1, dated Jan. 7, 2020, 9 pages.
Examination Report for Indian Patent Application No. 201817044642, dated Nov. 26, 2019, 7 pages.
Official Action for Eurasian Patent Application No. 201892118, mailed Nov. 28, 2019, 4 pages.
Final Office Action for U.S. Appl. No. 15/466,425, dated Jan. 28, 2020, 8 pages.
Supplemental Notice of Allowability for U.S. Appl. No. 14/945,232, dated Feb. 12, 2020, 5 pages.
Office Action for Eurasian Patent Application No. 201990587/31, dated Mar. 26, 2020, 4 pages.
Notice of Preliminary Rejection for Korean Patent Application No. 10-2014-7028084, dated Feb. 17, 2020, 5 pages.
Examination Report for Indian Patent Application No. 201617042976, dated Mar. 13, 2020, 7 pages.
Office Action for Mexican Patent Application No. MX/a/2016/016239, dated Feb. 26, 2020, 5 pages.
Notification of Reasons for Rejection for Japanese Patent Application No. 2017-526533, dated Mar. 16, 2020, 7 pages.
Second Office Action for Chinese Patent Application No. 2016800753323, dated Mar. 5, 2020, 15 pages.
First Office Action for Chinese Patent Application No. 2017800249783, dated Jan. 6, 2020, 15 pages.
Notice of Reexamination for Chinese Patent Application No. 201280070343.4, dated Feb. 3, 2020, 7 pages.
Office Action for Vietnamese Patent Application No. 1-2016-05086, dated May 29, 2020, 2 pages.
First Office Action and Search Report for Chinese Patent Application No. 201811438766.2, dated Mar. 31, 2020, 32 pages.
Garg, R. et al., "Nanowire Mesh Templated Growth of Out-of-Plane Three-Dimensional Fuzzy Graphene," ACS Nano, vol. 11, 2017, American Chemical Society, pp. 6301-6311.
Li, Qintao et al., "Carbon nanotubes coated by carbon nanoparticles of turbostratic stacked graphenes," Carbon, vol. 46, 2008, Elsevier Ltd., pp. 434-439.
Non-Final Office Action for U.S. Appl. No. 15/688,342, dated Apr. 9, 2020, 10 pages.
Non-Final Office Action for U.S. Appl. No. 16/033,266, dated Apr. 29, 2020, 12 pages.
Official Notification for Eurasian Patent Application No. 201990068, dated Jun. 23, 2020, 5 pages.
Official Action for Eurasian Patent Application No. 201791078, dated Jun. 23, 2020, 4 pages.
Examination Report for Indian Patent Application No. 201717016755, dated Jul. 2, 2020, 6 pages.
Examination Report for Indian Patent Application No. 201817020826, dated Jul. 13, 2020, 7 pages.
Extended European Search Report for European Patent Application No. 17847303.9, dated Jul. 13, 2020, 9 pages.
First Office Action and Search Report for Chinese Patent Application No. 2017800273161, dated Jun. 5, 2020, 15 pages.
Non-Final Office Action for U.S. Appl. No. 15/466,425, dated Jul. 28, 2020, 8 pages.
Notice of Allowance for U.S. Appl. No. 16/692,123, dated Jul. 15, 2020, 9 pages.
Advisory Action for U.S. Appl. No. 15/466,425, dated Jul. 7, 2020, 3 pages.
Notice of Allowance for U.S. Appl. No. 16/223,869, dated Jul. 9, 2020, 9 pages.
Advisory Action for U.S. Appl. No. 15/612,405, dated Jun. 24, 2020, 3 pages.
Non-Final Office Action for U.S. Appl. No. 16/029,930, dated Jun. 24, 2020, 16 pages.
Final Office Action for U.S. Appl. No. 16/428,409, dated Jun. 23, 2020, 16 pages.
Office Action for Eurasian Patent Application No. 201790003, dated Feb. 26, 2020, 6 pages.
Examination Report No. 1 for Australian Patent Application No. 2019250120, dated Apr. 24, 2020, 4 pages.
Partial Supplemental European Search Report for European Patent Application No. 17847303.9, dated Apr. 3, 2020, 10 pages.
Decision of Rejection for Chinese Patent Application No. 201580072540.3, dated Apr. 22, 2020, 8 pages.
Notice of Preliminary Rejection for Korean Patent Application No. 10-2018-7030385, dated Mar. 13, 2021, 10 pages.
Notice of Reasons for Rejection for Japanese Patent Application No. 2018-549538, dated Feb. 15, 2021, 6 pages.
Partial Supplementary European Search Report for European Patent Application No. 18832324.0, dated Mar. 12, 2021, 15 pages.
Non-Final Office Action for U.S. Appl. No. 16/791,517, dated Apr. 1, 2021, 16 pages.
Applicant-Initiated Interview Summary for U.S. Appl. No. 16/428,409, dated Mar. 19, 2021, 2 pages.
Applicant-Initiated Interview Summary for U.S. Appl. No. 16/033,266, dated Apr. 8, 2021, 3 pages.
Second Office Action for Chinese Patent Application No. 201811438766.2, dated Oct. 28, 2020, 10 pages.
Notification of Reexamination for Chinese Patent Application No. 2015800725403, dated Oct. 12, 2020, 9 pages.
Office Action for Israeli Patent Application No. 252320, dated Sep. 17, 2020, 11 pages.
Examination Report for Australian Patent Application No. 2016378400, dated Sep. 22, 2020, 5 pages.
Examination Report for Taiwanese Patent Application No. 105142233, dated Sep. 25, 2020, 19 pages.
Examination Report for Australian Patent Application No. 2017209117, dated Oct. 5, 2020, 5 pages.
Examination Report for Taiwanese Patent Application No. 106109733, dated Oct. 20, 2020, 11 pages.
Notice of Allowance for U.S. Appl. No. 16/692,123, dated Oct. 21, 2020, 8 pages.
Notice of Allowance and Examiner-Initiated Interview Summary for U.S. Appl. No. 16/784,578, dated Oct. 15, 2020, 9 pages.
Notice of Allowability for U.S. Appl. No. 16/223,869, dated Sep. 15, 2020, 5 pages.
Non-Final Office Action for U.S. Appl. No. 16/428,409, dated Oct. 1, 2020, 14 pages.
Non-Final Office Action for U.S. Appl. No. 16/791,504, dated Nov. 18, 2020, 16 pages.
Zhang, Luojiang, et al., "3D porous layered double hydroxides grown on graphene as advanced electrochemical pseudocapacitor materials," Journal of Materials Chemistry A, vol. 1, 2013, pp. 9046-9053.
Notice of Acceptance for Australian Patent Application No. 2019250120, dated Nov. 11, 2020, 3 pages.
Notification of Decision of Rejection for Japanese Patent Application No. 2017-526533, dated Nov. 17, 2020, 6 pages.
Official Notification for Eurasian Patent Application No. 20182199, dated Dec. 11, 2020, 6 pages.

(56) References Cited

OTHER PUBLICATIONS

Notification of the Second Office Action for Chinese Patent Application No. 2017800249783, dated Dec. 2, 2020, 9 pages.
Official Action for Eurasion Patent Application No. 201892118, dated Dec. 11, 2020, 6 pages.
Invitation to Pay Additional Fees and Partial Search for International Patent Application No. PCT/US2020/052618, dated Nov. 30, 2020, 2 pages.
Notification of Reasons for Rejection for Japanese Patent Application No. 2018-538110, dated Jan. 20, 2021, 9 pages.
Notification of Reasons for Rejection for Japanese Patent Application No. 2018-550836, dated Feb. 12, 2021, 6 pages.
Examination Report for Taiwanese Patent Application No. 106121056, dated Feb. 3, 2021, 10 pages.
Wikipedia, "Ferromagnetism," Feb. 13, 2017, Retrieved Aug. 7, 2018 from https://en.wikipedia.org/w/index.php?title=Ferromagnetism&oldid=765289868, 1 page.
Grosu, Yaroslav et al., "Natural Magnetite for thermal energy storage: Excellent thermophysical properties, reversible latent heat transition and controlled thermal conductivity," Solar Energy Materials & Solar Cells, vol. 161, Available online Dec. 6, 2016, Elsevier B.V., pp. 170-176.
Hwang, J. Y., et al., "Boosting the Capacitance and Voltage of Aqueous Supercapacitors via Redox Charge Contribution from both Electrode and Electrolyte," Nano Today, vol. 15, Available online Jul. 22, 2017, pp. 15-25.
Karami, Hassan et al., "Sodium Sulfate Effects on the Electrochemical Behaviors of Nanostructured Lead Dioxide and Commercial Positive Plates of Lead-Acid Batteries," International Journal of Electrochemical Science, vol. 5, 2010, ESG, pp. 1046-1059.
Lee, Juhan, et al., "High Performance Hybrid Energy Storage with Potassium Ferricyanide Redox Electrolyte," Applications of Materials and Interfaces, vol. 8, Aug. 2016, ACS, pp. 23676-23687.
Notice of Allowance for U.S. Appl. No. 15/612,405, dated Sep. 8, 2020, 7 pages.
Examination Report for Indian Patent Application No. 201817023184, dated Aug. 13, 2020, 6 pages.
Examination Report for Indian Patent Application No. 201817034180, dated Aug. 13, 2020, 6 pages.
Examination Report for European Patent Application No. 17816292.1, dated Aug. 24, 2020, 4 pages.
Examination Report for Indian Patent Application No. 201817033309, dated Aug. 28, 2020, 6 pages.
Invitation to Pay Additional Fees for International Patent Application No. PCT/US2018/036846, dated Aug. 24, 2018, 2 pages.
International Search Report and Written Opinion for International Patent Application No. PCT/US2018/036846, dated Nov. 9, 2018, 14 pages.
International Preliminary Report on Patentability for International Patent Application No. PCT/US2018/036846, dated Dec. 26, 2019, 10 pages.
Non-Final Office Action for U.S. Appl. No. 16/0004,818, dated Jun. 24, 2020, 18 pages.
Dubal, D. P., et al., "Hybrid energy storage: the merging of battery and supercapacitor chemistries," Chemical Society Review, vol. 44, No. 7, 2015, pp. 1777-1790.
Gong, M., et al., "Ultrafast high-capacity NiZn battery with NiAlCo-layered double hydroxide," Energy & Environmental Science, vol. 7, No. 6, 2014, pp. 2025-2032.
Humble, P. H., et al., "Microscopic nickel-zinc batteries for use in autonomous microsystems," Journal of the Electrochemical Society, vol. 148, No. 12, 2001, pp. A1357-A1361.
Mishra, G., et al., "Layered double hydroxides: A brief review from fundamentals to application as evolving biomaterials," Applied Clay Science, vol. 153, 2018, Elsevier B.V., pp. 172-186.
Parker, J. F., et al. "Rechargeable nickel-3D zinc batteries: An energy-dense, safer alternative to lithium-ion," Science, vol. 356, No. 6336, 2017, American Association for the Advancement of Science, pp. 415-418.
Notice of Allowance for U.S. Appl. No. 15/612,405, dated Dec. 17, 2020, 8 pages.
Non-Final Office Action for U.S. Appl. No. 16/029,930, dated Jan. 6, 2021, 15 pages.
Final Office Action for U.S. Appl. No. 16/033,266, dated Jan. 6, 2021, 10 pages.
Yang, Wanlu, et al., "Solvothermal One-Step Synthesis of Ni—Al Layered Double Hydroxide/Carbon Nanotube/Reduced Graphene Oxide Sheet Ternary Nanocomposite with Ultrahigh Capacitance for Supercapacitors," Applied Materials and Interfaces, vol. 5, 2013, American Chemical Society, pp. 5443-5454.
Decision of Reexamination for Chinese Patent Application No. 201580072540.3, dated Feb. 2, 2021, 18 pages.
Notification of Reasons for Rejection for Japanese Patent Application No. 2018-532233, dated Dec. 15, 2020, 8 pages.
Examination Report for Australian Patent Application No. 185870, dated Jan. 28, 2021, 5 pages.
Official Notification for Eurasian Patent Application No. 201990068, dated Jan. 14, 2021, 6 pages.
Notice of Preliminary Rejection for Korean Patent Application No. 10-2018-7029515, dated Jan. 21, 2021, 9 pages.
International Search Report and Written Opinion for International Patent Application No. PCT/US2020/052618, dated Feb. 17, 2021, 19 pages.
Notice of Allowance for U.S. Appl. No. 15/466,425, dated Mar. 10, 2021, 9 pages.
Final Office Action for U.S. Appl. No. 16/004,818, dated Feb. 25, 2021, 24 pages.
Reexamination Decision for Chinese Patent Application No. 201280070343.4, dated Aug. 31, 2020, 19 pages.
Examination Report for Taiwanese Patent Application No. 106111115, dated Aug. 25, 2020, 17 pages.
Shao, et al., "3D Freeze-Casting of Cellular Graphene Films for Ultrahigh-Power-Density Supercapacitors," Advanced Materials, vol. 28, 2016, 8 pages.
Notice of Allowance for U.S. Appl. No. 16/428,409, dated May 14, 2021, 10 pages.
Final Office Action for U.S. Appl. No. 16/791,504, dated May 27, 2021, 16 pages.
Examination Report for European Patent Application No. 15861794.4, dated Apr. 14, 2021, 4 pages.
Examination Report for Australian Patent Application No. 2017245151, dated Mar. 25, 2021, 5 pages.
Second Office Action for Chinese Patent Application No. 2017800273161, dated Apr. 6, 2021, 8 pages.
Notification of Reasons for Rejection for Japanese Patent Application No. 2018-567030, dated Apr. 5, 2021, 8 pages.
Examination Report for Australian Patent Application No. 2017238201, dated Mar. 17, 2021, 4 pages.
An, et al., "Fabrication of graphene/polypyrrole nanotube/MnO2 nanotube composite and its supercapacitor application," European Physical Journal, Applied Physics, vol. 58, 2012, 9 pages.
Gu, et al., "Synthesis of polyaniline nanotubes with controlled rectangular or square pore shape," Materials Letters, vol. 121, 2014, pp. 12-14.
Liu, Jianhua, et al., "Synthesis of a Graphene-Polypyrrole Nanotube Composite and Its Application in Supercapacitor Electrode," Journal of The Electrochemical Society, vol. 159, Issue 6, Apr. 2012, 6 pages.
Wang, et al., "Polyaniline nanotube arrays as high-performance flexible electrodes for electrochemical energy storage devices," Journal of Materials Chemistry, vol. 22, 2012, pp. 2401-2404.
Non-Final Office Action for U.S. Appl. No. 16/751,314, dated Jul. 13, 2021, 13 pages.
Notice of Allowance for U.S. Appl. No. 16/033,266, dated Jun. 3, 2021, 9 pages.
Corrected Notice of Allowability for U.S. Appl. No. 16/033,266, dated Jun. 4, 2021, 7 pages.
Lin, Jian, et al., "Laser-induced porous graphene films from commercial polymers," Nature Communications, Dec. 2014, 8 pages.
Notice of Reasons for Refusal for Japanese Patent Application No. 2020-034093, dated Jun. 1, 2021, 10 pages.

(56) References Cited

OTHER PUBLICATIONS

Intention to Grant for European Patent Application No. 16879927.8, dated Jun. 9, 2021, 5 pages.
Official Notification for Eurasion Patent Application No. 20182199, dated Jun. 4, 2021, 12 pages.
Intention to Grant for European Patent Application No. 17776536.9, dated Jul. 2, 2021, 7 pages.
Request for additional materials for Eurasian Patent Application No. 201990587, dated May 21, 2021, 6 pages.
Written Opinion for Brazilian Patent Application No. 112018076559, dated Jun. 8, 2021, 6 pages.
Notification of the Third Office Action for Chinese Patent Application No. 2017800249783, dated May 21, 2021, 8 pages.
Official Notification for Eurasian Patent Application No. 201892118, dated Jun. 18, 2021, 8 pages.
Examination Report for European Patent Application No. 17771081.1, dated Jun. 17, 2021, 4 pages.
Extended European Search Report for European Patent Application No. 18832324.0, dated Jun. 24, 2021, 15 pages.

* cited by examiner

1 - RR1

2 - RR2    KMnO4

3 - RR3    STIR  45 MIN

4 - RR4

PRODUCTION OF CARBON-BASED OXIDE AND REDUCED CARBON-BASED OXIDE ON A LARGE SCALE

CROSS-REFERENCE

This application claims the benefit of U.S. Provisional Application No. 62/354,439, filed Jun. 24, 2016, and U.S. Provisional Application No. 62/510,021, filed May 23, 2017, which applications are incorporated herein by reference.

BACKGROUND

Provided herein are carbon-based oxide (CBO) materials and reduced carbon-based oxide (rCBO) materials, fabrication processes, and devices with improved performance and a high throughput. In some embodiments, the present disclosure provides materials and methods for synthesizing CBO and rCBO materials. Such methods avoid the shortcomings of current synthesizing methods to facilitate facile, high-throughput production of CBO and rCBO materials.

CBO and rCBO materials have been employed within a variety of products for use in several industrial applications. Although chemical reduction may be the most viable method of synthesizing CBO and rCBO materials on a large scale, the throughput and safety of current chemical reduction methods prohibit economical, high-throughput production of CBO and rCBO materials. As such, there is exists a specific unmet need for a safe, high-throughput means for production of CBO and rCBO materials.

SUMMARY

The instant disclosure provides carbon-based oxide (CBO) and reduced carbon-based oxide (rCBO) materials, fabrication processes, and devices with improved performance. The present disclosure provides materials and methods for synthesizing CBO and rCBO materials. Such methods avoid the shortcomings of current synthesizing methods to facilitate facile, high-throughput production of CBO and rCBO materials. Features of the subject matter described herein provide for a method for producing a high throughput of CBO and rCBO materials through a low-temperature process, wherein the CBO and rCBO materials exhibit high purities for applications including but not limited to inkjet printing, screen printing, printed circuit boards, radio frequency identification chips, smart fabrics, conductive coatings, gravure printing, flexographic printing, batteries, supercapacitors, electrodes, electromagnetic interference shielding, printed transistors, memory, sensors, large area heaters, electronics, and energy storage systems.

The present disclosure relates to materials comprising, and methods for production of CBO and rCBO materials (e.g., on a large scale). In some embodiments, the CBO material comprises graphite oxide (GO) or graphene oxide. In some embodiments, the rCBO material comprises reduced graphite oxide (rGO) or reduced graphene oxide. While these processes or methods may be described herein primarily in the context of graphite oxide and reduced graphite oxide, the methods may be used or adapted for production or synthesis of any CBO and/or rCBO.

In some embodiments, the characteristic(s) of the graphite feedstock (e.g., physical and chemical properties) may affect the type or quality of the graphite oxide. In some embodiments, a graphite feedstock may include various grades or purities (e.g., carbon content measured as, for example, weight-percent graphitic carbon ($C_g$)), types (e.g., amorphous graphite (e.g., 60%-85% carbon), flake graphite (e.g., greater than 85% carbon) or vein graphite (e.g., greater than 90% carbon)), sizes (e.g., mesh size), shapes (e.g., large flake, medium, flake, powder, or spherical graphite), and origin (e.g., synthetic or natural, such as, for example, natural flake graphite). For example, the mesh size of the graphite may affect the resulting graphite oxide. Mesh sizes may be converted to size in other dimensions (e.g., microns). Other examples of graphite feedstocks are provided elsewhere herein.

In some embodiments the grade of the graphite by weight is about 1% to about 100%. In some embodiments the grade of the graphite by weight is at least about 1%. In some embodiments the grade of the graphite by weight is at most about 100%. In some embodiments the grade of the graphite by weight is about 1% to about 5%, about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 100%, about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some embodiments the grade of the graphite by weight is about 1%, about 5%, about 10%, about 20%, about 30%, about 40%, about 50%, about 60%, about 70%, about 80%, about 90%, or about 100%.

In some embodiments the carbon content of the graphite by weight is about 1% to about 100%. In some embodiments the carbon content of the graphite by weight is at least about 1%. In some embodiments the carbon content of the graphite by weight is at most about 100%. In some embodiments the carbon content of the graphite by weight is about 1% to about 5%, about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 100%, about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some embodiments the carbon content of the graphite by weight is about 1%, about 5%, about 10%, about 20%, about 30%, about 40%, about 50%, about 60%, about 70%, about 80%, about 90%, or about 100%. In some embodiments, the graphite has a grade or carbon content of less than about 100%, 99%, 98%, 97%, 96%, 95%, 94%, 93%, 92%, 91%, 90%, 85%, 80%, 70%, 60%, 50%, 40%, 30%, 20%, 15%, 10%, 5%, 2%, or 1% (e.g., by weight).

In some embodiments the mesh size of the graphite by weight is about 30 to about 500. In some embodiments the mesh size of the graphite by weight is at least about 30. In some embodiments the mesh size of the graphite by weight is at most about 500. In some embodiments the mesh size of the graphite by weight is about 30 to about 50, about 30 to about 75, about 30 to about 100, about 30 to about 150, about 30 to about 200, about 30 to about 250, about 30 to about 300, about 30 to about 350, about 30 to about 400, about 30 to about 450, about 30 to about 500, about 50 to about 75, about 50 to about 100, about 50 to about 150, about 50 to about 200, about 50 to about 250, about 50 to about 300, about 50 to about 350, about 50 to about 400, about 50 to about 450, about 50 to about 500, about 75 to about 100, about 75 to about 150, about 75 to about 200, about 75 to about 250, about 75 to about 300, about 75 to about 350, about 75 to about 400, about 75 to about 450, about 75 to about 500, about 100 to about 150, about 100 to about 200, about 100 to about 250, about 100 to about 300, about 100 to about 350, about 100 to about 400, about 100 to about 450, about 100 to about 500, about 150 to about 200, about 150 to about 250, about 150 to about 300, about 150 to about 350, about 150 to about 400, about 150 to about 450, about 150 to about 500, about 200 to about 250, about 200 to about 300, about 200 to about 350, about 200 to about 400, about 200 to about 450, about 200 to about 500, about 250 to about 300, about 250 to about 350, about 250 to about 400, about 250 to about 450, about 250 to about 500, about 300 to about 350, about 300 to about 400, about 300 to about 450, about 300 to about 500, about 350 to about 400, about 350 to about 450, about 350 to about 500, about 400 to about 450, about 400 to about 500, or about 450 to about 500. In some embodiments the mesh size of the graphite by weight is about 30, about 50, about 75, about 100, about 150, about 200, about 250, about 300, about 350, about 400, about 450, or about 500.

In some embodiments, $H_2SO_4$ (e.g., with a concentration of between about 96% $H_2SO_4$ and 98% $H_2SO_4$) may be provided in an amount between about 1 g graphite per 10 mL $H_2SO_4$ and 1 g graphite per 50 mL $H_2SO_4$. The method may include providing between about 10 mL $H_2SO_4$ and 20 mL $H_2SO_4$, 10 mL $H_2SO_4$ and 30 mL $H_2SO_4$, 10 mL $H_2SO_4$ and 40 mL $H_2SO_4$, 10 mL $H_2SO_4$ and 50 mL $H_2SO_4$, 20 mL $H_2SO_4$ and 30 mL $H_2SO_4$, 20 mL $H_2SO_4$ and 40 mL $H_2SO_4$, 20 mL $H_2SO_4$ and 50 mL $H_2SO_4$, 30 mL $H_2SO_4$ and 40 mL $H_2SO_4$, 30 mL $H_2SO_4$ and 50 mL $H_2SO_4$, or 40 mL $H_2SO_4$ and 50 mL $H_2SO_4$ per 1 g graphite. The method may include providing greater than or equal to about 10 mL $H_2SO_4$, 20 mL $H_2SO_4$, 30 mL $H_2SO_4$, 40 mL $H_2SO_4$, or 50 mL $H_2SO_4$ per 1 g graphite. The method may include providing less than about 75 mL $H_2SO_4$, 70 mL $H_2SO_4$, 60 mL $H_2SO_4$, 50 mL $H_2SO_4$, 40 mL $H_2SO_4$, 30 mL $H_2SO_4$, 20 mL $H_2SO_4$, or 15 mL $H_2SO_4$ per 1 g graphite.

In some embodiments, $H_2SO_4$ (e.g., with a concentration of between about 96% $H_2SO_4$ and 98% $H_2SO_4$) may be provided in an amount between about 1 g graphite per 18.4 g $H_2SO_4$ and about 1 g graphite per 92.0 g $H_2SO_4$. The method may include providing between about 18.4 g $H_2SO_4$ and 30 g $H_2SO_4$, 18.4 g $H_2SO_4$ and 40 g $H_2SO_4$, 18.4 g $H_2SO_4$ and 50 g $H_2SO_4$, 18.4 g $H_2SO_4$ and 60 g $H_2SO_4$, 18.4 g $H_2SO_4$ and 70 g $H_2SO_4$, 18.4 g $H_2SO_4$ and 80 g $H_2SO_4$, 18.4 g $H_2SO_4$ and 92.0 g $H_2SO_4$, 30 g $H_2SO_4$ and 40 g $H_2SO_4$, 30 g $H_2SO_4$ and 50 g $H_2SO_4$, 30 g $H_2SO_4$ and 60 g $H_2SO_4$, 30 g $H_2SO_4$ and 70 g $H_2SO_4$, 30 g $H_2SO_4$ and 80 g $H_2SO_4$, 30 g $H_2SO_4$ and 92.0 g $H_2SO_4$, 40 g $H_2SO_4$ and 50 g $H_2SO_4$, 30 g $H_2SO_4$ and 60 g $H_2SO_4$, 30 g $H_2SO_4$ and 70 g $H_2SO_4$, 30 g $H_2SO_4$ and 80 g $H_2SO_4$, 30 g $H_2SO_4$ and 92.0 g $H_2SO_4$, 40 g $H_2SO_4$ and 50 g $H_2SO_4$, 40 g $H_2SO_4$ and 60 g $H_2SO_4$, 40 g $H_2SO_4$ and 70 g $H_2SO_4$, 40 g $H_2SO_4$ and 80 g $H_2SO_4$, 40 g $H_2SO_4$ and 92.0 g $H_2SO_4$, 50 g $H_2SO_4$ and 60 g $H_2SO_4$, 50 g $H_2SO_4$ and 70 g $H_2SO_4$, 50 g $H_2SO_4$ and 80 g $H_2SO_4$, 50 g $H_2SO_4$ and 92.0 g $H_2SO_4$, 60 g $H_2SO_4$ and 70 g $H_2SO_4$, 60 g $H_2SO_4$ and 80 g $H_2SO_4$, 60 g $H_2SO_4$ and 92.0 g $H_2SO_4$, 70 g $H_2SO_4$ and 80 g $H_2SO_4$, 70 g $H_2SO_4$ and 92.0 g $H_2SO_4$, 80 g $H_2SO_4$ and 92.0 g $H_2SO_4$ per 1 g graphite. The method may include providing greater than or equal to about 18.4 g $H_2SO_4$, 20 g $H_2SO_4$, 25 g $H_2SO_4$, 30 g $H_2SO_4$, 35 g $H_2SO_4$, 40 g $H_2SO_4$, 45 g $H_2SO_4$, 50 g $H_2SO_4$, 55 g $H_2SO_4$, 60 g $H_2SO_4$, 65 g $H_2SO_4$, 70 g $H_2SO_4$, 75 g $H_2SO_4$, 80 g $H_2SO_4$, 85 g $H_2SO_4$, 90 g $H_2SO_4$, or 92.0 g $H_2SO_4$ per 1 g graphite. The method may include providing less than about 140 g $H_2SO_4$, 130 g $H_2SO_4$, 120 g $H_2SO_4$, 110 g $H_2SO_4$, 100 g $H_2SO_4$, 95 g $H_2SO_4$, 90 g $H_2SO_4$, 80 g $H_2SO_4$, 70 g $H_2SO_4$, 60 g $H_2SO_4$, 50 g $H_2SO_4$, 40 g $H_2SO_4$, 30 g $H_2SO_4$, or 20 g $H_2SO_4$ per 1 g graphite.

In some embodiments, $KMnO_4$ may be provided in an amount between about 1 g graphite: 2 g $KMnO_4$ and about 1 g graphite per 6 g $KMnO_4$. The method may include providing between about 1 g $KMnO_4$ and 2 g $KMnO_4$, 1 g $KMnO_4$ and 3 g $KMnO_4$, 1 g $KMnO_4$ and 4 g $KMnO_4$, 1 g $KMnO_4$ and 5 g $KMnO_4$, 1 g $KMnO_4$ and 6 g $KMnO_4$, 2 g $KMnO_4$ and 3 g $KMnO_4$, 2 g $KMnO_4$ and 4 g $KMnO_4$, 2 g $KMnO_4$ and 5 g $KMnO_4$, 2 g $KMnO_4$ and 6 g $KMnO_4$, 3 g $KMnO_4$ and 4 g $KMnO_4$, 3 g $KMnO_4$ and 5 g $KMnO_4$, 3 g $KMnO_4$ and 6 g $KMnO_4$, 4 g $KMnO_4$ and 5 g $KMnO_4$, 4 g $KMnO_4$ and 6 g $KMnO_4$, or 5 g $KMnO_4$ and 6 g $KMnO_4$ per 1 g graphite. The method may include providing greater than or equal to about 1 g $KMnO_4$, 2 g $KMnO_4$, 3 g $KMnO_4$, 4 g $KMnO_4$, 5 g $KMnO_4$, or 6 g $KMnO_4$ per 1 g graphite. The method may include providing less than about 9 g $KMnO_4$, 8 g $KMnO_4$, 7 g $KMnO_4$, 6 g $KMnO_4$, 5 g $KMnO_4$, 4 g $KMnO_4$, 3 g $KMnO_4$, or 2 g $KMnO_4$ per 1 g graphite.

In some embodiments, $H_2O_2$ may be provided in an amount of at least about 1 mol $H_2O_2$ per 1 mol $KMnO_4$. The method may include providing between about 1 mol $H_2O_2$ and 1.1 mol $H_2O_2$, 1 mol $H_2O_2$ and 1.2 mol $H_2O_2$, 1 mol $H_2O_2$ and 1.3 mol $H_2O_2$, 1 mol $H_2O_2$ and 1.4 mol $H_2O_2$, or 1 mol $H_2O_2$ and 1.5 mol $H_2O_2$ per 1 mol $KMnO_4$. The method may include providing greater than or equal to about 1 mol $H_2O_2$, 1.1 mol $H_2O_2$, 1.2 mol $H_2O_2$, 1.3 mol $H_2O_2$, 1.4 mol H$_2$O$_2$, or 1.5 mol H$_2$O$_2$ per 1 mol KMnO$_4$. The method may include providing less than about 1.5 mol H$_2$O$_2$, 1.4 mol H$_2$O$_2$, 1.3 mol H$_2$O$_2$, 1.2 mol H$_2$O$_2$, or 1.1 mol H$_2$O$_2$ per 1 mol KMnO$_4$.

In some embodiments, ice may be provided in an amount between about 1 g H$_2$SO$_4$:0 g ice and about 1 g H$_2$SO$_4$:1.09 g ice, between about 1 g H$_2$SO$_4$:1.09 g ice and about 1 g H$_2$SO$_4$:1.63 g ice, or between about 1 g H$_2$SO$_4$:0 g ice and about 1 g H$_2$SO$_4$:1.63 g ice. The method may include providing between about 0 g ice and 0.4 g ice, 0 g ice and 0.8 g ice, 0 g ice and 1.2 g ice, 0 g ice and 1.63 g ice, 0.4 g ice and 0.8 g ice, 0.4 g ice and 1.2 g ice, 0.4 g ice and 1.63 g ice, 0.8 g ice and 1.2 g ice, 0.8 g ice and 1.63 g ice, or 1.2 g ice and 1.63 g ice per 1 g H$_2$SO$_4$. The method may include providing greater than or equal to about 0 g ice, 0.2 g ice, 0.4 g ice, 0.6 g ice, 0.8 g ice, 1.09 g ice, 1.2 g ice, 1.4 g ice, or 1.63 g ice per 1 g H$_2$SO$_4$. The method may include providing less than about 2.4 g ice, 2.2 g ice, 2.0 g ice, 1.8 g ice, 1.63 g ice, 1.4 g ice, 1.2 g ice, 1.09 g ice, 0.8 g ice, 0.6 g ice, 0.4 g ice, 0.2 g ice, or 0.1 g ice per 1 g H$_2$SO$_4$.

In some embodiments, ice may be provided in an amount between about 1 mL H$_2$SO$_4$:0 g ice and about 1 mL H$_2$SO$_4$:2 g ice, between about 1 mL H$_2$SO$_4$:2 g ice and about 1 mL H$_2$SO$_4$:3 g ice, or between about 1 mL H$_2$SO$_4$:0 g ice and about 1 mL H$_2$SO$_4$:3 g ice. The method may include providing between about 0 g ice and 1 g ice, 0 g ice and 2 g ice, 0 g ice and 3 g ice, 1 g ice and 2 g ice, 1 g ice and 3 g ice, or 2 g ice and 3 g ice per 1 mL H$_2$SO$_4$. The method may include providing greater than or equal to about 0 g ice, 0.2 g ice, 0.4 g ice, 0.6 g ice, 0.8 g ice, 1 g ice, 1.2 g ice, 1.4 g ice, 1.6 g ice, 1.8 g ice, 2 g ice, 2.2 g ice, 2.4 g ice, 2.6 g ice, 2.8 g ice, or 3 g ice per 1 mL H$_2$SO$_4$. The method may include providing less than about 4.5 g ice, 4 g ice, 3.5 g ice, 3 g ice, 2.5 g ice, 2 g ice, 1.5 g ice, 1 g ice, 0.5 g ice, 0.25 g ice, or 0.1 g ice per 1 mL H$_2$SO$_4$.

In some embodiments, the ionic conductivity (e.g., for the method in FIG. 2) may be between about 10 microsiemens per centimeter (0/cm) and 20 µS/cm, 10 µS/cm and 30 µS/cm, 10 µS/cm and 40 µS/cm, 10 µS/cm and 50 µS/cm, 20 µS/cm and 30 µS/cm, 20 µS/cm and 40 µS/cm, 20 µS/cm and 50 µS/cm, 30 µS/cm and 40 µS/cm, 30 µS/cm and 50 µS/cm, or 40 µS/cm and 50 µS/cm. In some embodiments, the ionic conductivity (e.g., for the method in FIG. 2) may be less than and equal to about 50 µS/cm, 40 µS/cm, 30 µS/cm, 20 µS/cm, or 10 µS/cm. In some embodiments, the given purity or grade may be achieved at least about 2, 3, 4, 5, 6, 7, 8, 9, or 10 times faster than a Hummers-based method. In some embodiments, the given purity or grade may be achieved between about 2 and 5, 2 and 8, or 5 and 8 times faster than a Hummers-based method. In some instances, the purity or grade may be reached at the aforementioned faster rates because a Hummers-based method requires hydrochloric acid to be washed out and is therefore slower to reach the given purity or grade. A reduced graphite oxide (e.g., graphene or ICCN) synthesis method of the present disclosure may be used to form (e.g., from graphite oxide produced in accordance with the present disclosure) reduced graphite oxide (e.g., graphene or ICCN) with a given purity or grade (e.g., a minimum purity or grade). In some embodiments, a purity or grade of a rCBO (e.g., reduced graphite oxide) may be at least about 90%, 95%, 96%, 97%, 98%, 99%, 99.5%, or 99.9% carbon (e.g., by weight). In other embodiments, the purity or grade of the rCBO by weight is between at least 90% and 95%, and between at least 95% and 99.9%.

One embodiment described herein is a method for producing a carbon-based oxide material comprising: forming a first solution comprising graphite and an acid; cooling the first solution to a first temperature; adding a first oxidizing agent to the first solution to form a second solution; and quenching the second solution to a second temperature to form a carbon-based oxide material.

In some embodiments the graphite comprises graphite powder, graphite flakes, milled graphite, exfoliated graphite, amorphous graphite, vein graphite, or any combination thereof.

In some embodiments the graphite has a carbon content by weight of about 1% to about 100%. In some embodiments the graphite has a carbon content by weight of at least about 1%. In some embodiments the graphite has a carbon content by weight of at most about 100%. In some embodiments the graphite has a carbon content by weight of about 1% to about 2%, about 1% to about 5%, about 1% to about 10%, about 1% to about 20%, about 1% to about 30%, about 1% to about 40%, about 1% to about 50%, about 1% to about 60%, about 1% to about 80%, about 1% to about 99%, about 1% to about 100%, about 2% to about 5%, about 2% to about 10%, about 2% to about 20%, about 2% to about 30%, about 2% to about 40%, about 2% to about 50%, about 2% to about 60%, about 2% to about 80%, about 2% to about 99%, about 2% to about 100%, about 5% to about 10%, about 5% to about 20%, about 5% to about 30%, about 5% to about 40%, about 5% to about 50%, about 5% to about 60%, about 5% to about 80%, about 5% to about 99%, about 5% to about 100%, about 10% to about 20%, about 10% to about 30%, about 10% to about 40%, about 10% to about 50%, about 10% to about 60%, about 10% to about 80%, about 10% to about 99%, about 10% to about 100%, about 20% to about 30%, about 20% to about 40%, about 20% to about 50%, about 20% to about 60%, about 20% to about 80%, about 20% to about 99%, about 20% to about 100%, about 30% to about 40%, about 30% to about 50%, about 30% to about 60%, about 30% to about 80%, about 30% to about 99%, about 30% to about 100%, about 40% to about 50%, about 40% to about 60%, about 40% to about 80%, about 40% to about 99%, about 40% to about 100%, about 50% to about 60%, about 50% to about 80%, about 50% to about 99%, about 50% to about 100%, about 60% to about 80%, about 60% to about 99%, about 60% to about 100%, about 80% to about 99%, about 80% to about 100%, or about 99% to about 100%. In some embodiments the graphite has a carbon content by weight of about 1%, about 2%, about 5%, about 10%, about 20%, about 30%, about 40%, about 50%, about 60%, about 80%, about 99%, or about 100%.

In some embodiments the graphite has an ionic conductivity of about 1 µS/cm to about 100 µS/cm. In some embodiments the graphite has an ionic conductivity of at least about 1 µS/cm. In some embodiments the graphite has an ionic conductivity of at most about 100 µS/cm. In some embodiments the graphite has an ionic conductivity of about 1 µS/cm to about 2 µS/cm, about 1 µS/cm to about 5 µS/cm, about 1 µS/cm to about 10 µS/cm, about 1 µS/cm to about 20 µS/cm, about 1 µS/cm to about 30 µS/cm, about 1 µS/cm to about 40 µS/cm, about 1 µS/cm to about 50 µS/cm, about 1 µS/cm to about 60 µS/cm, about 1 µS/cm to about 80 µS/cm, about 1 µS/cm to about 99 µS/cm, about 1 µS/cm to about 100 µS/cm, about 2 µS/cm to about 5 µS/cm, about 2 µS/cm to about 10 µS/cm, about 2 µS/cm to about 20 µS/cm, about 2 µS/cm to about 30 µS/cm, about 2 µS/cm to about 40 µS/cm, about 2 µS/cm to about 50 µS/cm, about 2 µS/cm to about 60 µS/cm, about 2 µS/cm to about 80 µS/cm, about 2 µS/cm to about 99 µS/cm, about 2 µS/cm to about 100 µS/cm, about 5 µS/cm to about 10 µS/cm, about 5 µS/cm to about 20 µS/cm, about 5 µS/cm to about 30 µS/cm, about 5

μS/cm to about 40 μS/cm, about 5 μS/cm to about 50 μS/cm, about 5 μS/cm to about 60 μS/cm, about 5 μS/cm to about 80 μS/cm, about 5 μS/cm to about 99 μS/cm, about 5 μS/cm to about 100 μS/cm, about 10 μS/cm to about 20 μS/cm, about 10 μS/cm to about 30 μS/cm, about 10 μS/cm to about 40 μS/cm, about 10 μS/cm to about 50 μS/cm, about 10 μS/cm to about 60 μS/cm, about 10 μS/cm to about 80 μS/cm, about 10 μS/cm to about 99 μS/cm, about 10 μS/cm to about 100 μS/cm, about 20 μS/cm to about 30 μS/cm, about 20 μS/cm to about 40 μS/cm, about 20 μS/cm to about 50 μS/cm, about 20 μS/cm to about 60 μS/cm, about 20 μS/cm to about 80 μS/cm, about 20 μS/cm to about 99 μS/cm, about 20 μS/cm to about 100 μS/cm, about 30 μS/cm to about 40 μS/cm, about 30 μS/cm to about 50 μS/cm, about 30 μS/cm to about 60 μS/cm, about 30 μS/cm to about 80 μS/cm, about 30 μS/cm to about 99 μS/cm, about 30 μS/cm to about 100 μS/cm, about 40 μS/cm to about 50 μS/cm, about 40 μS/cm to about 60 μS/cm, about 40 μS/cm to about 80 μS/cm, about 40 μS/cm to about 99 μS/cm, about 40 μS/cm to about 100 μS/cm, about 50 μS/cm to about 60 μS/cm, about 50 μS/cm to about 80 μS/cm, about 50 μS/cm to about 99 μS/cm, about 50 μS/cm to about 100 μS/cm, about 60 μS/cm to about 80 μS/cm, about 60 μS/cm to about 99 μS/cm, about 60 μS/cm to about 100 μS/cm, about 80 μS/cm to about 99 μS/cm, about 80 μS/cm to about 100 μS/cm, or about 99 μS/cm to about 100 μS/cm. In some embodiments the graphite has an ionic conductivity of about 1 μS/cm, about 2 μS/cm, about 5 μS/cm, about 10 μS/cm, about 20 μS/cm, about 30 μS/cm, about 40 μS/cm, about 50 μS/cm, about 60 μS/cm, about 80 μS/cm, about 99 μS/cm, or about 100 μS/cm. In some embodiments the graphite has an ionic conductivity of at least about 1 μS/cm, at least about 2 μS/cm, at least about 5 μS/cm, at least about 10 μS/cm, at least about 20 μS/cm, at least about 30 μS/cm, at least about 40 μS/cm, at least about 50 μS/cm, at least about 60 μS/cm, at least about 80 μS/cm, at least about 99 μS/cm, or at least about 100 μS/cm.

In some embodiments the mass of the first oxidizing agent is greater than the mass of the graphite by a factor of about −200 to about 200. In some embodiments the mass of the first oxidizing agent is greater than the mass of the graphite by a factor of at least about −200. In some embodiments the mass of the first oxidizing agent is greater than the mass of the graphite by a factor of at most about 200. In some embodiments the mass of the first oxidizing agent is greater than the mass of the graphite by a factor of about −200 to about −150, about −200 to about −100, about −200 to about −50, about −200 to about 0, about −200 to about 50, about −200 to about 100, about −200 to about 150, about −200 to about 200, about −150 to about −100, about −150 to about −50, about −150 to about 0, about −150 to about 50, about −150 to about 100, about −150 to about 150, about −150 to about 200, about −100 to about −50, about −100 to about 0, about −100 to about 50, about −100 to about 100, about −100 to about 150, about −100 to about 200, about −50 to about 0, about −50 to about 50, about −50 to about 100, about −50 to about 150, about −50 to about 200, about 0 to about 50, about 0 to about 100, about 0 to about 150, about 0 to about 200, about 50 to about 100, about 50 to about 150, about 50 to about 200, about 100 to about 150, about 100 to about 200, or about 150 to about 200. In some embodiments the mass of the first oxidizing agent is greater than the mass of the graphite by a factor of about −200, about −150, about −100, about −50, about 0, about 50, about 100, about 150, or about 200.

In some embodiments the acid comprises a strong acid. In some embodiments the strong acid comprises perchloric acid, hydroiodic acid, hydrobromic acid, hydrochloric acid, sulfuric acid, p-toluenesulfonic acid methanesulfonic acid, or any combination thereof.

In some embodiments the mass of the acid is greater than the mass of the graphite by a factor of about 30 to about 80. In some embodiments the mass of the acid is greater than the mass of the graphite by a factor of at least about 30. In some embodiments the mass of the acid is greater than the mass of the graphite by a factor of at most about 80. In some embodiments the mass of the acid is greater than the mass of the graphite by a factor of about 30 to about 35, about 30 to about 40, about 30 to about 45, about 30 to about 50, about 30 to about 55, about 30 to about 60, about 30 to about 65, about 30 to about 70, about 30 to about 75, about 30 to about 80, about 35 to about 40, about 35 to about 45, about 35 to about 50, about 35 to about 55, about 35 to about 60, about 35 to about 65, about 35 to about 70, about 35 to about 75, about 35 to about 80, about 40 to about 45, about 40 to about 50, about 40 to about 55, about 40 to about 60, about 40 to about 65, about 40 to about 70, about 40 to about 75, about 40 to about 80, about 45 to about 50, about 45 to about 55, about 45 to about 60, about 45 to about 65, about 45 to about 70, about 45 to about 75, about 45 to about 80, about 50 to about 55, about 50 to about 60, about 50 to about 65, about 50 to about 70, about 50 to about 75, about 50 to about 80, about 55 to about 60, about 55 to about 65, about 55 to about 70, about 55 to about 75, about 55 to about 80, about 60 to about 65, about 60 to about 70, about 60 to about 75, about 60 to about 80, about 65 to about 70, about 65 to about 75, about 65 to about 80, about 70 to about 75, about 70 to about 80, or about 75 to about 80. In some embodiments the mass of the acid is greater than the mass of the graphite by a factor of about 30, about 35, about 40, about 45, about 50, about 55, about 60, about 65, about 70, about 75, or about 80.

In some embodiments the concentration of the acid is about 90% to about 99%. In some embodiments the concentration of the acid is at least about 90%. In some embodiments the concentration of the acid is at most about 99%. In some embodiments the concentration of the acid is about 90% to about 91%, about 90% to about 92%, about 90% to about 93%, about 90% to about 94%, about 90% to about 95%, about 90% to about 96%, about 90% to about 97%, about 90% to about 98%, about 90% to about 99%, about 91% to about 92%, about 91% to about 93%, about 91% to about 94%, about 91% to about 95%, about 91% to about 96%, about 91% to about 97%, about 91% to about 98%, about 91% to about 99%, about 92% to about 93%, about 92% to about 94%, about 92% to about 95%, about 92% to about 96%, about 92% to about 97%, about 92% to about 98%, about 92% to about 99%, about 93% to about 94%, about 93% to about 95%, about 93% to about 96%, about 93% to about 97%, about 93% to about 98%, about 93% to about 99%, about 94% to about 95%, about 94% to about 96%, about 94% to about 97%, about 94% to about 98%, about 94% to about 99%, about 95% to about 96%, about 95% to about 97%, about 95% to about 98%, about 95% to about 99%, about 96% to about 97%, about 96% to about 98%, about 96% to about 99%, about 97% to about 98%, about 97% to about 99%, or about 98% to about 99%. In some embodiments the concentration of the acid is about 90%, about 91%, about 92%, about 93%, about 94%, about 95%, about 96%, about 97%, about 98%, or about 99%.

In some embodiments the first temperature is about −20° C. to about 30° C. In some embodiments the first temperature is at least about −20° C. In some embodiments the first temperature is at most about 30° C. In some embodiments the first temperature is at most about 25° C. In some embodiments the first temperature is at most about 20° C. In some embodiments the first temperature is at most about 15° C. In some embodiments the first temperature is about −20° C. to about −15° C., about −20° C. to about −5° C., about −20° C. to about −10° C., about −20° C. to about 0° C., about −20° C. to about 5° C., about −20° C. to about 10° C., about −20° C. to about 15° C., about −20° C. to about 20° C., about −20° C. to about 25° C., about −20° C. to about 30° C., about −15° C. to about −5° C., about −15° C. to about −10° C., about −15° C. to about 0° C., about −15° C. to about 5° C., about −15° C. to about 10° C., about −15° C. to about 15° C., about −15° C. to about 20° C., about −15° C. to about 25° C., about −15° C. to about 30° C., about −5° C. to about −10° C., about −5° C. to about 0° C., about −5° C. to about 5° C., about −5° C. to about 10° C., about −5° C. to about 15° C., about −5° C. to about 20° C., about −5° C. to about 25° C., about −5° C. to about 30° C., about −10° C. to about 0° C., about −10° C. to about 5° C., about −10° C. to about 10° C., about −10° C. to about 15° C., about −10° C. to about 20° C., about −10° C. to about 25° C., about −10° C. to about 30° C., about 0° C. to about 5° C., about 0° C. to about 10° C., about 0° C. to about 15° C., about 0° C. to about 20° C., about 0° C. to about 25° C., about 0° C. to about 30° C., about 5° C. to about 10° C., about 5° C. to about 15° C., about 5° C. to about 20° C., about 5° C. to about 25° C., about 5° C. to about 30° C., about 10° C. to about 15° C., about 10° C. to about 20° C., about 10° C. to about 25° C., about 10° C. to about 30° C., about 15° C. to about 20° C., about 15° C. to about 25° C., about 15° C. to about 30° C., about 20° C. to about 25° C., about 20° C. to about 30° C., or about 25° C. to about 30° C. In some embodiments the first temperature is about −20° C., about −15° C., about −5° C., about −10° C., about 0° C., about 5° C., about 10° C., about 15° C., about 20° C., about 25° C., or about 30° C.

In some embodiments the first solution is cooled to the first temperature. In some embodiments the first solution is cooled to the first temperature, by an ice bath, a water bath, one or more cooling coils, ice, water, or any combination thereof.

In some embodiments the first oxidizing agent comprises oxygen, ozone, hydrogen peroxide, fluorite dioxide, lithium peroxide, barium peroxide, fluorine, chlorine, nitric acid, nitrate compounds, sulfuric acid, peroxydisulfuric acid, peroxymonosulfuric acid, chlorite, chlorate, perchlorate, halogen compounds hypochlorite, hypohalite compounds, household bleach, hexavalent chromium compounds, chromic acids, dichromic acids, chromium trioxide, pyridinium chlorochromate, chromate compounds, dichromate compounds, permanganate compounds, potassium permanganate, sodium perborate, nitrous oxide, potassium nitrate, sodium bismuthate, or any combination thereof.

In some embodiments the mass of the first oxidizing agent is greater than the mass of the graphite by a factor of about 1.5 to about 12. In some embodiments the mass of the first oxidizing agent is greater than the mass of the graphite by a factor of at least about 1.5. In some embodiments the mass of the first oxidizing agent is greater than the mass of the graphite by a factor of at most about 12. In some embodiments the mass of the first oxidizing agent is greater than the mass of the graphite by a factor of about 1.5 to about 2, about 1.5 to about 3, about 1.5 to about 4, about 1.5 to about 5, about 1.5 to about 6, about 1.5 to about 7, about 1.5 to about 8, about 1.5 to about 9, about 1.5 to about 10, about 1.5 to about 11, about 1.5 to about 12, about 2 to about 3, about 2 to about 4, about 2 to about 5, about 2 to about 6, about 2 to about 7, about 2 to about 8, about 2 to about 9, about 2 to about 10, about 2 to about 11, about 2 to about 12, about 3 to about 4, about 3 to about 5, about 3 to about 6, about 3 to about 7, about 3 to about 8, about 3 to about 9, about 3 to about 10, about 3 to about 11, about 3 to about 12, about 4 to about 5, about 4 to about 6, about 4 to about 7, about 4 to about 8, about 4 to about 9, about 4 to about 10, about 4 to about 11, about 4 to about 12, about 5 to about 6, about 5 to about 7, about 5 to about 8, about 5 to about 9, about 5 to about 10, about 5 to about 11, about 5 to about 12, about 6 to about 7, about 6 to about 8, about 6 to about 9, about 6 to about 10, about 6 to about 11, about 6 to about 12, about 7 to about 8, about 7 to about 9, about 7 to about 10, about 7 to about 11, about 7 to about 12, about 8 to about 9, about 8 to about 10, about 8 to about 11, about 8 to about 12, about 9 to about 10, about 9 to about 11, about 9 to about 12, about 10 to about 11, about 10 to about 12, or about 11 to about 12. In some embodiments the mass of the first oxidizing agent is greater than the mass of the graphite by a factor of about 1.5, about 2, about 3, about 4, about 5, about 6, about 7, about 8, about 9, about 10, about 11, or about 12.

In some embodiments the first oxidizing agent is added to the first solution over a period of time of about 15 minutes to about 180 minutes. In some embodiments the first oxidizing agent is added to the first solution over a period of time of at least about 15 minutes. In some embodiments the first oxidizing agent is added to the first solution over a period of time of at most about 180 minutes. In some embodiments the first oxidizing agent is added to the first solution over a period of time of about 15 minutes to about 30 minutes, about 15 minutes to about 45 minutes, about 15 minutes to about 60 minutes, about 15 minutes to about 75 minutes, about 15 minutes to about 90 minutes, about 15 minutes to about 105 minutes, about 15 minutes to about 120 minutes, about 15 minutes to about 135 minutes, about 15 minutes to about 150 minutes, about 15 minutes to about 180 minutes, about 30 minutes to about 45 minutes, about 30 minutes to about 60 minutes, about 30 minutes to about 75 minutes, about 30 minutes to about 90 minutes, about 30 minutes to about 105 minutes, about 30 minutes to about 120 minutes, about 30 minutes to about 135 minutes, about 30 minutes to about 150 minutes, about 30 minutes to about 180 minutes, about 45 minutes to about 60 minutes, about 45 minutes to about 75 minutes, about 45 minutes to about 90 minutes, about 45 minutes to about 105 minutes, about 45 minutes to about 120 minutes, about 45 minutes to about 135 minutes, about 45 minutes to about 150 minutes, about 45 minutes to about 180 minutes, about 60 minutes to about 75 minutes, about 60 minutes to about 90 minutes, about 60 minutes to about 105 minutes, about 60 minutes to about 120 minutes, about 60 minutes to about 135 minutes, about 60 minutes to about 150 minutes, about 60 minutes to about 180 minutes, about 75 minutes to about 90 minutes, about 75 minutes to about 105 minutes, about 75 minutes to about 120 minutes, about 75 minutes to about 135 minutes, about 75 minutes to about 150 minutes, about 75 minutes to about 180 minutes, about 90 minutes to about 105 minutes, about 90 minutes to about 120 minutes, about 90 minutes to about 135 minutes, about 90 minutes to about 150 minutes, about 90 minutes to about 180 minutes, about 105 minutes to about 120 minutes, about 105 minutes to about 135 minutes, about 105 minutes to about 150 minutes, about 105 minutes to about 180 minutes, about 120 minutes to about 135 minutes, about 120 minutes to about 150 minutes, about 120 minutes to about 180 minutes, about 135 minutes to about 150 minutes, about 135 minutes to about 180 minutes, or about 150 minutes to about 180 minutes. In some embodiments the first oxidizing agent is added to the first solution over a period of time of about 15 minutes, about 30 minutes, about 45 minutes, about 60 minutes, about 75 minutes, about 90 minutes, about 105 minutes, about 120 minutes, about 135 minutes, about 150 minutes, or about 180 minutes. In some embodiments the first oxidizing agent is added to the first solution over a period of time of at least about 15 minutes, at least about 30 minutes, at least about 45 minutes, at least about 60 minutes, at least about 75 minutes, at least about 90 minutes, at least about 105 minutes, at least about 120 minutes, at least about 135 minutes, at least about 150 minutes, or at least about 180 minutes. In some embodiments the first oxidizing agent is added to the first solution over a period of time of at most about 15 minutes, at most about 30 minutes, at most about 45 minutes, at most about 60 minutes, at most about 75 minutes, at most about 90 minutes, at most about 105 minutes, at most about 120 minutes, at most about 135 minutes, at most about 150 minutes, or at most about 180 minutes.

In some embodiments a temperature of the second solution during the addition of the first oxidizing agent is less than about 30° C., less than about 27° C., less than about 24° C., less than about 21° C., less than about 18° C., less than about 15° C., or less than about 12° C.

Some embodiments further comprise allowing the second solution to react at a third temperature over a first period of time.

In some embodiments the third temperature is about 10° C. to about 70° C. In some embodiments the third temperature is at least about 10° C. In some embodiments the third temperature is at most about 70° C. In some embodiments the third temperature is about 10° C. to about 15° C., about 10° C. to about 20° C., about 10° C. to about 25° C., about 10° C. to about 30° C., about 10° C. to about 35° C., about 10° C. to about 40° C., about 10° C. to about 45° C., about 10° C. to about 50° C., about 10° C. to about 55° C., about 10° C. to about 60° C., about 10° C. to about 70° C., about 15° C. to about 20° C., about 15° C. to about 25° C., about 15° C. to about 30° C., about 15° C. to about 35° C., about 15° C. to about 40° C., about 15° C. to about 45° C., about 15° C. to about 50° C., about 15° C. to about 55° C., about 15° C. to about 60° C., about 15° C. to about 70° C., about 20° C. to about 25° C., about 20° C. to about 30° C., about 20° C. to about 35° C., about 20° C. to about 40° C., about 20° C. to about 45° C., about 20° C. to about 50° C., about 20° C. to about 55° C., about 20° C. to about 60° C., about 20° C. to about 70° C., about 25° C. to about 30° C., about 25° C. to about 35° C., about 25° C. to about 40° C., about 25° C. to about 45° C., about 25° C. to about 50° C., about 25° C. to about 55° C., about 25° C. to about 60° C., about 25° C. to about 70° C., about 30° C. to about 35° C., about 30° C. to about 40° C., about 30° C. to about 45° C., about 30° C. to about 50° C., about 30° C. to about 55° C., about 30° C. to about 60° C., about 30° C. to about 70° C., about 35° C. to about 40° C., about 35° C. to about 45° C., about 35° C. to about 50° C., about 35° C. to about 55° C., about 35° C. to about 60° C., about 35° C. to about 70° C., about 40° C. to about 45° C., about 40° C. to about 50° C., about 40° C. to about 55° C., about 40° C. to about 60° C., about 40° C. to about 70° C., about 45° C. to about 50° C., about 45° C. to about 55° C., about 45° C. to about 60° C., about 45° C. to about 70° C., about 50° C. to about 55° C., about 50° C. to about 60° C., about 50° C. to about 70° C., about 55° C. to about 60° C., about 55° C. to about 70° C., or about 60° C. to about 70° C. In some embodiments the third temperature is about 10° C., about 15° C., about 20° C., about 25° C., about 30° C., about 35° C., about 40° C., about 45° C., about 50° C., about 55° C., about 60° C., or about 70° C. In some embodiments the third temperature is at most about 10° C., at most about 15° C., at most about 20° C., at most about 25° C., at most about 30° C., at most about 35° C., at most about 40° C., at most about 45° C., at most about 50° C., at most about 55° C., at most about 60° C., or at most about 70° C.

In some embodiments the first period of time is about 15 minutes to about 120 minutes. In some embodiments the first period of time is at least about 15 minutes. In some embodiments the first period of time is at most about 120 minutes. In some embodiments the first period of time is about 15 minutes to about 30 minutes, about 15 minutes to about 45 minutes, about 15 minutes to about 60 minutes, about 15 minutes to about 75 minutes, about 15 minutes to about 90 minutes, about 15 minutes to about 120 minutes, about 30 minutes to about 45 minutes, about 30 minutes to about 60 minutes, about 30 minutes to about 75 minutes, about 30 minutes to about 90 minutes, about 30 minutes to about 120 minutes, about 45 minutes to about 60 minutes, about 45 minutes to about 75 minutes, about 45 minutes to about 90 minutes, about 45 minutes to about 120 minutes, about 60 minutes to about 75 minutes, about 60 minutes to about 90 minutes, about 60 minutes to about 120 minutes, about 75 minutes to about 90 minutes, about 75 minutes to about 120 minutes, or about 90 minutes to about 120 minutes. In some embodiments the first period of time is about 15 minutes, about 30 minutes, about 45 minutes, about 60 minutes, about 75 minutes, about 90 minutes, or about 120 minutes.

In some embodiments the second solution is quenched to the second temperature. In some embodiments the second solution is quenched to the second temperature by an ice bath, a water bath, one or more cooling coils, ice, water, or any combination thereof. In some embodiments quenching the second solution further comprises adding a second oxidizing agent to the second solution.

In some embodiments the second temperature is about 25° C. to about 75° C. In some embodiments the second temperature is at least about 25° C. In some embodiments the second temperature is at most about 75° C. In some embodiments the second temperature is about 25° C. to about 30° C., about 25° C. to about 35° C., about 25° C. to about 40° C., about 25° C. to about 45° C., about 25° C. to about 50° C., about 25° C. to about 55° C., about 25° C. to about 60° C., about 25° C. to about 65° C., about 25° C. to about 70° C., about 25° C. to about 75° C., about 30° C. to about 35° C., about 30° C. to about 40° C., about 30° C. to about 45° C., about 30° C. to about 50° C., about 30° C. to about 55° C., about 30° C. to about 60° C., about 30° C. to about 65° C., about 30° C. to about 70° C., about 30° C. to about 75° C., about 35° C. to about 40° C., about 35° C. to about 45° C., about 35° C. to about 50° C., about 35° C. to about 55° C., about 35° C. to about 60° C., about 35° C. to about 65° C., about 35° C. to about 70° C., about 35° C. to about 75° C., about 40° C. to about 45° C., about 40° C. to about 50° C., about 40° C. to about 55° C., about 40° C. to about 60° C., about 40° C. to about 65° C., about 40° C. to about 70° C., about 40° C. to about 75° C., about 45° C. to about 50° C., about 45° C. to about 55° C., about 45° C. to about 60° C., about 45° C. to about 65° C., about 45° C. to about 70° C., about 45° C. to about 75° C., about 50° C. to about 55° C., about 50° C. to about 60° C., about 50° C. to about 65° C., about 50° C. to about 70° C., about 50° C. to about 75° C., about 55° C. to about 60° C., about 55° C. to about 65° C., about 55° C. to about 70° C., about 55° C. to about 75° C., about 60° C. to about 65° C., about 60° C. to about 70° C., about 60° C. to about 75° C., about 65° C. to about 70° C., about 65° C. to about 75° C., or about 70° C. to about 75°

C. In some embodiments the second temperature is about 25° C., about 30° C., about 35° C., about 40° C., about 45° C., about 50° C., about 55° C., about 60° C., about 65° C., about 70° C., or about 75° C. In some embodiments the second temperature is at most about 25° C., at most about 30° C., at most about 35° C., at most about 40° C., at most about 45° C., at most about 50° C., at most about 55° C., at most about 60° C., at most about 65° C., at most about 70° C., or at most about 75° C.

In some embodiments quenching the second solution occurs over a period of time of about 30 minutes to about 120 minutes. In some embodiments quenching the second solution occurs over a period of time of at least about 30 minutes. In some embodiments quenching the second solution occurs over a period of time of at most about 120 minutes. In some embodiments quenching the second solution occurs over a period of time of about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 40 minutes to about 50 minutes, about 40 minutes to about 60 minutes, about 40 minutes to about 70 minutes, about 40 minutes to about 80 minutes, about 40 minutes to about 90 minutes, about 40 minutes to about 100 minutes, about 40 minutes to about 110 minutes, about 40 minutes to about 120 minutes, about 50 minutes to about 60 minutes, about 50 minutes to about 70 minutes, about 50 minutes to about 80 minutes, about 50 minutes to about 90 minutes, about 50 minutes to about 100 minutes, about 50 minutes to about 110 minutes, about 50 minutes to about 120 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 70 minutes to about 80 minutes, about 70 minutes to about 90 minutes, about 70 minutes to about 100 minutes, about 70 minutes to about 110 minutes, about 70 minutes to about 120 minutes, about 80 minutes to about 90 minutes, about 80 minutes to about 100 minutes, about 80 minutes to about 110 minutes, about 80 minutes to about 120 minutes, about 90 minutes to about 100 minutes, about 90 minutes to about 110 minutes, about 90 minutes to about 120 minutes, about 100 minutes to about 110 minutes, about 100 minutes to about 120 minutes, or about 110 minutes to about 120 minutes. In some embodiments quenching the second solution occurs over a period of time of about 30 minutes, about 40 minutes, about 50 minutes, about 60 minutes, about 70 minutes, about 80 minutes, about 90 minutes, about 100 minutes, about 110 minutes, or about 120 minutes.

In some embodiments the second oxidizing agent comprises oxygen, ozone, hydrogen peroxide, fluorite dioxide, lithium peroxide, barium peroxide, fluorine, chlorine, nitric acid, nitrate compounds, sulfuric acid, peroxydisulfuric acid, peroxymonosulfuric acid, chlorite, chlorate, perchlorate, halogen compounds hypochlorite, hypohalite compounds, household bleach, hexavalent chromium compounds, chromic acids, dichromic acids, chromium trioxide, pyridinium chlorochromate, chromate compounds, dichromate compounds, permanganate compounds, potassium permanganate, sodium perborate, nitrous oxide, potassium nitrate, sodium bismuthate or any combination thereof.

In some embodiments a mass of the second oxidizing agent is greater than the mass of the graphite by a factor of about 1.5 to about 6. In some embodiments a mass of the second oxidizing agent is greater than the mass of the graphite by a factor of at least about 1.5. In some embodiments a mass of the second oxidizing agent is greater than the mass of the graphite by a factor of at most about 6. In some embodiments a mass of the second oxidizing agent is greater than the mass of the graphite by a factor of about 1.5 to about 2, about 1.5 to about 2.5, about 1.5 to about 3, about 1.5 to about 3.5, about 1.5 to about 4, about 1.5 to about 4.5, about 1.5 to about 5, about 1.5 to about 5.5, about 1.5 to about 6, about 2 to about 2.5, about 2 to about 3, about 2 to about 3.5, about 2 to about 4, about 2 to about 4.5, about 2 to about 5, about 2 to about 5.5, about 2 to about 6, about 2.5 to about 3, about 2.5 to about 3.5, about 2.5 to about 4, about 2.5 to about 4.5, about 2.5 to about 5, about 2.5 to about 5.5, about 2.5 to about 6, about 3 to about 3.5, about 3 to about 4, about 3 to about 4.5, about 3 to about 5, about 3 to about 5.5, about 3 to about 6, about 3.5 to about 4, about 3.5 to about 4.5, about 3.5 to about 5, about 3.5 to about 5.5, about 3.5 to about 6, about 4 to about 4.5, about 4 to about 5, about 4 to about 5.5, about 4 to about 6, about 4.5 to about 5, about 4.5 to about 5.5, about 4.5 to about 6, about 5 to about 5.5, about 5 to about 6, or about 5.5 to about 6. In some embodiments a mass of the second oxidizing agent is greater than the mass of the graphite by a factor of about 1.5, about 2, about 2.5, about 3, about 3.5, about 4, about 4.5, about 5, about 5.5, or about 6.

Some embodiments further comprise agitating at least one of the first solution, and the second solution for a period of time, and the carbon-based oxide material.

In some embodiments the agitation occurs for a period of time of about 45 minutes to about 360 minutes. In some embodiments the agitation occurs for a period of time of at least about 45 minutes. In some embodiments the agitation occurs for a period of time of at most about 360 minutes. In some embodiments the agitation occurs for a period of time of about 45 minutes to about 60 minutes, about 45 minutes to about 75 minutes, about 45 minutes to about 90 minutes, about 45 minutes to about 120 minutes, about 45 minutes to about 150 minutes, about 45 minutes to about 180 minutes, about 45 minutes to about 210 minutes, about 45 minutes to about 240 minutes, about 45 minutes to about 280 minutes, about 45 minutes to about 320 minutes, about 45 minutes to about 360 minutes, about 60 minutes to about 75 minutes, about 60 minutes to about 90 minutes, about 60 minutes to about 120 minutes, about 60 minutes to about 150 minutes, about 60 minutes to about 180 minutes, about 60 minutes to about 210 minutes, about 60 minutes to about 240 minutes, about 60 minutes to about 280 minutes, about 60 minutes to about 320 minutes, about 60 minutes to about 360 minutes, about 75 minutes to about 90 minutes, about 75 minutes to about 120 minutes, about 75 minutes to about 150 minutes, about 75 minutes to about 180 minutes, about 75 minutes to about 210 minutes, about 75 minutes to about 240 minutes, about 75 minutes to about 280 minutes, about 75 minutes to about 320 minutes, about 75 minutes to about 360 minutes, about 90 minutes to about 120 minutes, about 90 minutes to about 150 minutes, about 90 minutes to about 180 minutes, about 90 minutes to about 210 minutes, about 90 minutes to about 240 minutes, about 90 minutes to about 280 minutes, about 90 minutes to about 320 minutes, about 90 minutes to about 360 minutes, about 120 minutes to about 150 minutes, about 120 minutes to about 180 minutes, about 120 minutes to about 210 minutes, about 120 minutes to about 240 minutes, about 120 minutes to about 280 minutes, about 120 minutes to about 320 minutes, about 120 minutes to about 360 minutes, about 150 minutes to about 180 minutes, about 150 minutes to about 210 minutes, about 150 minutes to about 240 minutes, about 150 minutes to about 280 minutes, about 150 minutes to about 320 minutes, about 150 minutes to about 360 minutes, about 180 minutes to about 210 minutes, about 180 minutes to about 240 minutes, about 180 minutes to about 280 minutes, about 180 minutes to about 320 minutes, about 180 minutes to about 360 minutes, about 210 minutes to about 240 minutes, about 210 minutes to about 280 minutes, about 210 minutes to about 320 minutes, about 210 minutes to about 360 minutes, about 240 minutes to about 280 minutes, about 240 minutes to about 320 minutes, about 240 minutes to about 360 minutes, about 280 minutes to about 320 minutes, about 280 minutes to about 360 minutes, or about 320 minutes to about 360 minutes. In some embodiments the agitation occurs for a period of time of about 45 minutes, about 60 minutes, about 75 minutes, about 90 minutes, about 120 minutes, about 150 minutes, about 180 minutes, about 210 minutes, about 240 minutes, about 280 minutes, about 320 minutes, or about 360 minutes.

In some embodiments the agitation occurs at a stirring rate of about 10 rpm to about 300 rpm. In some embodiments the agitation occurs at a stirring rate of at least about 10 rpm. In some embodiments the agitation occurs at a stirring rate of at most about 300 rpm. In some embodiments the agitation occurs at a stirring rate of about 10 rpm to about 20 rpm, about 10 rpm to about 50 rpm, about 10 rpm to about 75 rpm, about 10 rpm to about 100 rpm, about 10 rpm to about 125 rpm, about 10 rpm to about 150 rpm, about 10 rpm to about 200 rpm, about 10 rpm to about 250 rpm, about 10 rpm to about 300 rpm, about 20 rpm to about 50 rpm, about 20 rpm to about 75 rpm, about 20 rpm to about 100 rpm, about 20 rpm to about 125 rpm, about 20 rpm to about 150 rpm, about 20 rpm to about 200 rpm, about 20 rpm to about 250 rpm, about 20 rpm to about 300 rpm, about 50 rpm to about 75 rpm, about 50 rpm to about 100 rpm, about 50 rpm to about 125 rpm, about 50 rpm to about 150 rpm, about 50 rpm to about 200 rpm, about 50 rpm to about 250 rpm, about 50 rpm to about 300 rpm, about 75 rpm to about 100 rpm, about 75 rpm to about 125 rpm, about 75 rpm to about 150 rpm, about 75 rpm to about 200 rpm, about 75 rpm to about 250 rpm, about 75 rpm to about 300 rpm, about 100 rpm to about 125 rpm, about 100 rpm to about 150 rpm, about 100 rpm to about 200 rpm, about 100 rpm to about 250 rpm, about 100 rpm to about 300 rpm, about 125 rpm to about 150 rpm, about 125 rpm to about 200 rpm, about 125 rpm to about 250 rpm, about 125 rpm to about 300 rpm, about 150 rpm to about 200 rpm, about 150 rpm to about 250 rpm, about 150 rpm to about 300 rpm, about 200 rpm to about 250 rpm, about 200 rpm to about 300 rpm, or about 250 rpm to about 300 rpm. In some embodiments the agitation occurs at a stirring rate of about 10 rpm, about 20 rpm, about 50 rpm, about 75 rpm, about 100 rpm, about 125 rpm, about 150 rpm, about 200 rpm, about 250 rpm, or about 300 rpm.

Some embodiments further comprise allowing the second solution to react for a period of time after the second solution is quenched.

In some embodiments the second solution reacts for a period of time of about 15 minutes to about 120 minutes. In some embodiments the second solution reacts for a period of time of at least about 15 minutes. In some embodiments the second solution reacts for a period of time of at most about 120 minutes. In some embodiments the second solution reacts for a period of time of about 15 minutes to about 20 minutes, about 15 minutes to about 30 minutes, about 15 minutes to about 40 minutes, about 15 minutes to about 50 minutes, about 15 minutes to about 60 minutes, about 15 minutes to about 70 minutes, about 15 minutes to about 80 minutes, about 15 minutes to about 90 minutes, about 15 minutes to about 100 minutes, about 15 minutes to about 110 minutes, about 15 minutes to about 120 minutes, about 20 minutes to about 30 minutes, about 20 minutes to about 40 minutes, about 20 minutes to about 50 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 40 minutes to about 50 minutes, about 40 minutes to about 60 minutes, about 40 minutes to about 70 minutes, about 40 minutes to about 80 minutes, about 40 minutes to about 90 minutes, about 40 minutes to about 100 minutes, about 40 minutes to about 110 minutes, about 40 minutes to about 120 minutes, about 50 minutes to about 60 minutes, about 50 minutes to about 70 minutes, about 50 minutes to about 80 minutes, about 50 minutes to about 90 minutes, about 50 minutes to about 100 minutes, about 50 minutes to about 110 minutes, about 50 minutes to about 120 minutes, about 60 minutes to about 70 minutes, about 60 minutes to about 80 minutes, about 60 minutes to about 90 minutes, about 60 minutes to about 100 minutes, about 60 minutes to about 110 minutes, about 60 minutes to about 120 minutes, about 70 minutes to about 80 minutes, about 70 minutes to about 90 minutes, about 70 minutes to about 100 minutes, about 70 minutes to about 110 minutes, about 70 minutes to about 120 minutes, about 80 minutes to about 90 minutes, about 80 minutes to about 100 minutes, about 80 minutes to about 110 minutes, about 80 minutes to about 120 minutes, about 90 minutes to about 100 minutes, about 90 minutes to about 110 minutes, about 90 minutes to about 120 minutes, about 100 minutes to about 110 minutes, about 100 minutes to about 120 minutes, or about 110 minutes to about 120 minutes. In some embodiments the second solution reacts for a period of time of about 15 minutes, about 20 minutes, about 30 minutes, about 40 minutes, about 50 minutes, about 60 minutes, about 70 minutes, about 80 minutes, about 90 minutes, about 100 minutes, about 110 minutes, or about 120 minutes.

In some embodiments the temperature of the second solution during the reaction is about 15° C. to about 75° C. In some embodiments the temperature of the second solution during the reaction is at least about 15° C. In some embodiments the temperature of the second solution during the reaction is at most about 75° C. In some embodiments the temperature of the second solution during the reaction is about 15° C. to about 20° C., about 15° C. to about 25° C., about 15° C. to about 30° C., about 15° C. to about 35° C., about 15° C. to about 40° C., about 15° C. to about 45° C., about 15° C. to about 50° C., about 15° C. to about 55° C., about 15° C. to about 60° C., about 15° C. to about 65° C., about 15° C. to about 75° C., about 20° C. to about 25° C., about 20° C. to about 30° C., about 20° C. to about 35° C., about 20° C. to about 40° C., about 20° C. to about 45° C., about 20° C. to about 50° C., about 20° C. to about 55° C., about 20° C. to about 60° C., about 20° C. to about 65° C., about 20° C. to about 75° C., about 25° C. to about 30° C., about 25° C. to about 35° C., about 25° C. to about 40° C., about 25° C. to about 45° C., about 25° C. to about 50° C., about 25° C. to about 55° C., about 25° C. to about 60° C., about 25° C. to about 65° C., about 25° C. to about 75° C., about 30° C. to about 35° C., about 30° C. to about 40° C., about 30° C. to about 45° C., about 30° C. to about 50° C., about 30° C. to about 55° C., about 30° C. to about 60° C., about 30° C. to about 65° C., about 30° C. to about 75° C., about 35° C. to about 40° C., about 35° C. to about 45° C., about 35° C. to about 50° C., about 35° C. to about 55° C., about 35° C. to about 60° C., about 35° C. to about 65° C., about 35° C. to about 75° C., about 40° C. to about 45° C., about 40° C. to about 50° C., about 40° C. to about 55° C., about 40° C. to about 60° C., about 40° C. to about 65° C., about 40° C. to about 75° C., about 45° C. to about 50° C., about 45° C. to about 55° C., about 45° C. to about 60° C., about 45° C. to about 65° C., about 45° C. to about 75° C., about 50° C. to about 55° C., about 50° C. to about 60° C., about 50° C. to about 65° C., about 50° C. to about 75° C., about 55° C. to about 60° C., about 55° C. to about 65° C., about 55° C. to about 75° C., about 60° C. to about 65° C., about 60° C. to about 75° C., or about 65° C. to about 75° C. In some embodiments the temperature of the second solution during the reaction is about 15° C., about 20° C., about 25° C., about 30° C., about 35° C., about 40° C., about 45° C., about 50° C., about 55° C., about 60° C., about 65° C., or about 75° C. In some embodiments the temperature of the second solution during the reaction is at most about 15° C., at most about 20° C., at most about 25° C., at most about 30° C., at most about 35° C., at most about 40° C., at most about 45° C., at most about 50° C., at most about 55° C., at most about 60° C., at most about 65° C., or at most about 75° C.

Some embodiments further comprise purifying the second solution. In some embodiments purifying the second solution comprises filtering the carbon-based oxide material through a filter and concentrating the carbon-based oxide material. In some embodiments filtering the carbon-based oxide material through a filter comprises centrifugal filtering, dead-end filtering, tangential-flow filtering, stationary phase filtering, dynamic phase filtering, surface filtering, depth filtering, vacuum filtering, recirculation filtering, or any combination thereof. In some embodiments the first filter comprises a Buchner funnel, a surface filter, a sieve, a filter paper, a belt filter, a drum filter, a cross-flow filter, a screen filter, a depth filter, a polymeric membrane, a ceramic membrane, a polyether sulfone filter, a hollow filter, a stainless steel filter, a stainless steel mesh, a carbon fiber mesh, a microfilter, an ultrafilter, a membrane, or any combination.

In some embodiments the first filter has a pore size of about 0.01 microns to about 4 microns. In some embodiments the first filter has a pore size of at least about 0.01 microns. In some embodiments the first filter has a pore size of at most about 4 microns. In some embodiments the first filter has a pore size of about 0.01 microns to about 0.05 microns, about 0.01 microns to about 0.1 microns, about 0.01 microns to about 0.5 microns, about 0.01 microns to about 1 micron, about 0.01 microns to about 1.5 microns, about 0.01 microns to about 2 microns, about 0.01 microns to about 2.5 microns, about 0.01 microns to about 3 microns, about 0.01 microns to about 3.5 microns, about 0.01 microns to about 4 microns, about 0.05 microns to about 0.1 microns, about 0.05 microns to about 0.5 microns, about 0.05 microns to about 1 micron, about 0.05 microns to about 1.5 microns, about 0.05 microns to about 2 microns, about 0.05 microns to about 2.5 microns, about 0.05 microns to about 3 microns, about 0.05 microns to about 3.5 microns, about 0.05 microns to about 4 microns, about 0.1 microns to about 0.5 microns, about 0.1 microns to about 1 micron, about 0.1 microns to about 1.5 microns, about 0.1 microns to about 2 microns, about 0.1 microns to about 2.5 microns, about 0.1 microns to about 3 microns, about 0.1 microns to about 3.5 microns, about 0.1 microns to about 4 microns, about 0.5 microns to about 1 micron, about 0.5 microns to about 1.5 microns, about 0.5 microns to about 2 microns, about 0.5 microns to about 2.5 microns, about 0.5 microns to about 3 microns, about 0.5 microns to about 3.5 microns, about 0.5 microns to about 4 microns, about 1 micron to about 1.5 microns, about 1 micron to about 2 microns, about 1 micron to about 2.5 microns, about 1 micron to about 3 microns, about 1 micron to about 3.5 microns, about 1 micron to about 4 microns, about 1.5 microns to about 2 microns, about 1.5 microns to about 2.5 microns, about 1.5 microns to about 3 microns, about 1.5 microns to about 3.5 microns, about 1.5 microns to about 4 microns, about 2 microns to about 2.5 microns, about 2 microns to about 3 microns, about 2 microns to about 3.5 microns, about 2 microns to about 4 microns, about 2.5 microns to about 3 microns, about 2.5 microns to about 3.5 microns, about 2.5 microns to about 4 microns, about 3 microns to about 3.5 microns, about 3 microns to about 4 microns, or about 3.5 microns to about 4 microns. In some embodiments the first filter has a pore size of about 0.01 microns, about 0.05 microns, about 0.1 microns, about 0.5 microns, about 1 micron, about 1.5 microns, about 2 microns, about 2.5 microns, about 3 microns, about 3.5 microns, or about 4 microns.

In some embodiments the carbon-based oxide material is filtered until its pH is about 3 to about 7. In some embodiments the carbon-based oxide material is filtered until its pH is at least about 3. In some embodiments the carbon-based oxide material is filtered until its pH is at most about 7. In some embodiments the carbon-based oxide material is filtered until its pH is about 3 to about 3.5, about 3 to about 4, about 3 to about 4.5, about 3 to about 5, about 3 to about 5.5, about 3 to about 6, about 3 to about 6.5, about 3 to about 7, about 3.5 to about 4, about 3.5 to about 4.5, about 3.5 to about 5, about 3.5 to about 5.5, about 3.5 to about 6, about 3.5 to about 6.5, about 3.5 to about 7, about 4 to about 4.5, about 4 to about 5, about 4 to about 5.5, about 4 to about 6, about 4 to about 6.5, about 4 to about 7, about 4.5 to about 5, about 4.5 to about 5.5, about 4.5 to about 6, about 4.5 to about 6.5, about 4.5 to about 7, about 5 to about 5.5, about 5 to about 6, about 5 to about 6.5, about 5 to about 7, about 5.5 to about 6, about 5.5 to about 6.5, about 5.5 to about 7, about 6 to about 6.5, about 6 to about 7, or about 6.5 to about 7. In some embodiments the carbon-based oxide material is filtered until its pH is about 3, about 3.5, about 4, about 4.5, about 5, about 5.5, about 6, about 6.5, or about 7.

In some embodiments the purified second solution has a graphite concentration by weight of about 0.25% to about 4%. In some embodiments the purified second solution has a graphite concentration by weight of at least about 0.25%. In some embodiments the purified second solution has a graphite concentration by weight of at most about 4%. In some embodiments the purified second solution has a graphite concentration by weight of about 0.25% to about 0.5%, about 0.25% to about 0.75%, about 0.25% to about 1%, about 0.25% to about 1.25%, about 0.25% to about 1.5%, about 0.25% to about 2%, about 0.25% to about 2.5%, about 0.25% to about 3%, about 0.25% to about 3.5%, about 0.25% to about 4%, about 0.5% to about 0.75%, about 0.5% to about 1%, about 0.5% to about 1.25%, about 0.5% to about 1.5%, about 0.5% to about 2%, about 0.5% to about 2.5%, about 0.5% to about 3%, about 0.5% to about 3.5%, about 0.5% to about 4%, about 0.75% to about 1%, about 0.75% to about 1.25%, about 0.75% to about 1.5%, about 0.75% to about 2%, about 0.75% to about 2.5%, about 0.75% to about 3%, about 0.75% to about 3.5%, about 0.75% to about 4%, about 1% to about 1.25%, about 1% to about 1.5%, about 1% to about 2%, about 1% to about 2.5%, about 1% to about 3%, about 1% to about 3.5%, about 1% to about 4%, about 1.25% to about 1.5%, about 1.25% to about 2%, about 1.25% to about 2.5%, about 1.25% to about 3%, about 1.25% to about 3.5%, about 1.25% to about 4%, about 1.5% to about 2%, about 1.5% to about 2.5%, about 1.5% to about 3%, about 1.5% to about 3.5%, about 1.5% to about 4%, about 2% to about 2.5%, about 2% to about 3%, about 2% to about 3.5%, about 2% to about 4%, about 2.5% to about 3%, about 2.5% to about 3.5%, about 2.5% to about 4%, about 3% to about 3.5%, about 3% to about 4%, or about 3.5% to about 4%. In some embodiments the purified second solution has a graphite concentration by weight of about 0.25%, about 0.5%, about 0.75%, about 1%, about 1.25%, about 1.5%, about 2%, about 2.5%, about 3%, about 3.5%, or about 4%.

Some embodiments further comprise: forming a third solution comprising the carbon-based oxide material and a third oxidizing agent; heating the third solution to a fourth temperature for a period of time; and adding a mineral ascorbate to the third solution to form a reduced carbon-based oxide material.

In some embodiments heating the carbon-based oxide material to the fourth temperature, and adding the first quantity of the third oxidizing agent to the carbon-based oxide material, occur simultaneously.

In some embodiments the fourth temperature is about 45° C. to about 180° C. In some embodiments the fourth temperature is at least about 45° C. In some embodiments the fourth temperature is at most about 180° C. In some embodiments the fourth temperature is about 45° C. to about 50° C., about 45° C. to about 60° C., about 45° C. to about 70° C., about 45° C. to about 80° C., about 45° C. to about 90° C., about 45° C. to about 100° C., about 45° C. to about 120° C., about 45° C. to about 140° C., about 45° C. to about 160° C., about 45° C. to about 180° C., about 50° C. to about 60° C., about 50° C. to about 70° C., about 50° C. to about 80° C., about 50° C. to about 90° C., about 50° C. to about 100° C., about 50° C. to about 120° C., about 50° C. to about 140° C., about 50° C. to about 160° C., about 50° C. to about 180° C., about 60° C. to about 70° C., about 60° C. to about 80° C., about 60° C. to about 90° C., about 60° C. to about 100° C., about 60° C. to about 120° C., about 60° C. to about 140° C., about 60° C. to about 160° C., about 60° C. to about 180° C., about 70° C. to about 80° C., about 70° C. to about 90° C., about 70° C. to about 100° C., about 70° C. to about 120° C., about 70° C. to about 140° C., about 70° C. to about 160° C., about 70° C. to about 180° C., about 80° C. to about 90° C., about 80° C. to about 100° C., about 80° C. to about 120° C., about 80° C. to about 140° C., about 80° C. to about 160° C., about 80° C. to about 180° C., about 90° C. to about 100° C., about 90° C. to about 120° C., about 90° C. to about 140° C., about 90° C. to about 160° C., about 90° C. to about 180° C., about 100° C. to about 120° C., about 100° C. to about 140° C., about 100° C. to about 160° C., about 100° C. to about 180° C., about 120° C. to about 140° C., about 120° C. to about 160° C., about 120° C. to about 180° C., about 140° C. to about 160° C., about 140° C. to about 180° C., or about 160° C. to about 180° C. In some embodiments the fourth temperature is about 45° C., about 50° C., about 60° C., about 70° C., about 80° C., about 90° C., about 100° C., about 120° C., about 140° C., about 160° C., or about 180° C. In some embodiments the fourth temperature is at most about 45° C., at most about 50° C., at most about 60° C., at most about 70° C., at most about 80° C., at most about 90° C., at most about 100° C., at most about 120° C., at most about 140° C., at most about 160° C., or at most about 180° C.

In some embodiments heating the third solution to a fourth temperature occurs over a period of time of about 30 minutes to about 120 minutes. In some embodiments heating the third solution to a fourth temperature occurs over a period of time of at least about 30 minutes. In some embodiments heating the third solution to a fourth temperature occurs over a period of time of at most about 120 minutes. In some embodiments heating the third solution to a fourth temperature occurs over a period of time of about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 120 minutes, about 30 minutes to about 120 minutes, about 40 minutes to about 50 minutes, about 40 minutes to about 60 minutes, about 40 minutes to about 70 minutes, about 40 minutes to about 80 minutes, about 40 minutes to about 90 minutes, about 40 minutes to about 100 minutes, about 40 minutes to about 120 minutes, about 40 minutes to about 120 minutes, about 50 minutes to about 60 minutes, about 50 minutes to about 70 minutes, about 50 minutes to about 80 minutes, about 50 minutes to about 90 minutes, about 50 minutes to about 100 minutes, about 50 minutes to about 120 minutes, about 50 minutes to about 120 minutes, about 60 minutes to about 70 minutes, about 60 minutes to about 80 minutes, about 60 minutes to about 90 minutes, about 60 minutes to about 100 minutes, about 60 minutes to about 120 minutes, about 60 minutes to about 120 minutes, about 70 minutes to about 80 minutes, about 70 minutes to about 90 minutes, about 70 minutes to about 100 minutes, about 70 minutes to about 120 minutes, about 70 minutes to about 120 minutes, about 80 minutes to about 90 minutes, about 80 minutes to about 100 minutes, about 80 minutes to about 120 minutes, about 80 minutes to about 120 minutes, about 90 minutes to about 100 minutes, about 90 minutes to about 120 minutes, about 90 minutes to about 120 minutes, about 100 minutes to about 120 minutes, about 100 minutes to about 120 minutes, or about 120 minutes to about 120 minutes. In some embodiments heating the third solution to a fourth temperature occurs over a period of time of about 30 minutes, about 40 minutes, about 50 minutes, about 60 minutes, about 70 minutes, about 80 minutes, about 90 minutes, about 100 minutes, about 120 minutes, or about 120 minutes.

In some embodiments the third oxidizing agent comprises oxygen, ozone, hydrogen peroxide, fluorite dioxide, lithium peroxide, barium peroxide, fluorine, chlorine, nitric acid, nitrate compounds, sulfuric acid, peroxydisulfuric acid, peroxymonosulfuric acid, chlorite, chlorate, perchlorate, halogen compounds hypochlorite, hypohalite compounds, household bleach, hexavalent chromium compounds, chromic acids, dichromic acids, chromium trioxide, pyridinium chlorochromate, chromate compounds, dichromate compounds, permanganate compounds, potassium permanganate, sodium perborate, nitrous oxide, potassium nitrate, sodium bismuthate or any combination thereof.

In some embodiments the concentration of the third oxidizing agent is about 15% to about 60%. In some embodiments the concentration of the third oxidizing agent is at least about 15%. In some embodiments the concentration of the third oxidizing agent is at most about 60%. In some embodiments the concentration of the third oxidizing agent is about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments the concentration of the third oxidizing agent is about 15%, about 20%, about 25%, about 30%, about 35%, about 40%, about 45%, about 50%, about 55%, or about 60%.

In some embodiments the mass of the second quantity of the third oxidizing agent is greater than the mass of the graphite by a factor of about 1.1 to about 6. In some embodiments the mass of the second quantity of the third oxidizing agent is greater than the mass of the graphite by a factor of at least about 1.1. In some embodiments the mass of the second quantity of the third oxidizing agent is greater than the mass of the graphite by a factor of at most about 6. In some embodiments the mass of the second quantity of the third oxidizing agent is greater than the mass of the graphite by a factor of about 1.1 to about 1.2, about 1.1 to about 1.5, about 1.1 to about 2, about 1.1 to about 2.5, about 1.1 to about 3, about 1.1 to about 3.5, about 1.1 to about 4, about 1.1 to about 4.5, about 1.1 to about 5, about 1.1 to about 5.5, about 1.1 to about 6, about 1.2 to about 1.5, about 1.2 to about 2, about 1.2 to about 2.5, about 1.2 to about 3, about 1.2 to about 3.5, about 1.2 to about 4, about 1.2 to about 4.5, about 1.2 to about 5, about 1.2 to about 5.5, about 1.2 to about 6, about 1.5 to about 2, about 1.5 to about 2.5, about 1.5 to about 3, about 1.5 to about 3.5, about 1.5 to about 4, about 1.5 to about 4.5, about 1.5 to about 5, about 1.5 to about 5.5, about 1.5 to about 6, about 2 to about 2.5, about 2 to about 3, about 2 to about 3.5, about 2 to about 4, about 2 to about 4.5, about 2 to about 5, about 2 to about 5.5, about 2 to about 6, about 2.5 to about 3, about 2.5 to about 3.5, about 2.5 to about 4, about 2.5 to about 4.5, about 2.5 to about 5, about 2.5 to about 5.5, about 2.5 to about 6, about 3 to about 3.5, about 3 to about 4, about 3 to about 4.5, about 3 to about 5, about 3 to about 5.5, about 3 to about 6, about 3.5 to about 4, about 3.5 to about 4.5, about 3.5 to about 5, about 3.5 to about 5.5, about 3.5 to about 6, about 4 to about 4.5, about 4 to about 5, about 4 to about 5.5, about 4 to about 6, about 4.5 to about 5, about 4.5 to about 5.5, about 4.5 to about 6, about 5 to about 5.5, about 5 to about 6, or about 5.5 to about 6. In some embodiments the mass of the second quantity of the third oxidizing agent is greater than the mass of the graphite by a factor of about 1.1, about 1.2, about 1.5, about 2, about 2.5, about 3, about 3.5, about 4, about 4.5, about 5, about 5.5, or about 6.

In some embodiments the mineral ascorbate comprises sodium ascorbate, calcium ascorbate, potassium ascorbate, magnesium ascorbate, or any combination thereof.

In some embodiments the mass of the mineral ascorbate is greater than the mass of the graphite by a factor of about 2% to about 10%. In some embodiments the mass of the mineral ascorbate is greater than the mass of the graphite by a factor of at least about 2%. In some embodiments the mass of the mineral ascorbate is greater than the mass of the graphite by a factor of at most about 10%. In some embodiments the mass of the mineral ascorbate is greater than the mass of the graphite by a factor of about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 8% to about 10%, or about 9% to about 10%. In some embodiments the mass of the mineral ascorbate is greater than the mass of the graphite by a factor of about 2%, about 3%, about 4%, about 5%, about 6%, about 7%, about 8%, about 9%, or about 10%.

In some embodiments the mineral ascorbate is added to the third solution over a period of time of about 10 minutes to about 60 minutes. In some embodiments the mineral ascorbate is added to the third solution over a period of time of at least about 10 minutes. In some embodiments the mineral ascorbate is added to the third solution over a period of time of at most about 60 minutes. In some embodiments the mineral ascorbate is added to the third solution over a period of time of about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 10 minutes to about 45 minutes, about 10 minutes to about 50 minutes, about 10 minutes to about 55 minutes, about 10 minutes to about 60 minutes, about 15 minutes to about 20 minutes, about 15 minutes to about 25 minutes, about 15 minutes to about 30 minutes, about 15 minutes to about 35 minutes, about 15 minutes to about 40 minutes, about 15 minutes to about 45 minutes, about 15 minutes to about 50 minutes, about 15 minutes to about 55 minutes, about 15 minutes to about 60 minutes, about 20 minutes to about 25 minutes, about 20 minutes to about 30 minutes, about 20 minutes to about 35 minutes, about 20 minutes to about 40 minutes, about 20 minutes to about 45 minutes, about 20 minutes to about 50 minutes, about 20 minutes to about 55 minutes, about 20 minutes to about 60 minutes, about 25 minutes to about 30 minutes, about 25 minutes to about 35 minutes, about 25 minutes to about 40 minutes, about 25 minutes to about 45 minutes, about 25 minutes to about 50 minutes, about 25 minutes to about 55 minutes, about 25 minutes to about 60 minutes, about 30 minutes to about 35 minutes, about 30 minutes to about 40 minutes, about 30 minutes to about 45 minutes, about 30 minutes to about 50 minutes, about 30 minutes to about 55 minutes, about 30 minutes to about 60 minutes, about 35 minutes to about 40 minutes, about 35 minutes to about 45 minutes, about 35 minutes to about 50 minutes, about 35 minutes to about 55 minutes, about 35 minutes to about 60 minutes, about 40 minutes to about 45 minutes, about 40 minutes to about 50 minutes, about 40 minutes to about 55 minutes, about 40 minutes to about 60 minutes, about 45 minutes to about 50 minutes, about 45 minutes to about 55 minutes, about 45 minutes to about 60 minutes, about 50 minutes to about 55 minutes, about 50 minutes to about 60 minutes, or about 55 minutes to about 60 minutes. In some embodiments the mineral ascorbate is added to the third solution over a period of time of about 10 minutes, about 15 minutes, about 20 minutes, about 25 minutes, about 30 minutes, about 35 minutes, about 40 minutes, about 45 minutes, about 50 minutes, about 55 minutes, or about 60 minutes.

Some embodiments further comprise allowing the third solution and the mineral solution to react for a period of time of about 45 minutes to about 180 minutes. Some embodiments further comprise allowing the third solution and the mineral solution to react for a period of time of at least about 45 minutes. Some embodiments further comprise allowing the third solution and the mineral solution to react for a period of time of at most about 180 minutes. Some embodiments further comprise allowing the third solution and the mineral solution to react for a period of time of about 45 minutes to about 50 minutes, about 45 minutes to about 60 minutes, about 45 minutes to about 70 minutes, about 45 minutes to about 80 minutes, about 45 minutes to about 90 minutes, about 45 minutes to about 100 minutes, about 45 minutes to about 120 minutes, about 45 minutes to about 140 minutes, about 45 minutes to about 160 minutes, about 45 minutes to about 180 minutes, about 50 minutes to about 60 minutes, about 50 minutes to about 70 minutes, about 50 minutes to about 80 minutes, about 50 minutes to about 90 minutes, about 50 minutes to about 100 minutes, about 50 minutes to about 120 minutes, about 50 minutes to about 140 minutes, about 50 minutes to about 160 minutes, about 50 minutes to about 180 minutes, about 60 minutes to about 70 minutes, about 60 minutes to about 80 minutes, about 60 minutes to about 90 minutes, about 60 minutes to about 100 minutes, about 60 minutes to about 120 minutes, about 60 minutes to about 140 minutes, about 60 minutes to about 160 minutes, about 60 minutes to about 180 minutes, about 70 minutes to about 80 minutes, about 70 minutes to about 90 minutes, about 70 minutes to about 100 minutes, about 70 minutes to about 120 minutes, about 70 minutes to about 140 minutes, about 70 minutes to about 160 minutes, about 70 minutes to about 180 minutes, about 80 minutes to about 90 minutes, about 80 minutes to about 100 minutes, about 80 minutes to about 120 minutes, about 80 minutes to about 140 minutes, about 80 minutes to about 160 minutes, about 80 minutes to about 180 minutes, about 90 minutes to about 100 minutes, about 90 minutes to about 120 minutes, about 90 minutes to about 140 minutes, about 90 minutes to about 160 minutes, about 90 minutes to about 180 minutes, about 100 minutes to about 120 minutes, about 100 minutes to about 140 minutes, about 100 minutes to about 160 minutes, about 100 minutes to about 180 minutes, about 120 minutes to about 140 minutes, about 120 minutes to about 160 minutes, about 120 minutes to about 180 minutes, about 140 minutes to about 160 minutes, about 140 minutes to about 180 minutes, or about 160 minutes to about 180 minutes. Some embodiments further comprise allowing the third solution and the mineral solution to react for a period of time of about 45 minutes, about 50 minutes, about 60 minutes, about 70 minutes, about 80 minutes, about 90 minutes, about 100 minutes, about 120 minutes, about 140 minutes, about 160 minutes, or about 180 minutes.

Some embodiments further comprise agitating the third solution. In some embodiments the agitation occurs for a period of time of about 45 minutes to about 360 minutes. In some embodiments the agitation occurs for a period of time of at least about 45 minutes. In some embodiments the agitation occurs for a period of time of at most about 360 minutes. In some embodiments the agitation occurs for a period of time of about 45 minutes to about 60 minutes, about 45 minutes to about 80 minutes, about 45 minutes to about 100 minutes, about 45 minutes to about 140 minutes, about 45 minutes to about 180 minutes, about 45 minutes to about 220 minutes, about 45 minutes to about 260 minutes, about 45 minutes to about 300 minutes, about 45 minutes to about 360 minutes, about 60 minutes to about 80 minutes, about 60 minutes to about 100 minutes, about 60 minutes to about 140 minutes, about 60 minutes to about 180 minutes, about 60 minutes to about 220 minutes, about 60 minutes to about 260 minutes, about 60 minutes to about 300 minutes, about 60 minutes to about 360 minutes, about 80 minutes to about 100 minutes, about 80 minutes to about 140 minutes, about 80 minutes to about 180 minutes, about 80 minutes to about 220 minutes, about 80 minutes to about 260 minutes, about 80 minutes to about 300 minutes, about 80 minutes to about 360 minutes, about 100 minutes to about 140 minutes, about 100 minutes to about 180 minutes, about 100 minutes to about 220 minutes, about 100 minutes to about 260 minutes, about 100 minutes to about 300 minutes, about 100 minutes to about 360 minutes, about 140 minutes to about 180 minutes, about 140 minutes to about 220 minutes, about 140 minutes to about 260 minutes, about 140 minutes to about 300 minutes, about 140 minutes to about 360 minutes, about 180 minutes to about 220 minutes, about 180 minutes to about 260 minutes, about 180 minutes to about 300 minutes, about 180 minutes to about 360 minutes, about 220 minutes to about 260 minutes, about 220 minutes to about 300 minutes, about 220 minutes to about 360 minutes, about 260 minutes to about 300 minutes, about 260 minutes to about 360 minutes, or about 300 minutes to about 360 minutes. In some embodiments the agitation occurs for a period of time of about 45 minutes, about 60 minutes, about 80 minutes, about 100 minutes, about 140 minutes, about 180 minutes, about 220 minutes, about 260 minutes, about 300 minutes, or about 360 minutes.

Some embodiments further comprise purifying the reduced carbon-based oxide material. In some embodiments purifying the reduced carbon-based oxide material comprises filtering with a second filter, flushing the third solution, or any combination thereof. In some embodiments filtering the reduced carbon-based oxide material comprises centrifugal filtering, dead-end filtering, tangential-flow filtering, stationary phase filtering, dynamic phase filtering, surface filtering, depth filtering, vacuum filtering, recirculation filtering, or any combination thereof. In some embodiments the second filter comprises a Buchner funnel, a surface filter, a sieve, a filter paper, a belt filter, a drum filter, a cross-flow filter, a screen filter, a depth filter, a polymeric membrane, a ceramic membrane, a hollow filter, a stainless steel filter, a stainless steel mesh, a carbon fiber mesh, a microfilter, an ultrafilter, a membrane, or any combination thereof.

In some embodiments the second filter has a pore size of about 0.5 microns to about 5 microns. In some embodiments the second filter has a pore size of at least about 0.5 microns. In some embodiments the second filter has a pore size of at most about 5 microns. In some embodiments the second filter has a pore size of about 0.5 microns to about 1 micron, about 0.5 microns to about 1.5 microns, about 0.5 microns to about 2 microns, about 0.5 microns to about 2.5 microns, about 0.5 microns to about 3 microns, about 0.5 microns to about 3.5 microns, about 0.5 microns to about 4 microns, about 0.5 microns to about 4.5 microns, about 0.5 microns to about 5 microns, about 1 micron to about 1.5 microns, about 1 micron to about 2 microns, about 1 micron to about 2.5 microns, about 1 micron to about 3 microns, about 1 micron to about 3.5 microns, about 1 micron to about 4 microns, about 1 micron to about 4.5 microns, about 1 micron to about 5 microns, about 1.5 microns to about 2 microns, about 1.5 microns to about 2.5 microns, about 1.5 microns to about 3 microns, about 1.5 microns to about 3.5 microns, about 1.5 microns to about 4 microns, about 1.5 microns to about 4.5 microns, about 1.5 microns to about 5 microns, about 2 microns to about 2.5 microns, about 2 microns to about 3 microns, about 2 microns to about 3.5 microns, about 2 microns to about 4 microns, about 2 microns to about 4.5 microns, about 2 microns to about 5 microns, about 2.5 microns to about 3 microns, about 2.5 microns to about 3.5 microns, about 2.5 microns to about 4 microns, about 2.5 microns to about 4.5 microns, about 2.5 microns to about 5 microns, about 3 microns to about 3.5 microns, about 3 microns to about 4 microns, about 3 microns to about 4.5 microns, about 3 microns to about 5 microns, about 3.5 microns to about 4 microns, about 3.5 microns to about 4.5 microns, about 3.5 microns to about 5 microns, about 4 microns to about 4.5 microns, about 4 microns to about 5 microns, or about 4.5 microns to about 5 microns. In some embodiments the second filter has a pore size of about 0.5 microns, about 1 micron, about 1.5 microns, about 2 microns, about 2.5 microns, about 3 microns, about 3.5 microns, about 4 microns, about 4.5 microns, or about 5 microns.

In some embodiments the reduced carbon-based oxide material is purified until its conductivity is about 1 S/m to about 10 S/m. In some embodiments the reduced carbon-based oxide material is purified until its conductivity is at least about 1 S/m. In some embodiments the reduced carbon-based oxide material is purified until its conductivity is at most about 10 S/m. In some embodiments the reduced carbon-based oxide material is purified until its conductivity is about 1 S/m to about 2 S/m, about 1 S/m to about 3 S/m, about 1 S/m to about 4 S/m, about 1 S/m to about 5 S/m, about 1 S/m to about 6 S/m, about 1 S/m to about 7 S/m, about 1 S/m to about 8 S/m, about 1 S/m to about 9 S/m, about 1 S/m to about 10 S/m, about 2 S/m to about 3 S/m, about 2 S/m to about 4 S/m, about 2 S/m to about 5 S/m, about 2 S/m to about 6 S/m, about 2 S/m to about 7 S/m, about 2 S/m to about 8 S/m, about 2 S/m to about 9 S/m, about 2 S/m to about 10 S/m, about 3 S/m to about 4 S/m, about 3 S/m to about 5 S/m, about 3 S/m to about 6 S/m, about 3 S/m to about 7 S/m, about 3 S/m to about 8 S/m, about 3 S/m to about 9 S/m, about 3 S/m to about 10 S/m, about 4 S/m to about 5 S/m, about 4 S/m to about 6 S/m, about 4 S/m to about 7 S/m, about 4 S/m to about 8 S/m, about 4 S/m to about 9 S/m, about 4 S/m to about 10 S/m, about 5 S/m to about 6 S/m, about 5 S/m to about 7 S/m, about 5 S/m to about 8 S/m, about 5 S/m to about 9 S/m, about 5 S/m to about 10 S/m, about 6 S/m to about 7 S/m, about 6 S/m to about 8 S/m, about 6 S/m to about 9 S/m, about 6 S/m to about 10 S/m, about 7 S/m to about 8 S/m, about 7 S/m to about 9 S/m, about 7 S/m to about 10 S/m, about 8 S/m to about 9 S/m, about 8 S/m to about 10 S/m, or about 9 S/m to about 10 S/m. In some embodiments the reduced carbon-based oxide material is purified until its conductivity is about 1 S/m, about 2 S/m, about 3 S/m, about 4 S/m, about 5 S/m, about 6 S/m, about 7 S/m, about 8 S/m, about 9 S/m, or about 10 S/m. In some embodiments the reduced carbon-based oxide material is purified until its conductivity is at least about 1 S/m, at least about 2 S/m, at least about 3 S/m, at least about 4 S/m, at least about 5 S/m, at least about 6 S/m, at least about 7 S/m, at least about 8 S/m, at least about 9 S/m, or at least about 10 S/m.

In some embodiments the carbon-based oxide material comprises a single layer. In some embodiments the carbon-based oxide material comprises a plurality of layers. In some embodiments the carbon-based oxide material comprises graphite, graphite oxide, reduced carbon-based, an interconnected corrugated carbon-based network (ICCN), or porous carbon sheet(s) (PCS).

In some embodiments the carbon-based oxide material has an ionic conductivity of about 5 μS/cm to about 400 μS/cm. In some embodiments the carbon-based oxide material has an ionic conductivity of at least about 5 μS/cm. In some embodiments the carbon-based oxide material has an ionic conductivity of at most about 400 μS/cm. In some embodiments the carbon-based oxide material has an ionic conductivity of about 5 μS/cm to about 10 μS/cm, about 5 μS/cm to about 20 μS/cm, about 5 μS/cm to about 50 μS/cm, about 5 μS/cm to about 75 μS/cm, about 5 μS/cm to about 100 μS/cm, about 5 μS/cm to about 150 μS/cm, about 5 μS/cm to about 200 μS/cm, about 5 μS/cm to about 250 μS/cm, about 5 μS/cm to about 300 μS/cm, about 5 μS/cm to about 350 μS/cm, about 5 μS/cm to about 400 μS/cm, about 10 μS/cm to about 20 μS/cm, about 10 μS/cm to about 50 μS/cm, about 10 μS/cm to about 75 μS/cm, about 10 μS/cm to about 100 μS/cm, about 10 μS/cm to about 150 μS/cm, about 10 μS/cm to about 200 μS/cm, about 10 μS/cm to about 250 μS/cm, about 10 μS/cm to about 300 μS/cm, about 10 μS/cm to about 350 μS/cm, about 10 μS/cm to about 400 μS/cm, about 20 μS/cm to about 50 μS/cm, about 20 μS/cm to about 75 μS/cm, about 20 μS/cm to about 100 μS/cm, about 20 μS/cm to about 150 μS/cm, about 20 μS/cm to about 200 μS/cm, about 20 μS/cm to about 250 μS/cm, about 20 μS/cm to about 300 μS/cm, about 20 μS/cm to about 350 μS/cm, about 20 μS/cm to about 400 μS/cm, about 50 μS/cm to about 75 μS/cm, about 50 μS/cm to about 100 μS/cm, about 50 μS/cm to about 150 μS/cm, about 50 μS/cm to about 200 μS/cm, about 50 μS/cm to about 250 μS/cm, about 50 μS/cm to about 300 μS/cm, about 50 μS/cm to about 350 μS/cm, about 50 μS/cm to about 400 μS/cm, about 75 μS/cm to about 100 μS/cm, about 75 μS/cm to about 150 μS/cm, about 75 μS/cm to about 200 μS/cm, about 75 μS/cm to about 250 μS/cm, about 75 μS/cm to about 300 μS/cm, about 75 μS/cm to about 350 μS/cm, about 75 μS/cm to about 400 μS/cm, about 100 μS/cm to about 150 μS/cm, about 100 μS/cm to about 200 μS/cm, about 100 μS/cm to about 250 μS/cm, about 100 μS/cm to about 300 μS/cm, about 100 μS/cm to about 350 μS/cm, about 100 μS/cm to about 400 μS/cm, about 150 μS/cm to about 200 μS/cm, about 150 μS/cm to about 250 μS/cm, about 150 μS/cm to about 300 μS/cm, about 150 μS/cm to about 350 μS/cm, about 150 μS/cm to about 400 μS/cm, about 200 μS/cm to about 250 μS/cm, about 200 μS/cm to about 300 μS/cm, about 200 μS/cm to about 350 μS/cm, about 200 μS/cm to about 400 μS/cm, about 250 μS/cm to about 300 μS/cm, about 250 μS/cm to about 350 μS/cm, about 250 μS/cm to about 400 μS/cm, about 300 μS/cm to about 350 μS/cm, about 300 μS/cm to about 400 μS/cm, or about 350 μS/cm to about 400 μS/cm. In some embodiments the carbon-based oxide material has an ionic conductivity of about 5 μS/cm, about 10 μS/cm, about 20 μS/cm, about 50 μS/cm, about 75 μS/cm, about 100 μS/cm, about 150 μS/cm, about 200 μS/cm, about 250 μS/cm, about 300 μS/cm, about 350 μS/cm, or about 400 μS/cm. In some embodiments the carbon-based oxide material has an ionic conductivity of at least about 5 μS/cm, at least about 10 μS/cm, at least about 20 μS/cm, at least about 50 μS/cm, at least about 75 μS/cm, at least about 100 μS/cm, at least about 150 µS/cm, at least about 200 µS/cm, at least about 250 µS/cm, at least about 300 µS/cm, at least about 350 µS/cm, or at least about 400 µS/cm.

In some embodiments the carbon-based oxide material has a purity of about 80% to about 99%. In some embodiments the carbon-based oxide material has a purity of at least about 80%. In some embodiments the carbon-based oxide material has a purity of at most about 99%. In some embodiments the carbon-based oxide material has a purity of about 80% to about 82%, about 80% to about 84%, about 80% to about 86%, about 80% to about 88%, about 80% to about 90%, about 80% to about 92%, about 80% to about 94%, about 80% to about 96%, about 80% to about 98%, about 80% to about 99%, about 82% to about 84%, about 82% to about 86%, about 82% to about 88%, about 82% to about 90%, about 82% to about 92%, about 82% to about 94%, about 82% to about 96%, about 82% to about 98%, about 82% to about 99%, about 84% to about 86%, about 84% to about 88%, about 84% to about 90%, about 84% to about 92%, about 84% to about 94%, about 84% to about 96%, about 84% to about 98%, about 84% to about 99%, about 86% to about 88%, about 86% to about 90%, about 86% to about 92%, about 86% to about 94%, about 86% to about 96%, about 86% to about 98%, about 86% to about 99%, about 88% to about 90%, about 88% to about 92%, about 88% to about 94%, about 88% to about 96%, about 88% to about 98%, about 88% to about 99%, about 90% to about 92%, about 90% to about 94%, about 90% to about 96%, about 90% to about 98%, about 90% to about 99%, about 92% to about 94%, about 92% to about 96%, about 92% to about 98%, about 92% to about 99%, about 94% to about 96%, about 94% to about 98%, about 94% to about 99%, about 96% to about 98%, about 96% to about 99%, or about 98% to about 99%. In some embodiments the carbon-based oxide material has a purity of about 80%, about 82%, about 84%, about 86%, about 88%, about 90%, about 92%, about 94%, about 96%, about 98%, or about 99%. In some embodiments the carbon-based oxide material has a purity of at least about 80%, at least about 82%, at least about 84%, at least about 86%, at least about 88%, at least about 90%, at least about 92%, at least about 94%, at least about 96%, at least about 98%, or at least about 99%.

In some embodiments the carbon-based oxide material comprises a carbon content by weight of about 1% to about 99%. In some embodiments the carbon-based oxide material comprises a carbon content by weight of at least about 1%. In some embodiments the carbon-based oxide material comprises a carbon content by weight of at most about 99%. In some embodiments the carbon-based oxide material comprises a carbon content by weight of about 1% to about 5%, about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 99%, about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 5% to about 99%, about 10% to about 20%, about 10% to about 30%, about 10% to about 40%, about 10% to about 50%, about 10% to about 60%, about 10% to about 70%, about 10% to about 80%, about 10% to about 90%, about 10% to about 99%, about 20% to about 30%, about 20% to about 40%, about 20% to about 50%, about 20% to about 60%, about 20% to about 70%, about 20% to about 80%, about 20% to about 90%, about 20% to about 99%, about 30% to about 40%, about 30% to about 50%, about 30% to about 60%, about 30% to about 70%, about 30% to about 80%, about 30% to about 90%, about 30% to about 99%, about 40% to about 50%, about 40% to about 60%, about 40% to about 70%, about 40% to about 80%, about 40% to about 90%, about 40% to about 99%, about 50% to about 60%, about 50% to about 70%, about 50% to about 80%, about 50% to about 90%, about 50% to about 99%, about 60% to about 70%, about 60% to about 80%, about 60% to about 90%, about 60% to about 99%, about 70% to about 80%, about 70% to about 90%, about 70% to about 99%, about 80% to about 90%, about 80% to about 99%, or about 90% to about 99%. In some embodiments the carbon-based oxide material comprises a carbon content by weight of about 1%, about 5%, about 10%, about 20%, about 30%, about 40%, about 50%, about 60%, about 70%, about 80%, about 90%, or about 99%.

In some embodiments, the method taught herein is capable of producing a throughput of carbon-based oxide material of about 0.1 pound/day to about 50 pounds/day. In some embodiments, the method taught herein is capable of producing a throughput of carbon-based oxide material of at least about 0.1 pound/day. In some embodiments, the method taught herein is capable of producing a throughput of carbon-based oxide material of at most about 50 pounds/day. In some embodiments, the method taught herein is capable of producing a throughput of carbon-based oxide material of about 0.1 pound/day to about 0.5 pound/day, about 0.1 pound/day to about 1 pound/day, about 0.1 pound/day to about 2 pounds/day, about 0.1 pound/day to about 5 pounds/day, about 0.1 pound/day to about 10 pounds/day, about 0.1 pound/day to about 20 pounds/day, about 0.1 pound/day to about 30 pounds/day, about 0.1 pound/day to about 40 pounds/day, about 0.1 pound/day to about 50 pounds/day, about 0.5 pound/day to about 1 pound/day, about 0.5 pound/day to about 2 pounds/day, about 0.5 pound/day to about 5 pounds/day, about 0.5 pound/day to about 10 pounds/day, about 0.5 pound/day to about 20 pounds/day, about 0.5 pound/day to about 30 pounds/day, about 0.5 pound/day to about 40 pounds/day, about 0.5 pound/day to about 50 pounds/day, about 1 pound/day to about 2 pounds/day, about 1 pound/day to about 5 pounds/day, about 1 pound/day to about 10 pounds/day, about 1 pound/day to about 20 pounds/day, about 1 pound/day to about 30 pounds/day, about 1 pound/day to about 40 pounds/day, about 1 pound/day to about 50 pounds/day, about 2 pounds/day to about 5 pounds/day, about 2 pounds/day to about 10 pounds/day, about 2 pounds/day to about 20 pounds/day, about 2 pounds/day to about 30 pounds/day, about 2 pounds/day to about 40 pounds/day, about 2 pounds/day to about 50 pounds/day, about 5 pounds/day to about 10 pounds/day, about 5 pounds/day to about 20 pounds/day, about 5 pounds/day to about 30 pounds/day, about 5 pounds/day to about 40 pounds/day, about 5 pounds/day to about 50 pounds/day, about 10 pounds/day to about 20 pounds/day, about 10 pounds/day to about 30 pounds/day, about 10 pounds/day to about 40 pounds/day, about 10 pounds/day to about 50 pounds/day, about 20 pounds/day to about 30 pounds/day, about 20 pounds/day to about 40 pounds/day, about 20 pounds/day to about 50 pounds/day, about 30 pounds/day to about 40 pounds/day, about 30 pounds/day to about 50 pounds/day, or about 40 pounds/day to about 50 pounds/day. In some embodiments, the method taught herein is capable of producing a throughput of carbon-based oxide material of about 0.1 pound/day, about 0.5 pound/day, about 1 pound/day, about 2 pounds/day, about 5 pounds/day, about 10 pounds/day, about 20 pounds/day, about 30 pounds/day, about 40 pounds/day, or about 50 pounds/day. In some embodiments, the method taught herein is capable of producing a throughput of carbon-based oxide material of at least about 0.1 pound/day, at least about 0.5 pound/day, at least about 1 pound/day, at least about 2 pounds/day, at least about 5 pounds/day, at least about 10 pounds/day, at least about 20 pounds/day, at least about 30 pounds/day, at least about 40 pounds/day, or at least about 50 pounds/day.

In some embodiments, an aspect provided herein is a method for producing graphite oxide comprising steps of: providing a graphite powder and sulfuric acid ($H_2SO_4$) mixture while cooling the graphite powder and $H_2SO_4$ mixture to a first predetermined temperature; adding a predetermined amount of potassium permanganate ($KMnO_4$) to the graphite powder and $H_2SO_4$ mixture to make a graphite oxidizing mixture; agitating the graphite oxidizing mixture for a predetermined amount of time; cooling the graphite oxidizing mixture to a second predetermined temperature; and adding a predetermined amount of hydrogen peroxide ($H_2O_2$) to the graphite oxidizing mixture to yield the graphite oxide.

In some embodiments, the method for producing graphite oxide further comprises purifying the graphite oxide by rinsing the graphite oxide with water.

In some embodiments, the method for producing graphite oxide further comprises purifying the graphite oxide by chemistry dialysis.

In some embodiments, the first predetermined temperature resulting from cooling the graphite powder and $H_2SO_4$ mixture is about 0° C. In some embodiments, the first predetermined temperature resulting from cooling the graphite powder and $H_2SO_4$ mixture ranges from about –10° C. to about 15° C. In some embodiments, a reaction temperature of the graphite oxidizing mixture is prevented from rising above about 15° C. while adding the predetermined amount of potassium permanganate ($KMnO_4$) to the graphite powder and $H_2SO_4$ mixture. In some embodiments, about 1 kilogram of graphite powder is used for every 50 liters $H_2SO_4$ in the graphite powder and $H_2SO_4$ mixture. In some embodiments, the $H_2SO_4$ ranges in concentration from about 96% to about 98%. In some embodiments, the predetermined amount of $KMnO_4$ is about 6 kilograms of $KMnO_4$ for every 1 kilogram of graphite powder. In some embodiments, agitating comprises stirring at a rate that ranges from about 50 rpm to about 150 rpm. In some embodiments, a predetermined time for agitating the graphite oxidizing mixture ranges from about 45 minutes to about 300 minutes. In some embodiments, cooling the graphite oxidizing mixture to the second predetermined temperature is achieved by quenching the graphite oxidizing mixture. In some embodiments, cooling the graphite oxidizing mixture to the second predetermined temperature is achieved by quenching the graphite oxidizing mixture with water and/or ice. In some embodiments, second predetermined temperature is about 0° C. In some embodiments, the second predetermined temperature ranges from about 0° C. to about 10° C. In some embodiments, the $H_2O_2$ is an aqueous solution having a concentration of about 30%. In some embodiments, the predetermined amount of the aqueous solution having a concentration of about 30% $H_2O_2$ is about 1 liter for every 10 liters of $H_2SO_4$. In some embodiments, $H_2SO_4$ is an aqueous solution having a concentration between about 96% and 98%.

A second aspect provided herein is a method for producing reduced graphite oxide comprising steps of: providing an aqueous solution comprising graphite oxide; heating the aqueous solution comprising graphite oxide to a first predetermined temperature; adding hydrogen peroxide ($H_2O_2$) to the aqueous solution over a period of about 1 hour while maintaining the first predetermined temperature, thereby forming a first mixture; heating the first mixture at the first predetermined temperature for about 3 hours; adding sodium ascorbate over a period of about 30 minutes, thereby forming a second mixture; heating the second mixture at the first predetermined temperature about 1.5 hours to yield the reduced graphite oxide.

In some embodiments, the first predetermined temperature is about 90° C. In some embodiments, the reduced graphite oxide comprises porous carbon sheet(s) (PCS). In some embodiments, the graphite oxide in the aqueous solution is a graphene oxide.

Those skilled in the art will appreciate the scope of the present disclosure and realize additional aspects thereof after reading the following detailed description in association with the accompanying drawings.

BRIEF DESCRIPTION OF THE DRAWINGS

Novel features of the disclosure are set forth with particularity in the appended claims. A better understanding of the features and advantages of the present disclosure will be obtained by reference to the following detailed description that sets forth illustrative embodiments, in which the principles of the embodiments are utilized, and the accompanying drawings or figures (also "FIG." and "FIGS." herein), of which:

DETAILED DESCRIPTION

The methods herein may include procedures of making oxidized forms of carbon-based materials, procedures of making materials derived from the oxidized forms of carbon-based materials, or both. In some embodiments, the methods herein may include procedures of making oxidized forms of graphite, procedures of making materials derived from the oxidized forms of graphite, or both. The methods herein comprise procedures of making graphene/graphite oxide (GO) and reduced graphene/graphite oxide (rGO). In some embodiments disclosed herein, GO is formed from graphite in a first reaction comprising oxidation, is treated (e.g., filtered/purified, concentrated, etc.), and may be reduced (e.g., to graphene, ICCN, or any other materials derived through reduction of GO) in a second reaction. In some embodiments, the second reaction comprises reduction, wherein, for example, a GO may be reduced to form graphene, ICCN and/or other reduced forms of GO, collectively referred to herein as reduced graphite or graphene oxide (rGO).

Those skilled in the art will recognize improvements and modifications to the present disclosure. All such improvements and modifications are considered within the scope of the concepts disclosed herein.

Current Methods of Synthesizing Carbon-Based Oxide and Reduced Carbon-Based Oxide Materials Existing methods for production of carbon-based oxide (CBO) and reduced carbon-based oxide (rCBO) materials include the Hummers method, the modified Hummers method, and various modifications thereof. Such methods are referred to herein as Hummers-based methods. Recognized herein are limitations associated with the Hummers-based methods.

In some embodiments, Hummers-based methods may be currently exhibit a low throughput, high cost, high waste quantities, and low reliability. In an example, a Hummers-based method takes about 2 months, requires several weeks of purification, costs about $93/kg, comprises expensive hydrochloric acid (HCl) washes, requires a certain technique that is left to the judgment of the individual scientist, and synthesizes a product that is often unacceptable for forming consumer grade products.

Figure 1:
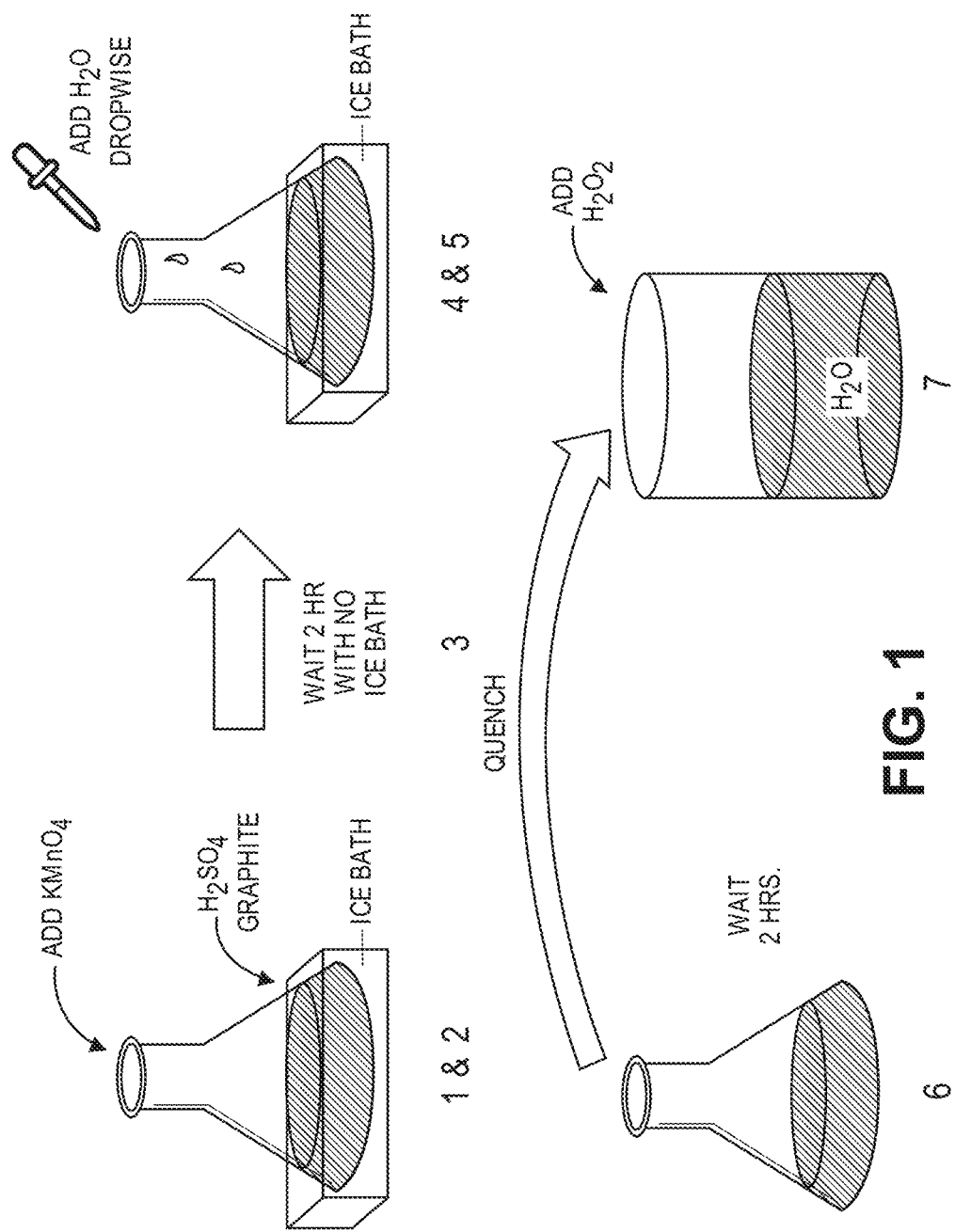
FIG. 1 illustratively depicts a diagram of a first exemplary method of producing carbon-based oxide (CBO) or reduced carbon-based oxide (rCBO) materials, per embodiments described herein.

An exemplary Hummers-based method, per FIG. 1, comprises:
1. Adding 15 grams (g) graphite to 750 milliliters (mL) concentrated sulfuric acid into a reaction flask that is kept at 0° C. using ice bath.
2. Adding 90 g potassium permanganate ($KMnO_4$) to the graphite and sulfuric acid (exothermic).
3. Removing the reaction flask from ice bath for 2 hours.
4. Returning the reaction flask into ice bath.
5. Adding 1.5 liters (L) of water ($H_2O$) drop-wise over the course of about 1-1.5 hours while maintaining a reaction temperature at 45° C. (controlling the temperature by the rate of addition of water and by adding ice to a melting ice bath).
6. Removing the reaction flask from ice bath for 2 hours.
7. Quenching the reaction with 4.2 L $H_2O$ and then 75 mL 30% hydrogen peroxide ($H_2O_2$).
8. Purifying with five HCl washes, followed by nine $H_2O$ washes, allowing the solution to air dry for about 2 weeks, rehydrating the dried graphite oxide with water, and 2 weeks of dialysis.

Methods of Synthesizing Carbon-Based Oxide and Reduced Carbon-Based Oxide Materials The method of the present disclosure provides for a faster, safer, cheaper, and consistent procedure for synthesizing CBO and rCBO materials. In some embodiments, the present disclosure provides procedures or methods for synthesizing graphite oxide and reduced graphite oxide (e.g., graphene, PCS, or ICCN). In contrast with other methods of making graphite oxide, the method of the present disclosure is capable of tuning the oxidation characteristics and the amount of exfoliation, is safer than other methods because the lower reaction temperatures reduce the risk of explosion, reduces the of reagents, enables expedited purification without the use of costly HCl, is configured to be fully scalable, enables increased throughput, and synthesizes a product the mechanical and electrical characteristics of which are consistent and tunable and which can be efficiently and accurately light or laser scribed.

In some embodiments, the methods described herein for synthesizing CBO and rCBO materials are safer because one or more of the reactions are performed at a temperature of less than 45° C., wherein the reactions of current methods may exceed 75° C.

In some embodiments, the method of the present disclosure is capable of synthesizing at least about 1 pound per day of a CBO or a rCBO material, including the time for purification. In some embodiments, the process is limited only by the size of the reactor, which enables the production of CBO and rCBO materials on the ton scale. In some embodiments, the methods described herein for synthesizing CBO and rCBO materials takes less than or equal to 1 week, wherein current methods require 2, 5 or 8 times as much time. In one example, the methods described herein for synthesizing CBO and rCBO materials costs about $21/kg, wherein currently available methods cost about $93/kg (a difference of more than fourfold). Further, in some embodiments, the method described herein forms less waste per mass of the CBO or rCBO materials than other methods.

In some embodiments, the method of the present disclosure provides a CBO or rCBO material whose composition (e.g., C:O atomic ratio, quantity of oxygen functionality, etc.) and/or morphology is repeatable to within about 1%, 2%, 3%, 4%, 5%, 6%, 7%, 8%, 9%, or 10% over a range of samples. In one example, the method of the present disclosure is capable of producing a GO with a C:O atomic ratio repeatable to within about 1%, 2%, 3%, 4%, 5%, 6%, 7%, 8%, 9%, or 10% over a number of batches and samples. In some embodiments, the improved reliability of the method described herein may be due to the lower reaction temperature.

In some embodiments, a method for synthesizing a CBO material (e.g., GO or PCS) comprises oxidation (first reaction), a first purification, reduction (second reaction), and a final purification. In some embodiments, a method for synthesizing an rCBO material (e.g., rGO) comprises oxidation, purification, reduction, and final purification.

In some embodiments, the process of oxidizing a carbon-based comprises a first reaction comprising: mixing graphite powder and sulfuric acid ($H_2SO_4$) while cooling the graphite powder and $H_2SO_4$ mixture to a first predetermined temperature; adding a predetermined amount of potassium permanganate ($KMnO_4$) to the graphite powder and $H_2SO_4$ mixture to form a graphite oxidizing mixture; agitating the graphite oxidizing mixture for a predetermined amount of time (e.g., after the addition of the predetermined amount of $KMnO_4$ has been completed); cooling the graphite oxidizing mixture to a second predetermined temperature; and adding a predetermined amount of hydrogen peroxide $H_2O_2$ and/or ice to the graphite oxidizing mixture to yield graphite oxide.

In some embodiments, the sulfuric acid and the graphite are premixed to minimize graphite dust, and are added to the reactor rapidly. In some embodiments, the mixing speed during one or more reaction processes is about 100 rpm. In some embodiments, a reaction is chilled by one or more cooling coils, ice, water, a coolant, or any combination thereof. In some embodiments, the volumes, quantities, masses, and time periods may be suitably scaled for production on a large scale.

In some embodiments, the first predetermined temperature resulting from cooling the graphite powder and $H_2SO_4$ mixture is about 0° C. In some embodiments, the first predetermined temperature resulting from cooling the graphite powder and $H_2SO_4$ mixture is about −10° C. to about 15° C. In some embodiments, the first predetermined temperature resulting from cooling the graphite powder and $H_2SO_4$ mixture is greater than or equal to about −10° C., −9° C., −8° C., −7° C., −6° C., −5° C., −4° C., −3° C., −2° C., −1° C., or 0° C. but less than or equal to about 1° C., 2° C., 3° C., 4° C., 5° C., 6° C., 7° C., 8° C., 9° C., 10° C., 11° C., 12° C., 13° C., 14° C., or 15° C.

In some embodiments, the potassium permanganate is added to the graphite powder and $H_2SO_4$ mixture at a set rate to keep the exothermic (e.g., self-heated) reaction temperature below about 15° C. In some embodiments, the reaction temperature of the graphite oxidizing mixture while adding the predetermined amount of $KMnO_4$ to the graphite powder and $H_2SO_4$ mixture is less than or equal to about 15° C., 14° C., 13° C., 12° C., 11° C., 10° C., 9° C., 8° C., 7° C., 6° C., 5° C., 4° C., 3° C., 2° C., or 1° C. In some embodiments, the reaction temperature of the graphite oxidizing mixture while the predetermined amount of $KMnO_4$ is added to the graphite powder and $H_2SO_4$ mixture is less than about 15° C.

In some embodiments, the agitating may comprise stirring at a stirring rates of about 50 revolutions per minute (rpm) to about 150 rpm. In some embodiments, the agitating may include stirring at a rate of at least about 50 rpm, 60 rpm, 70 rpm, 80 rpm, 90 rpm, 100 rpm, 110 rpm, 120 rpm, 130 rpm, 140 rpm, or 150 rpm. In some embodiments, the agitating may comprise stirring at a stirring rates of less than about 150 rpm. In some embodiments, the predetermined time for agitating the graphite oxidizing mixture is about 45 minutes to about 300 minutes. In some embodiments, the predetermined time for agitating the graphite oxidizing mixture is at least about 45 minutes, 50 minutes, 60 minutes, 70 minutes, 80 minutes, 90 minutes, 100 minutes, 120 minutes, 140 minutes, 160 minutes, 180 minutes, 200 minutes, 220 minutes, 240 minutes, 260 minutes, 280 minutes, or 300 minutes. In some embodiments, the predetermined time for agitating the graphite oxidizing mixture is at least between 45 minutes and 60 minutes, 60 minutes and 120 minutes, 120 minutes and 180 minutes, 180 minutes and 260 minutes, and 260 minutes and 300 minutes. In some embodiments, the predetermined time may or may not depend upon the stirring rate. In some embodiments, the predetermined time is independent of the stirring rate beyond a given threshold (e.g., a minimum stirring rate) and/or within a given range of stirring rates. In some embodiments, the reaction temperature of the graphite oxidizing mixture during the agitating is maintained below about 45° C. In some embodiments, the reaction temperature of the graphite oxidizing mixture during the agitating is maintained at less than or equal to about 15° C.

In some embodiments, cooling the graphite oxidizing mixture to the second predetermined temperature is achieved by quenching the graphite oxidizing mixture. In some embodiments, cooling the graphite oxidizing mixture to the second predetermined temperature is achieved by quenching the graphite oxidizing mixture with water, ice, a cooling coil, a coolant, or any combination thereof. In some embodiments, the second predetermined temperature is about 0° C. In some embodiments, the second predetermined temperature is about 0° C. to about 10° C. In some embodiments, the second predetermined temperature is greater than or equal to about 0° C. but less than or equal to about 1° C., 2° C., 3° C., 4° C., 5° C., 6° C., 7° C., 8° C., 9° C., or 10° C.

In some embodiments, the first reaction (oxidation) of the method provided herein for synthesizing a single-layer CBO or rCBO comprises: mixing graphene and sulfuric acid; chilling the solution; adding potassium permanganate powder; cooling the reaction; adding crushed ice to the reaction; stirring the solution; and quenching the reaction. In these embodiments, the graphite comprises 325sh natural flake graphite. In one example, about 32 L of 98% sulfuric acid and about 4.8 kg of potassium permanganate powder is used for every kilogram of graphite. In one example, the temperature of the solution is maintained by one or more cooling coils, wherein the reaction temperature is maintained at about −10° C. by setting the cooling coils' temperature to −2° C. In these embodiments, the potassium permanganate powder is adding over a period of about 1.5 hours, while maintaining a reaction temperature of below about 15° C. In one example, the temperature of the solution is maintained by one or more cooling coils, wherein the reaction temperature is allowed to heat up to about 20-30° C. over about 1.5 to about 2 hours by raising the reaction coil temperature to about 12° C. In one example, the temperature of the solution is maintained by one or more cooling coils, wherein the reaction temperature is further maintained at about 30° C. for approximately 30 minutes by cooling the reaction coils to about −2° C. In these embodiments, the about 32 kg of crushed ice is added to the reaction over the course of about 1 hour, wherein the reaction temperature climbs to about 50° C. In these embodiments, the solution is stirred or agitated for about 1 hour. In these embodiments, quenching the reaction is performed by adding about 72 kg of ice and/or 30% hydrogen peroxide (about 2 L) per kilogram of graphite, to stop and neutralize the reaction.

In some embodiments, the first reaction (oxidation) of the method provided herein to produce a multi-layer CBO or rCBO comprises: mixing graphene and sulfuric acid to form a solution; chilling the solution; adding potassium permanganate powder to the solution; stirring the solution and the potassium permanganate; and quenching the reaction. In this embodiment, the graphite is highly exfoliated, milled, small flake, large surface area, 9 micron flake sized, or any combination thereof. In these embodiments, about 25 L of 98% sulfuric acid and about 2 kg of potassium permanganate powder are used per kilogram of graphite. In one example, the temperature of the solution is maintained by one or more cooling coils, wherein the solution is chilled to a temperature of about −10° C. by setting the cooling coils to about −2° C. In one example, the potassium permanganate powder is adding over a period of about 45 minutes to about 1.5 hours to keep the reaction temperature below about 15° C. In these embodiment, the potassium permanganate, graphite, and sulfuric acid react for a period of time of about 30 minutes at reaction temperature of about 15° C. In these embodiments, the solution is stirred or agitated for about 30 minutes at a reaction temperature of about 15° C. In these embodiments, quenching the reaction is performed by adding about 125 kg of ice and/or 1 L of 30% hydrogen peroxide to stop and neutralize the reaction.

In some embodiments, the first purification step after the first reaction comprises a first filtration which removes impurities, such as sulfuric acid, manganese oxides, and manganese sulfate, and increases the pH of the solution to at least about 5. In some embodiments, the first purification step comprises rinsing the GO with water (e.g., deionized water), purifying the graphite oxide by chemistry dialysis, or a combination thereof (e.g., rinsing followed by dialysis). In some embodiments, the sulfuric acid concentration of the CBO after the first reaction is about 30% or about 60% for a single-layer or multi-layer CBO/rCBO, respectively, corresponding to a pH of approximately 0. In some embodiments, filtration is complete when the pH of the solution is about 5, corresponding to an acid concentration of about 0.00005%. In some embodiments, the first filtration comprises post-oxidation purification. In some embodiments, the concentration of GO in the solution after filtration is about 1% by mass (e.g., 1 kg GO in 100 L of aqueous solution).

In some embodiments, the CBO or rCBO is concentrated after purification to remove water and/or acid, to form a solution of, for example, 1% GO by weight. In some embodiments a given GO percentage by weight is required for certain applications, and to form dry powders and aqueous solutions.

In some embodiments, the reduction of CBO or GO to form rCBO or rGO, respectively, comprises a second reaction. In some embodiments, the second reaction comprises heating the CBO to about 90° C. and adding hydrogen peroxide over the course of about an hour. In some embodiments, the second reaction further comprises adding sodium ascorbate (e.g., $C_6H_7NaO_6$) over the course of about 30 minutes to about 60 minutes. In one example, the second reaction uses about 1 L to about 2 L of 30% hydrogen peroxide, and about 5 kg of sodium ascorbate (sodium salt of ascorbic acid) per kg of GO in about 100 liters of. In some embodiments, the reaction continues to heat at about 90° C. for about 1.5 to about 3 more hours, before the addition of sodium ascorbate. In some embodiments, the reaction continues to heat at about 90° C. for a time period of about 1.5 hours, wherein the reaction occurs at a temperature of 90° C. for about 6 hours.

In some embodiments, the concentration of the GO by mass in the solution prior to the second reaction is about 0% to about 2% (e.g., 0-2 kg/100 L of aqueous solution). In some embodiments, the concentration of GO by mass is between about 0% and 0.5%, 0% and 1%, 0% and 1.5%, 0% and 2%, 0.5% and 1%, 0.5% and 1.5%, 0.5% and 2%, 1% and 1.5%, 1% and 2%, or 1.5% and 2%. In some embodiments, the concentration of GO by mass is less than about 2%, 1.5%, 1%, 0.5%, 0.25%, 0.1% or less. In some embodiments, the concentration of the GO is limited by the quantity of GO that may be dissolved in water while maintaining the fluidity required for manufacturing. In some embodiments, the solution becomes viscous at a concentration of 2% or more, (i.e., 2 kg or more of GO in 100 L of water). In some embodiments, a higher concentration (e.g., 1% by mass) reduces the required volume of water, which may decrease filtration time because the larger the volume of the solution, the longer the filtration process. In some embodiments, a quantity of water is filtered out at the end of the second reaction In some embodiments, the volume 30% hydrogen peroxide per kilogram of GO is between about 10 L and 100 L, or between about 1 kg and 10 kg. In some embodiments, the volume of hydrogen peroxide per kilogram of GO (e.g., with a concentration of about 30% by weight) is between about 10 L and 20 L, 10 L and 30 L, 10 L and 40 L, 10 L and 50 L, 10 L and 60 L, 10 L and 70 L, 10 L and 80 L, 10 L and 90 L, 10 L and 100 L, 20 L and 30 L, 20 L and 40 L, 20 L and 50 L, 20 L and 60 L, 20 L and 70 L, 20 L and 80 L, 20 L and 90 L, 20 L and 100 L, 30 L and 40 L, 30 L and 50 L, 30 L and 60 L, 30 L and 70 L, 30 L and 80 L, 30 L and 90 L, 30 L and 100 L, 40 L and 50 L, 40 L and 60 L, 40 L and 70 L, 40 L and 80 L, 40 L and 90 L, 40 L and 100 L, 50 L and 60 L, 50 L and 70 L, 50 L and 80 L, 50 L and 90 L, 50 L and 100 L, 60 L and 70 L, 60 L and 80 L, 60 L and 90 L, 60 L and 100 L, 70 L and 80 L, 70 L and 90 L, 70 L and 100 L, 80 L and 90 L, 80 L and 100 L, or 90 L and 100 L. In some embodiments, the volume of hydrogen peroxide (e.g., with a concentration of about 30% by weight) per 1 kg GO is greater than or equal to about 10 L, 20 L, 30 L, 40 L, 50 L, 60 L, 70 L, 80 L, 90 L, or 100 L of hydrogen peroxide (e.g., with a concentration of about 30% by weight). In some embodiments, the volume of hydrogen peroxide (e.g., with a concentration of about 30% by weight) per 1 kg GO is less than about 100 L, 90 L, 80 L, 70 L, 60 L, 50 L, 40 L, 30 L, 20 L, or 15 L of hydrogen peroxide (e.g., with a concentration of about 30% by weight). In some embodiments, a volume of hydrogen peroxide equivalent to any of the aforementioned amounts of the 30% solution is added as a solution with a different concentration, or in concentrated or pure form (e.g., 90%-100% by weight). In some embodiments, the amount of hydrogen peroxide equivalent to any of the aforementioned amounts of the 30% solution is expressed in terms of volume based on a 100% (or pure) solution. In some embodiments, the amount of hydrogen peroxide equivalent to any of the aforementioned amounts of the 30% solution is expressed in terms of moles or in terms of weight of hydrogen peroxide (e.g., between about 3 kg (or 88 moles) and 30 kg (or 882 moles) of (pure) $H_2O_2$ is provided per 1 kg GO). In some embodiments, the amount of hydrogen peroxide equivalent to any of the aforementioned amounts of the 30% solution is expressed as a weight basis of pure hydrogen peroxide per 1 kg GO of between about 3 kg and 6 kg, 3 kg and 9 kg, 3 kg and 12 kg, 3 kg and 15 kg, 3 kg and 18 kg, 3 kg and 21 kg, 3 kg and 24 kg, 3 kg and 27 kg, 3 kg and 30 kg, 6 kg and 9 kg, 6 kg and 12 kg, 6 kg and 15 kg, 6 kg and 18 kg, 6 kg and 21 kg, 6 kg and 24 kg, 6 kg and 27 kg, 6 kg and 30 kg, 9 kg and 12 kg, 9 kg and 15 kg, 9 kg and 18 kg, 9 kg and 21 kg, 9 kg and 24 kg, 9 kg and 30 kg, 12 kg and 15 kg, 12 kg and 18 kg, 12 kg and 21 kg, 12 kg and 24 kg, 12 kg and 27 kg, 12 kg and 30 kg, 15 kg and 18 kg, 15 kg and 21 kg, 15 kg and 24 kg, 15 kg and 30 kg, 18 kg and 21 kg, 18 kg and 24 kg, 18 kg and 27 kg, 18 kg and 30 kg, 21 kg and 24 kg, 21 kg and 27 kg, 21 kg and 30 kg, 24 kg and 27 kg, 24 kg and 30 kg, or 27 kg and 30 kg. In some embodiments, the amount of pure hydrogen peroxide per 1 kg GO equivalent to any of the aforementioned amounts of the 30% solution is expressed as a weight basis, greater than or equal to about 3 kg, 6 kg, 9 kg, 12 kg, 15 kg, 18 kg, 21 kg, 24 kg, or 30 kg. In some embodiments, the amount of pure hydrogen peroxide per 1 kg GO equivalent to any of the aforementioned amounts of the 30% solution is expressed as a weight basis as less than about 30 kg, 24 kg, 21 kg, 18 kg, 15 kg, 12 kg, 9 kg, 6 kg, or 4.5 kg.

In some embodiments, the mass of sodium ascorbate per 1 kg of GO is between about 1 kg and 10 kg, between about 1 kg and 2 kg, 1 kg and 3 kg, 1 kg and 4 kg, 1 kg and 5 kg, 1 kg and 6 kg, 1 kg and 7 kg, 1 kg and 8 kg, 1 kg and 9 kg, 1 kg and 10 kg, 2 kg and 3 kg, 2 kg and 4 kg, 2 kg and 5 kg, 2 kg and 6 kg, 2 kg and 7 kg, 2 kg and 8 kg, 2 kg and 9 kg, 2 kg and 10 kg, 3 kg and 4 kg, 3 kg and 5 kg, 3 kg and 6 kg, 3 kg and 7 kg, 3 kg and 8 kg, 3 kg and 9 kg, 3 kg and 10 kg, 4 kg and 5 kg, 4 kg and 6 kg, 4 kg and 7 kg, 4 kg and 8 kg, 4 kg and 9 kg, 4 kg and 10 kg, 5 kg and 6 kg, 5 kg and 7 kg, 5 kg and 8 kg, 5 kg and 9 kg, 5 kg and 10 kg, 6 kg and 7 kg, 6 kg and 8 kg, 6 kg and 9 kg, 6 kg and 10 kg, 7 kg and 8 kg, 7 kg and 9 kg, 7 kg and 10 kg, 8 kg and 9 kg, 8 kg and 10 kg, or 9 kg and 10 kg. In some embodiments, the mass of sodium ascorbate per 1 kg GO is greater than or equal to about 1 kg, 2 kg, 3 kg, 4 kg, 5 kg, 6 kg, 7 kg, 8 kg, 9 kg, or 10 kg. In some embodiments, the mass of sodium ascorbate per 1 kg GO is less than about 15 kg, 14 kg, 13 kg, 12 kg, 11 kg, 10 kg, 9 kg, 8 kg, 7 kg, 6 kg, 5 kg, 4 kg, 3 kg, 2 kg, or 1.5 kg.

In some embodiments, the reaction temperature during the second reaction is about 60° C. to about 180° C. In some embodiments, the reaction temperature during the second reaction comprises at a variety of temperatures or a constant temperature. In some embodiments, the reaction temperature during the second reaction is between about 60° C. and 80° C., 60° C. and 90° C., 60° C. and 100° C., 60° C. and 120° C., 60° C. and 140° C., 60° C. and 160° C., 60° C. and 180° C., 80° C. and 90° C., 80° C. and 100° C., 80° C. and 120° C., 80° C. and 140° C., 80° C. and 160° C., 80° C. and 180° C., 90° C. and 100° C., 90° C. and 120° C., 90° C. and 140° C., 90° C. and 160° C., 90° C. and 180° C., 100° C. and 120° C., 100° C. and 140° C., 100° C. and 160° C., 100° C. and 180° C., 120° C. and 140° C., 120° C. and 160° C., 120° C. and 180° C., 140° C. and 160° C., 140° C. and 180° C., or 160° C. and 180° C. In some embodiments, the reaction temperature during the second reaction is or is not allowed to change or fluctuate within a given range (e.g., the temperature for a given step is kept constant at a given temperature within a given range or may fluctuate within the given range). In some embodiments, (e.g., at temperatures above about 100° C.), the reaction chamber is sealed.

In some embodiments, a percentage of the GO that is converted (hereafter referred to as "y") is at least about 90%, 95%, 98%, 99%, 99.5%, or 100%. In some embodiments, between 90% and 95% by weight of the GO is converted. In other embodiments, between 95% and 95.5% by weight of the GO is converted. In some embodiments, the amount of rGO produced per unit of GO depends on the oxygen content of the GO and the rGO. In some embodiments, the C:O atomic ratio of the GO is between about 4:1 and 5:1, and the oxygen content of the rGO is less than or equal to about 5 atomic percent. In some embodiments, the weight of rGO produced per kilogram of GO is between about 0.75y kilograms and 0.84 kilograms. In some embodiments, the C:O atomic ratio of the GO is between about 7:3 and 5:1, wherein the oxygen content of the rGO is less than or equal to about 5 atomic percent. In some embodiments, the amount of rGO produced per mass unit of GO is between about 0.64y and 0.84. In some embodiments, the C:O atomic ratio of the GO is at least about 7:3, wherein the oxygen content of the rGO is less than or equal to about 5 atomic percent. In some embodiments, the amount of rGO produced per mass unit of GO is at least about 0.64y. In some embodiments, the amount of rGO produced per mass unit of GO is at least about 0.5, 0.55, 0.6, 0.65, 0.7, 0.75, or 0.8. In some embodiments, the amount of rGO produced per mass unit of GO is between about 0.5 and 0.85, 0.6 and 0.8, or 0.7 and 0.8 units of rGO.

In some embodiments, the second reaction is performed separately from the first reaction. For example, the second reaction followed by a second filtration, may be performed using any graphite oxide feedstock with suitable specifications.

In some embodiments, a second filtration or purification is performed after the second reaction to remove such impurities as, for example, sodium ascorbate, sulfuric acid, manganese oxides, and manganese salts and other salts.

In some embodiments, the purification comprises washing the rGO solution with de-ionized (DI) water (e.g., with copious amounts of DI water) until the conductivity of the rGO solution reaches about 50 microsiemens per centimeter (μS/cm) or less. In some embodiments, the rGO solution contains about 4.95 kg of sodium ascorbate per kg of rGO and has a conductivity of greater than about 200 mS/cm. In some embodiments, for some uses a specific concentration may be required for some processes that use rGO, such as about 2% by weight or greater.

In some embodiments, the purification comprises tangential flow filtering until the product has a pH of about 5. In some embodiments, the filter is a modified polyether sulfone hollow filter membrane with about 0.02 micron pore size. The purified GO may then be concentrated to a solution of about 1% by weight.

In some embodiments, purification comprises vacuum filtration through, for example, a 2 micron 316 stainless steel mesh filter, wherein water is flushed through the rGO to remove all salts. In some embodiments, Purification is complete when the rGO solution has a conductivity of about 50 μS/cm or less.

In some embodiments, the mixing speed or stirring rate (e.g., during one or more reaction processes) is about 200 rpm. In some embodiments, the mixing speed is at least about 100 rpm, 110 rpm, 120 rpm, 130 rpm, 140 rpm, 150 rpm, 160 rpm, 170 rpm, 180 rpm, 190 rpm, or 200 rpm. In some embodiments, the mixing speed is between about 100 rpm and about 150 rpm. In another embodiment, the mixing speed is between about 150 rpm and about 200 rpm.

In some embodiments, product synthesized when the first and second reactions are performed below ambient reaction temperature show improved capacitance, wherein the methods thereby are safer and more controlled. In some embodiments, an ambient reaction temperature comprises a reaction performed in room temperature surroundings without external cooling. The reaction conditions include Rainbow Reactions (RR) that are time variable reactions so named due to a spectrum of colors produced during synthesis. In some embodiments, a first Rainbow Reaction RR 1, a second Rainbow Reaction RR 2, and a third Rainbow reaction RR 3, or any combination thereof, per FIG. 2, comprise ambient reactions. In some embodiments, below ambient reactions further increase product performance and method stability and accuracy.

Figure 2:
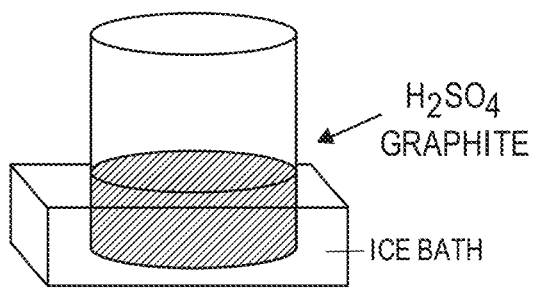
FIG. 2 illustratively depicts a diagram of a second exemplary method of producing CBO or rCBO materials, per embodiments described herein.
Figure 2:
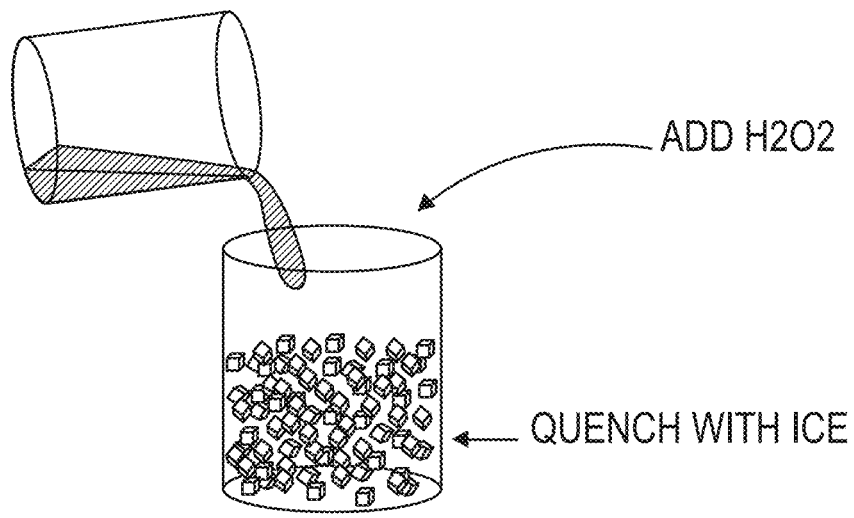
Figure 3:
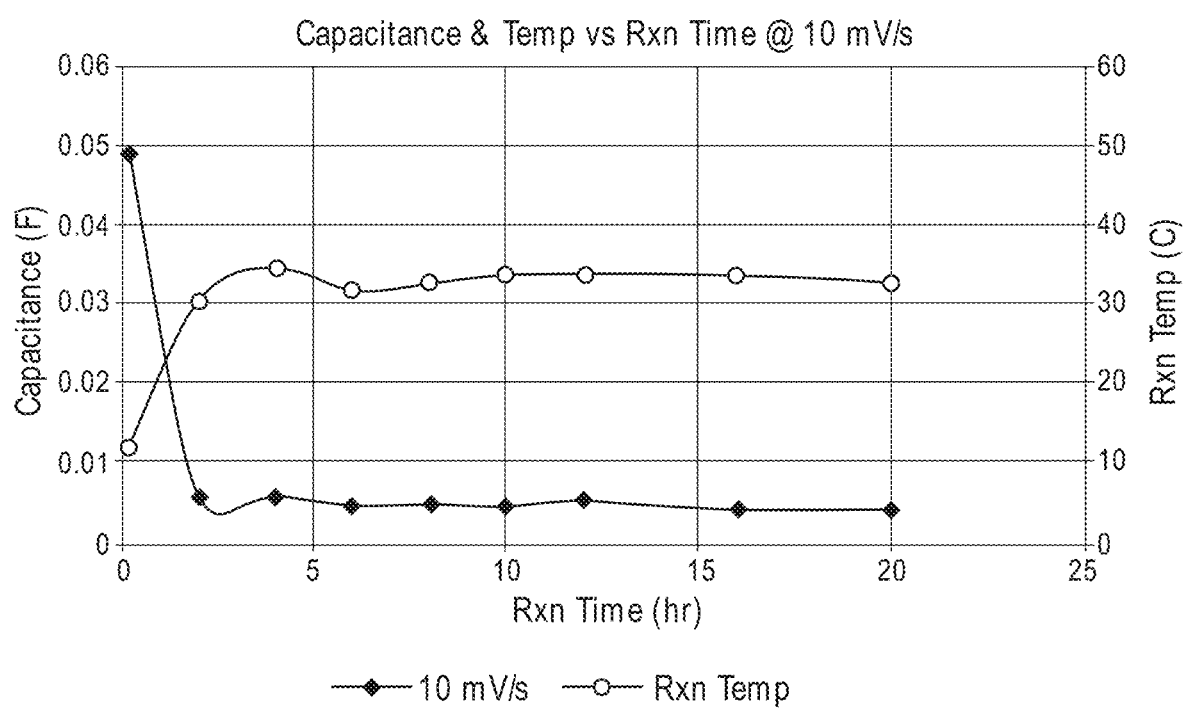
FIG. 3 is an exemplary graph showing the relationship between the capacitance and the reaction time, and the relationship between the reaction temperature and the reaction time, per embodiments described herein.

In one example a method for synthesizing a CBO or rCBO material, per FIG. 2, comprises the following time variable RRs:

RR 1) Forming a solution of graphite and concentrated sulfuric acid at about 0° C. using ice bath or cooling coils.

RR 2) Adding $KMnO_4$ (exothermic) while maintain a reaction temperature of below about 15° C. using an ice bath or cooling coils.

RR 3) Stirring the reaction for about 45 minutes.

RR 4) Quenching the reaction by adding ice and/or 30% $H_2O_2$ to the reaction mixture.

RR 5) Purifying the graphite oxide with one or more $H_2O$ washes, followed by about 1 week of continuous-flow dialysis.

In one example, the mass of the graphite is about 15 g, the volume of the concentrated sulfuric acid is about 750 mL, the mass of the $KMnO_4$ is about 90 g, the mass of ice is at least about 2.6 g, and the volume of $H_2O_2$ is at least about 75 mL. In some embodiments, the graphite is provided in powder form. In an example, the total processing time is about 1 week, and the total cost is about \$21/kg of GO or rGO.

In some embodiments, the amount of oxidizing agent (also "oxidizer" herein) may be provided in terms of a ratio of oxidizing agent ($KMnO_4$) to graphite (also "Ox:Gr" herein). In one example, about 90 g $KMnO_4$ is used per 15 g graphite, corresponding to about 6× mass ratio Ox:Gr. In another example, about 75 mL 30% $H_2O_2$ (e.g., about 30% by weight in aqueous solution, corresponding to about 0.66 moles $H_2O_2$) is used (i) per 90 g $KMnO_4$, corresponding to about 0.25 units of $H_2O_2$ per unit of $KMnO_4$ on a weight basis or about 1.16 units of $H_2O_2$ per unit of $KMnO_4$ on a molar basis, or (ii) per 750 mL concentrated sulfuric acid with a concentration of between about 96% $H_2SO_4$ and 98% $H_2SO_4$ (e.g., by weight in aqueous solution), corresponding to a volume ratio of 30% $H_2O_2$ to concentrated sulfuric acid of about 10:1 (e.g., about 1 liter of aqueous solution having about 30% $H_2O_2$ for every 10 liters of concentrated $H_2SO_4$). In yet another example, about 50 liters of concentrated $H_2SO_4$ is consumed for every 1 kilogram of graphite. Further examples of amounts and ratios are provided elsewhere herein, for example, in relation to methods for producing single-layer GO and multi-layer GO (e.g., on a per kilogram graphite oxide basis).

In some embodiments, the stirring time may vary, wherein the 45 minutes was selected based on the best measured sample. In some embodiments, the reaction temperature may vary with time according to specific cooling conditions (e.g., presence or absence of cooling by ice bath or cooling coils).

In some embodiments, RR 5 comprises at least 1, 2, 3, 4, 5 (e.g., 5) or more water washes. In some embodiments, the purification further comprises additional water purification processes, such as, for example, dialysis. In some embodiments, dialysis comprises placing the material in a porous tube and removing (e.g., leaching out) ions from the material through the walls of the tube into a water bath that is refreshed continuously or batch-wise. In some embodiments, the method comprises or further comprises one or more filtration methods other than dialysis (e.g., after the $H_2O$ washes, another filtration method may be applied in lieu of dialysis). In one example, the filtration process takes less than about 1 week, wherein the duration of the filtration may depend on batch size. For example, for a 15 g graphite batch, per above, filtration may take less than or equal to about 1 or 2 days. In one example, total filtration (e.g., dialysis) time may be less than or equal to about 7 days, 6 days, 5 days, 4 days, 3 days, 2 days, 1 day, or ½ day. In some embodiments, a shorter filtration time may reduce the total processing time to less than or equal to about 7 days, 6 days, 5 days, 4 days, 3 days, 2 days, 1 day, or ½ day.

In some embodiments, all of the graphite is converted to a CBO or an rCBO material. In some embodiments, the quantity of the CBO or the rCBO material that is produced per unit of graphite depends on the oxygen content of the CBO and the rCBO materials. In some embodiments, the weight of the CBO or rCBO materials produced is greater than the weight of the consumed graphene by a factor of about 1 to about 3 (e.g., 1.27 or 1.33). In some embodiments, the C:O atomic ratio of the CBO or the rCBO material is about 4:1 and 5:1, wherein the C:O atomic ratio of the GO may differ for single-layer and multi-layer CBO and the rCBO materials (e.g., as described in relation to FIG. 9). Thus, in some embodiments the amount of GO produced per unit of graphite may differ for single-layer and multi-layer CBO or rCBO.

In some embodiments, the concentration of one or more of the reactants varies. In an example, the concentration of the sulfuric acid is between about 96% and 98% by weight in aqueous solution. In some embodiments the quantity of $H_2O_2$ may be represented as a ratio between the mass of the $H_2O_2$ and the mass of the $KMnO_4$, which may affect the quantity of the manganese species within the CBO or rCBO. In other embodiments, the concentrations and quantities of the reactants may be represented by molar amounts. In some embodiments, employing concentrations of sulfuric acid below about 96% (e.g., by weight in aqueous solution) may alter the morphology of the CBO or rCBO, and/or reduce the concentration of oxygen-containing groups.

FIGS. 3, 4, 5, and 8 show characteristics of the CBO and rCBO. Per FIG. 3, as the RR 1 reaction is self-heated (exothermic), extended RR 1 reactions at higher temperatures synthesize CBO and rCBO materials with lower capacitances. Per FIG. 3, the capacitance of exemplary CBO and rCBO products are compared to their reaction temperature as functions of reaction time (in hours) at a scan rate of 10 millivolts per second (mV/s).

In one example, it was determined that the greatest capacitance at 10 mV/s and at 20 min of 49 mF/cm$^2$ occurs with a 6× Ox:Gr mass ratio and a reaction time of 0-20 hours. In this example, the peak capacitance for RR 1 was measured for an ICCN formed by light-scribing the GO produced by the method of FIG. 2. In some embodiments, the peak capacitance for RR 1 of the unreduced GO is about the same as for the rGO (ICCN).

Figure 4:
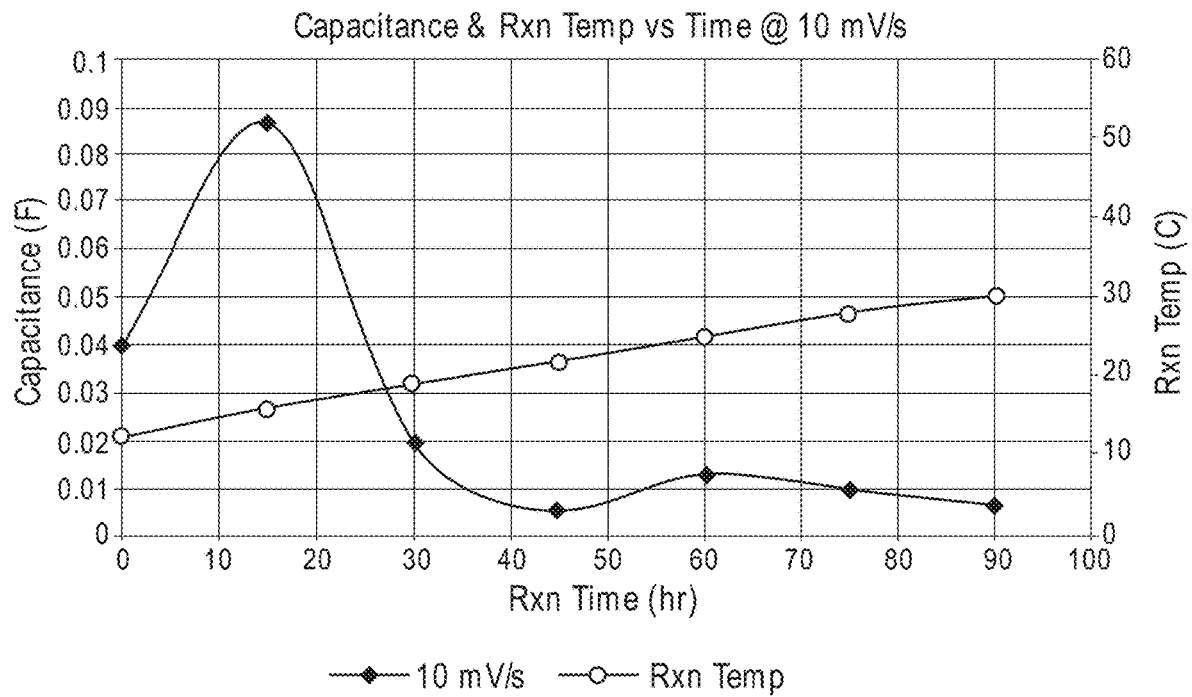
FIG. 4 is an exemplary graph showing the relationship between the capacitance and the reaction time, and the relationship between the reaction temperature and the reaction time, per embodiments described herein.

In some embodiments, per FIG. 4, shorter RR 2 reaction times led to higher capacitances, by retaining a more pristine sp2 structure of graphene with less oxidative damage. In some embodiments, the term sp2 is a hybridization of s, px, and py atomic orbitals to form a trigonal planar molecular configuration with 120 degree angles. In some embodiments, the optimal RR2 reaction occurred with a 6× mass ratio Ox:Gr, over 0-2 hours, which yielded a peak capacitance at about 10 mV/s and at about 15 minutes of about 87 mF/cm$^2$. In this example, the peak capacitance for RR 2 was measured for an ICCN formed by light-scribing the GO produced by the method of FIG. 2 with process #3 corresponding to RR 2. The peak capacitance for RR 2 of the unreduced GO is about the same as for the rGO (ICCN).

Figure 5:
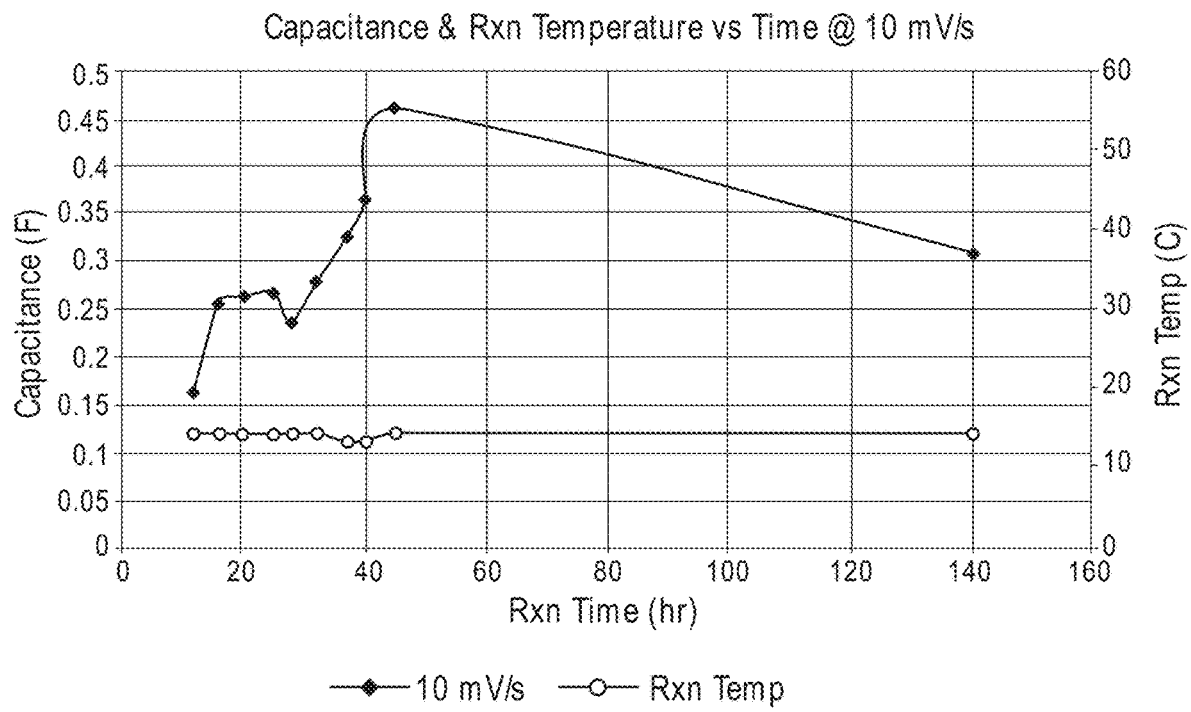
FIG. 5 is an exemplary graph showing the relationship between the capacitance and the reaction time, and the relationship between the reaction temperature and the reaction time, per embodiments described herein.

In some embodiments, colder reaction temperatures in RR 3, per FIG. 5, enabled a greater window of opportunity to quench the reaction at the right time. In some embodiments, the optimal RR3 reaction occurred with a 6× mass ratio Ox:Gr, and a reaction time to yield a product with a peak capacitance in about 10 mV/s at about 45 min of about 459 mF/cm$^2$. In this example, the peak capacitance for RR 3 was measured for an ICCN formed by light-scribing the GO produced by the method of FIG. 2 with step 3 corresponding to RR 2. The peak capacitance for RR 3 of the unreduced GO is about the same as for the rGO (ICCN).

Figure 8:
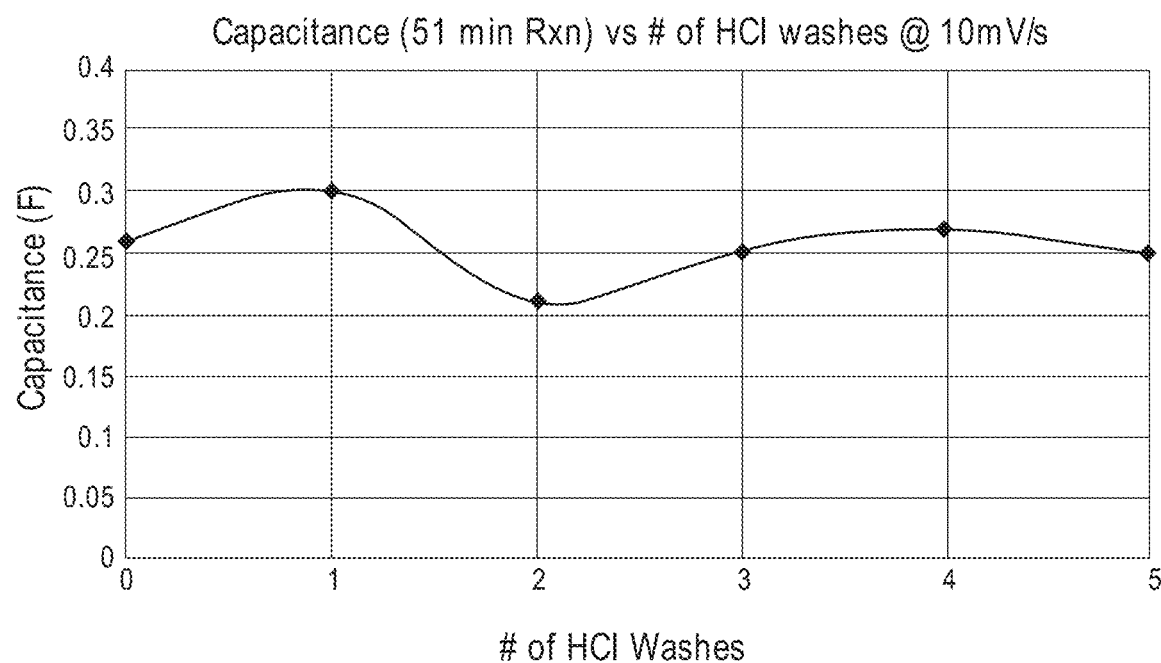
FIG. 8 displays an exemplary relationship between the number HCl washes and the capacitance of the CBO material, at a scan rate of 10 mV/s, per embodiments described herein.

In some embodiments, per FIG. 8, the use or the number of HCl washes in RR 5 may not have a significant effect on the capacitance of the CGO or the rCGO, whereas a capacitance variation of about 11% among the number of wash cycles, with no visible trend, was observed.

In some embodiments, optimal RR 5 conditions comprise a 6× mass ratio Ox:Gr, ice bath cooling for 0-1 hour with or without the use of one or more HCl washes, which achieved a peak capacitance at about 10 mV/s and about 31 min of about 261 mF/cm$^2$. In this example, the peak capacitance for RR 5 was measured for an ICCN formed by light-scribing the GO produced by a modified version of the method in FIG. 2. In some embodiments, the peak capacitance for RR 5 of the unreduced GO is about the same as for the rGO (ICCN).

In some embodiments, removal of HCl from the purification steps shows no loss of capacitance and significantly reduces the cost of the product, while expediting the purification procedure. Removal of HCl from the purification steps may provide one or more (any combination, or all) of the aforementioned advantages.

Carbon-Based Oxide or Reduced Carbon-Based Oxide Materials

Any aspects of the disclosure described in relation to graphene may equally apply to rGO (e.g., ICCN, or porous carbon sheet(s)) at least in some configurations, and vice versa. The rGO (e.g., graphene or ICCN) may be treated. In some embodiments, the rGO (e.g., ICCN) comprises a two-dimensional (2-D) material (e.g., porous carbon sheet(s)) or a three-dimensional (3-D) material (e.g., ICCN). In some embodiments, primarily two-dimensional or three-dimensional materials may be desirable for different applications and uses.

In some embodiments, an ICCN comprises a plurality of expanded and interconnected carbon layers, wherein the term "expanded," refers to a plurality of carbon layers that are expanded apart from one another, means that a portion of adjacent ones of the carbon layers are separated by at least about 2 nanometers (nm). In some embodiments, at least a portion of adjacent carbon layers are separated by greater than or equal to about 2 nm, 3 nm, 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, or 100 nm. In some embodiments, at least a portion of adjacent carbon layers are separated by less than about 3 nm, 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, or 100 nm. In some embodiments, at least a portion of adjacent carbon layers are separated by between about 2 nm and 10 nm, 2 nm and 25 nm, 2 nm and 50 nm, or 2 nm and 100 nm. In some embodiments, the plurality of carbon layers has an electrical conductivity greater than about 0.1 siemens per meter (S/m). In some embodiments, each of the plurality of carbon layers is a two-dimensional material with only one carbon atom of thickness. In some embodiments, each of the expanded and interconnected carbon layers may comprise at least one, or a plurality of corrugated carbon sheets that are each one atom thick.

Figure 9:
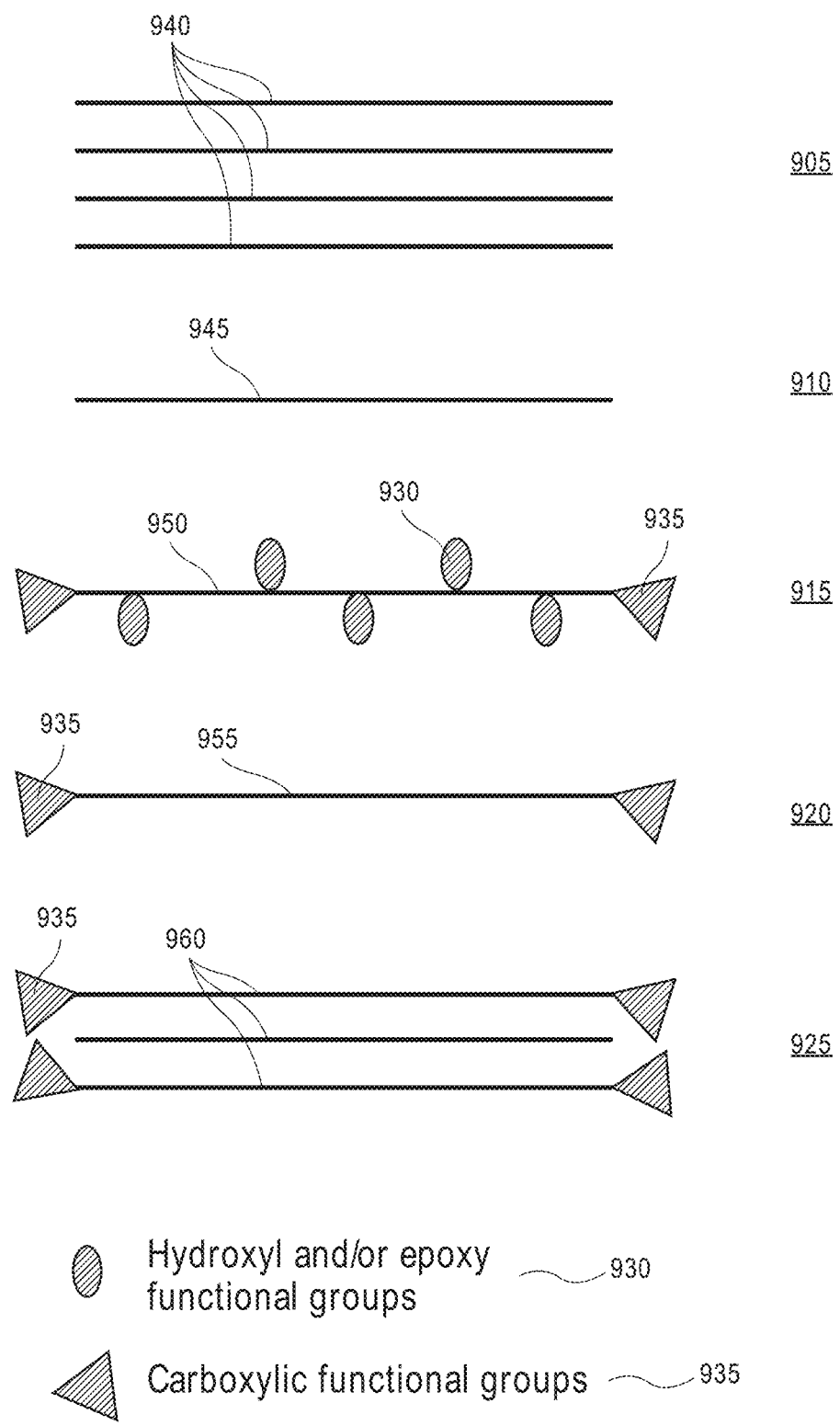
FIG. 9 illustratively depicts several carbon forms, per embodiments described herein.

FIG. 9 is an exemplary illustration of various carbon forms 905, 910, 915, 920, and 925, which may or may not comprise functional groups, and may be employed to synthesize an array of carbon-based materials. In some embodiments, a given carbon form comprises one or more hydroxyl and/or epoxy functional groups 930, one or more carboxylic functional groups 935, one or more other functional groups (e.g., carbonyl functional groups), or any combination thereof.

In some embodiments, the carbon form comprises graphite 905, wherein the graphite comprises a plurality of carbon sheets 940 (e.g., greater than or equal to about 100, 1,000, 10,000, 100,000, 1 million, 10 million, 100 million, or more) that are each one atom thick. In some embodiments, the plurality of carbon sheets 940 are stacked on top of each other and stick together due to van der Waals interactions, such that the interior of the stack is not accessible (e.g., only top and bottom sheets are accessible). In some embodiments, the carbon form 910 comprises graphene, which comprises a carbon sheet 945 that is one atom thick, and may comprise functional groups. In some embodiments, the carbon form 915 comprises graphene oxide (e.g., singular graphite oxide in solution), which comprises a carbon sheet 950 that is one atom thick.

In some embodiments, one or more carbon forms 915 may agglomerate, wherein individual carbon sheets 960 are separated, or may remain separated due to van der Waals interactions. In some embodiments, the carbon form 915 includes one or more hydroxyl and/or epoxy functional groups 930, and one or more carboxylic functional groups 935, wherein the hydroxyl and/or epoxy functional groups 930 are attached or otherwise associated with/bonded to the surfaces of the carbon sheet 950. In some embodiments, the carboxylic functional groups 935 is attached or otherwise associated with or bonded to the edges of the carbon sheet 950.

In some embodiments, the carbon form 920 comprises reduced graphene oxide (e.g., PCS formed in solution), comprising a carbon sheet 955 that is one atom thick. In some embodiments, the carbon form 920 comprises one or more carboxylic functional groups 935 which are attached or otherwise associated with or bonded to the edges of the carbon sheet 955.

In some embodiments, the carbon form 925 comprises two or more layers of graphene oxide (e.g., bilayer or trilayer graphite oxide in solution), wherein each carbon sheet or layer 960 is one atom thick, and wherein the two or more carbon sheets or layers 960 are held together by van der Waals interactions. In some embodiments, the number layer graphene oxide is greater than or equal to 2, 3, 4, 5, 6, 7, 8, 9, or 10 carbon sheets or layers 960 In some embodiments, the number layer graphene oxide is less than or equal to 10 carbon sheets or layers 960 (e.g., up to 10 carbon sheets or layers). In some embodiments, the number layer graphene oxide is between 2 and 3, 2 and 4, 2 and 5, 2 and 6, 2 and 7, 2 and 8, 2 and 9, 2 and 10, 3 and 4, 3 and 5, 3 and 6, 3 and 7, 3 and 8, 3 and 9, 3 and 10, 4 and 5, 4 and 6, 4 and 7, 4 and 8, 4 and 9, 4 and 10, 5 and 6, 5 and 7, 5 and 8, 5 and 9, 5 and 10, 6 and 7, 6 and 8, 6 and 9, 6 and 10, 7 and 8, 7 and 9, 7 and 10, 8 and 9, 8 and 10, or 9 and 10 carbon sheets or layers 960. In some embodiments, the number layer graphene oxide is 2 and 4, or 2 and 3 carbon sheets or layers 960. In some embodiments, the number layer graphene oxide is up to 4 carbon sheets or layers 960 In some embodiments, the number layer graphene oxide is 4 carbon sheets or layers 960.

In some embodiments, the carbon form 925 includes one or more carboxylic functional groups 935, wherein the carboxylic functional groups 935 are attached or otherwise associated with or bonded to edges of the one or more of the carbon sheets or layers 960. In some embodiments, the carboxylic functional groups 935 are primarily attached or bonded to the edges of the top and bottom carbon sheets or layers 960 in a stack of the carbon sheets or layers 960. In some embodiments, the carboxylic functional groups 935 may be attached to or otherwise associated with/bonded to edges of any (e.g., each, or at least 2, 3, 4, or more) of the carbon sheets or layers 960.

In some embodiments, the presence and quantity of functional groups impacts the overall carbon to oxygen (C:O) atomic ratio of the carbon forms seen in FIG. 9. For example, the carbon forms 925 and 915 may differ in the amount and/or type of oxygen functionality. In another example, the carbon form 925 may be produced upon oxidation of the carbon form 905, and the carbon form 925 may in turn be further oxidized to the carbon form 915. In some embodiments, each of the carbon forms in FIG. 9 may be produced via one or more pathways, and/or at least some of the carbon forms in FIG. 9 may be transformed between one another at least in some implementations. For example, the carbon form 915 may be formed via an alternative pathway.

Figure 10:
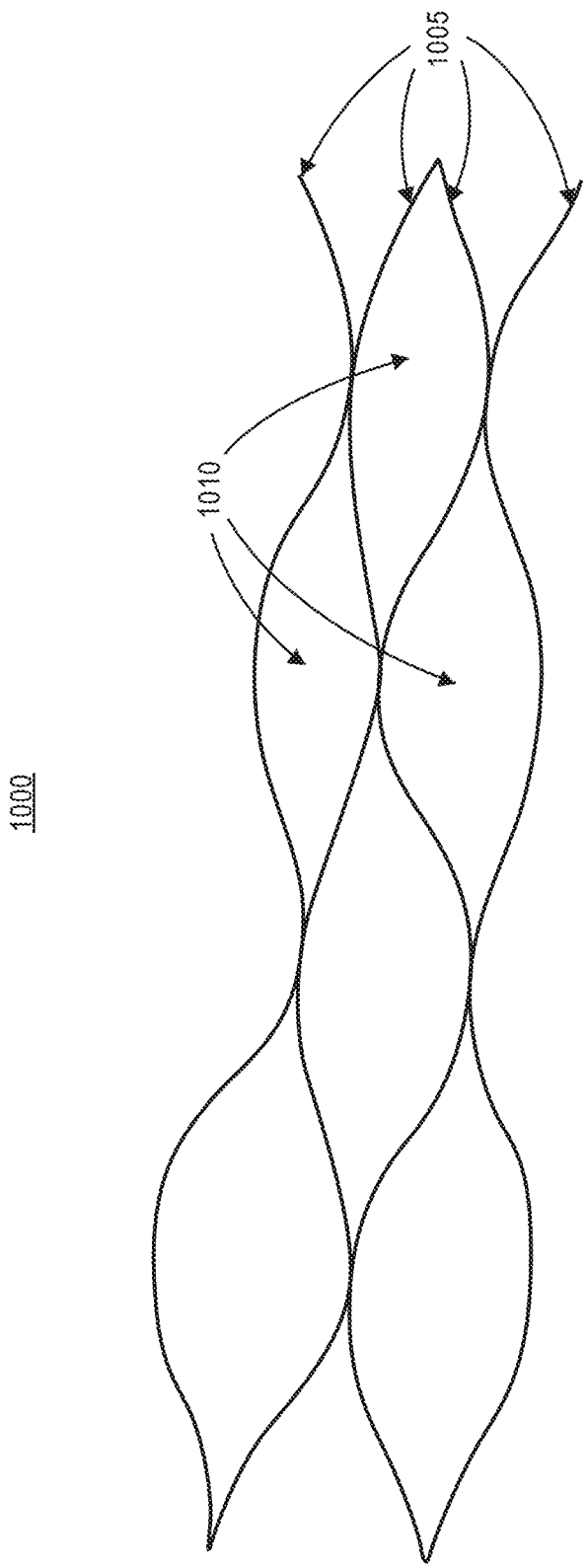
FIG. 10 illustratively depicts an example of another carbon form, per embodiments described herein.

FIG. 10 schematically illustrates an example of another carbon form 1000 comprising reduced graphite oxide. In some embodiments, the carbon form 1000 comprises an interconnected corrugated carbon-based network (ICCN) comprising a plurality of expanded and interconnected carbon layers 1005 that are interconnected and expanded apart from one another to form a plurality of pores 1010. FIG. 10 illustrates a cross-section of an exemplary ICCN that results from deoxygenating an rCBO.

Figure 11:
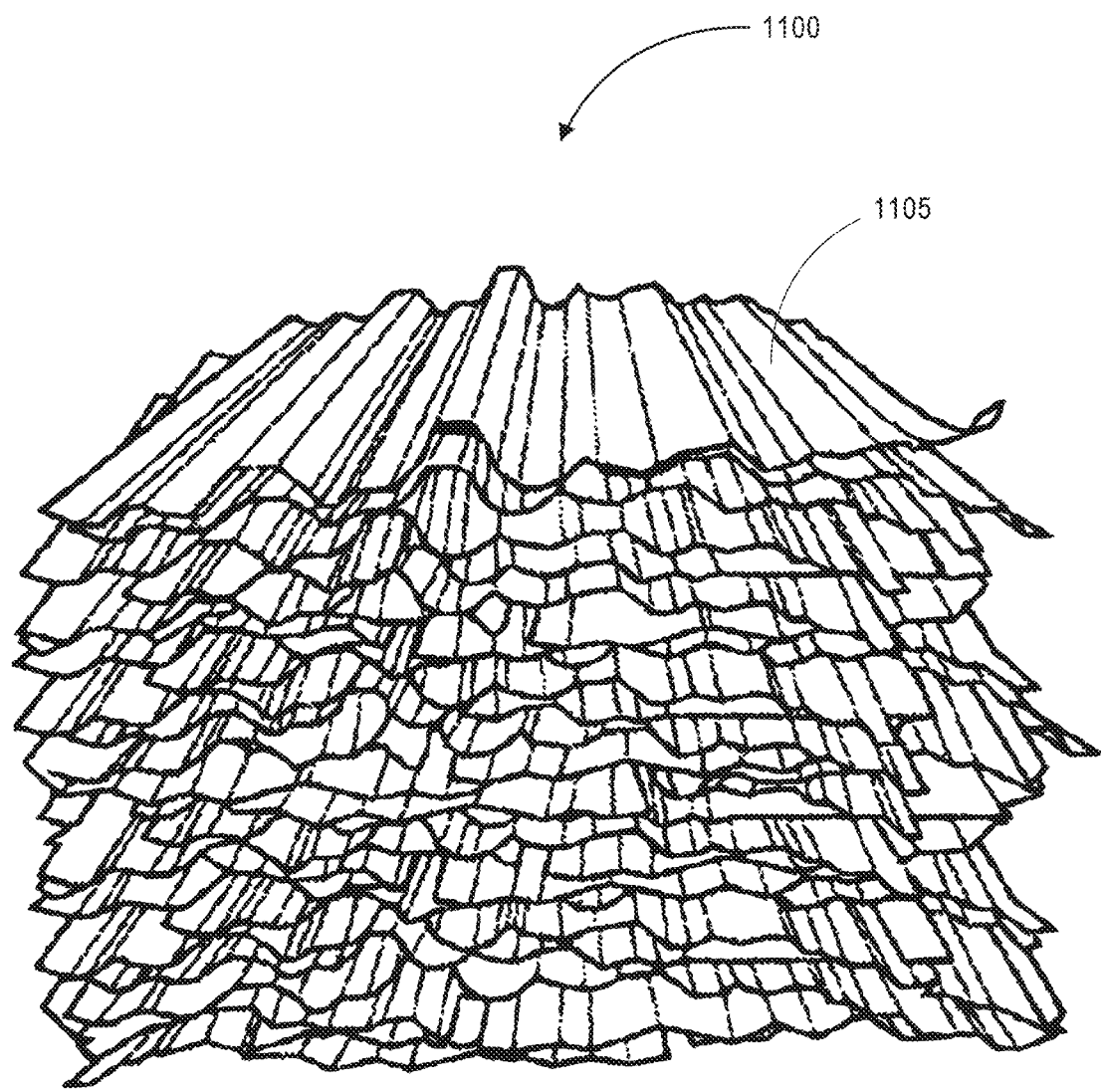
FIG. 11 illustratively depicts an example of yet another carbon form, per embodiments described herein.

FIG. 11 schematically illustrates an example of yet another carbon form 1100 of reduced graphite oxide comprising an interconnected corrugated carbon-based network (ICCN) made up of a plurality of expanded and interconnected carbon layers that include corrugated carbon layers such as a single corrugated carbon sheet 1105. In some embodiments, each of the expanded and interconnected carbon layers comprises at least one corrugated carbon sheet that is one atom thick. In another embodiment, each of the expanded and interconnected carbon layers comprise a plurality of corrugated carbon sheets that are each one atom thick. In some embodiments, a single-layer GO comprises between about 93% and 96% (e.g., by weight) of singular graphene oxide (e.g., carbon form 915 in FIG. 9). In some embodiments, a multi-layer GO comprises a given distribution (e.g., by weight) of number of layers (e.g., a distribution of carbon forms 925 with different numbers of layers). For example, a multi-layer GO may comprise greater than or equal to about 5%, 10%, 15%, 25%, 50%, 75%, 85%, 90%, or 95% (e.g., by weight) of a carbon form 925 with a given number of layers (e.g., 3 or 4). In other example, the multi-layer GO comprises a carbon form 925 by weight of between 5% and 25%, 25% and 50%, 50% and 75%, and 75% and 95% with a given number of layers. In some embodiments, the multi-layer GO comprises a percentages of a carbon form 925 together with less than or equal to about 95%, 90%, 75%, 50%, 25%, 15%, 10%, or 5% (e.g., by weight) of another carbon form 925 with a different number of layers. In some embodiments, a multi-layer GO may comprise less than about 95%, 90%, 85%, 75%, 50%, 25%, 15%, 10%, or 5% (e.g., by weight) of a carbon form 925 with a given number of layers. In some embodiments, the rGO comprises substantially sp2 carbon, substantially non-sp2 carbon, or a mixture of sp2 carbon and non-sp2 carbon.

In some embodiments, the CBO and/or the rCBO materials synthesized by a method of the present disclosure exhibit a specific or minimum purity or grade. In some embodiments, the purity or grade of a CBO or an rCBO (e.g., graphite oxide) is provided in terms of post-purification ionic conductivity.

In addition, the methods provide herein allow for adjustability of the electrical conductivity, the number of layers of graphene oxide sheets, and the degree of oxidation of the CBO or the rCBO. In some embodiments, reaction conditions may be adjusted to synthesize two forms of CBO comprising single-layer graphite oxide or multi-layer graphite oxide, wherein each form exhibits unique physicochemical properties and/or performance characteristics such as conductivity or purity.

Graphite oxide may be used as a feedstock for production of graphene, an interconnected corrugated carbon-based network (ICCN), wherein each ICCN comprises a plurality of expanded and interconnected carbon layers, porous carbon sheets (PCS), or other materials derived from graphite oxide reduced forms of graphite oxide (rGO) may comprise three-dimensional (e.g., ICCN) forms of carbon, two-dimensional (e.g., porous carbon sheet) forms of carbon, or a combination thereof (e.g., a material comprising both two- and three-dimensional forms of carbon). In some embodiments, the rGO is porous.

In some embodiments, the CBO and rCBO materials produced by the methods of the present disclosure exhibit a consistent, repeatable degree of oxygen functionality, oxidation and exfoliation, which limits water absorption to allow the CBO and rCBO materials to be effectively light-scribed (e.g., laser-scribed). In some embodiments, a CBO (e.g., graphite oxide) that is not properly oxidized and exfoliated absorbs too much water, the water may absorb a substantial amount of energy to inhibit the CBO's ability to be effectively light-scribed (e.g., laser-scribed), For example, an over-oxidized graphite oxide may comprise an excessive amount and/or unsuitable types of oxygen functionality that allow an excessive amount of water to be absorbed.

In some embodiments, an ICCN is produced from light-scribing (e.g., laser-scribing) carbon-based films such as those formed of graphite oxide. In some embodiments, rGO produces a highly conductive and high surface area laser-scribed graphene (LSG) framework that is a form of ICCN. In some embodiments, forming an ICCN (e.g., a porous ICCN) comprises disposing a solution comprising CBO and a liquid onto a substrate, evaporating the liquid from the solution to form the film, and exposing the film to light. In some embodiments, the light source comprises a laser, a flash lamp, or other high intensity light sources, wherein the light has an intensity of about 5 milliwatts to about 350 milliwatts. In some embodiments, the GO produced by the method disclosed herein is not light-scribed.

In some embodiments, the ICCN comprises an expanded interconnected network of carbon layers, and exhibits a high surface area and electrical conductivity. In some embodiments, the ICCN has a surface area of greater than or equal to about 500 square meters per gram (m$^2$/g), 1000 m$^2$/g, 1400 m$^2$/g, 1500 m$^2$/g, 1750 m$^2$/g, or 2000 m$^2$/g. In some embodiments, the ICCN has a surface area of between about 100 m$^2$/g and 1500 m$^2$/g, 500 m$^2$/g and 2000 m$^2$/g, 1000 m$^2$/g and 2500 m$^2$/g, or 1500 m$^2$/g and 2000 m$^2$/g. In some embodiments, the ICCN exhibits an electrical conductivity of greater than or equal to about 1500 S/m, 1600 S/m, 1650 S/m, 1700 S/m, 1750 S/m, 1800 S/m, 1900 S/m, or 2000 S/m. In one embodiment, the ICCN exhibits an electrical conductivity of greater than about 1700 S/m and a surface area that is greater than about 1500 m$^2$/g. In another embodiment, the ICCN exhibits an electrical conductivity of about 1650 S/m and a surface area of about 1520 m$^2$/g. In some embodiments, the reduction of GO forms rGO, wherein the rGO exhibits a higher conductivity that is more suitable for light-scribing.

In some embodiments, the ICCN has a very low oxygen content of only 3.5%. In some embodiments, the oxygen content of the ICCN ranges between about 1% and 5%, 1% and 4%, 1% and 3%, 1% and 2%, 0% and 1%, 0% and 2%, 0% and 3%, 0% and 4%, 0% and 5%, 2% and 3%, 2% and 4%, 2% and 5%, 3% and 4%, 3% and 5%, or 4% and 5%. In some embodiments, an ICCN may have an oxygen content of less than or equal to about 5%, 4.5%, 4%, 3.5%, 3%, 2.5%, 2%, 1.5%, 1%, or 0.5%. In some embodiments, the oxygen contents is measured by X-ray photoelectron spectroscopy (XPS) (e.g., in atomic percent). In some embodiments, the ICCN exhibits a low oxygen content, a high surface area, and a suitable (e.g., not too high and not too low) electrical conductivity, including any combination of the aforementioned oxygen contents, surface areas, and electrical conductivities.

In some embodiments, one or more porous carbon sheets (PCS) may be formed from GO or rGO. In some embodiments, the rGO is dispersible in a variety of solutions. In some embodiments, PCS is formed by through chemical reduction in solution. In some embodiments, the PCS has an oxygen content of less than or equal to about 10%, 9%, 8%, 7%, 6%, 5%, 4.5%, 4%, 3.5%, 3%, 2.5%, 2%, 1.5%, 1%, or 0.5%. In some embodiments, the PCS has a pore size of less than or equal to about 10 nanometers (nm), 9 nm, 8 nm, 7 nm, 6 nm, 5 nm, 4 nm, 3 nm, 2 nm, or 1 nm. In some embodiments, the PCS has a pore size of greater than or equal to about 1 nm. In some embodiments, the PCS has a pore size of between about 1 nm and 2 nm, 1 nm and 3 nm, 1 nm and 4 nm, 1 nm and 5 nm, 1 nm and 6 nm, 1 nm and 7 nm, 1 nm and 8 nm, 1 nm and 9 nm, 1 nm and 10 nm, 2 nm and 3 nm, 2 nm and 4 nm, 2 nm and 5 nm, 2 nm and 6 nm, 2 nm and 7 nm, 2 nm and 8 nm, 2 nm and 9 nm, 2 nm and 10 nm, 3 nm and 4 nm, 3 nm and 5 nm, 3 nm and 6 nm, 3 nm and 7 nm, 3 nm and 8 nm, 3 nm and 9 nm, 3 nm and 10 nm, 4 nm and 5 nm, 4 nm and 6 nm, 4 nm and 7 nm, 4 nm and 8 nm, 4 nm and 9 nm, 4 nm and 10 nm, 4 nm and 5 nm, 4 nm and 6 nm, 4 nm and 7 nm, 4 nm and 8 nm, 4 nm and 9 nm, 5 nm and 10 nm, 6 nm and 7 nm, 6 nm and 8 nm, 6 nm and 9 nm, 6 nm and 10 nm, 7 nm and 8 nm, 7 nm and 9 nm, 7 nm and 10 nm, 8 nm and 9 nm, 8 nm and 10 nm, or 9 nm and 10 nm. In some embodiments, the PCS has a pore size between about 1 nm and 4 nm, or 1 nm and 10 nm. The PCS may have one or more pore sizes (e.g., the PCS may have a distribution of such pore sizes).

In some embodiments, the GO may not need to be reduced, wherein the capacitance and/or conductivity of the unreduced GO may be substantially the same as that of the rGO (e.g., ICCN) because in some instances only the edges of the graphite are oxidized while the internal material maintains a large portion of the conductive properties of graphene (e.g., see carbon form 925 in FIG. 9). In some embodiments, GO and rGO produced by the methods herein may exhibit a similar degree of oxidation when oxidized (e.g., from the carbon form 905) to the carbon form 925. In some embodiments, the GO's properties are substantially the same as or similar to rGO produced from one or more of the oxidized carbon forms in FIG. 9 (e.g., substantially the same as or similar to rGO produced from the carbon form 925). In other embodiments, the conductivity of the GO or the rGO is between 0.1 S/m and 0.5 S/m, 0.5 S/m and 1 S/m, 1 S/m and 10 S/m, 10 S/m and 100 S/m, 100 S/m and 500 S/m, 500 S/m and 1000 S/m, 1000 S/m and 1700 S/m.

In some embodiments, further oxidation of GO alters its properties, wherein for example, further oxidizing the carbon form 925 to the carbon form 915, forms a product that is dissimilar from an rGO. For example, a device per FIG. 7A comprising a GO oxidized to the carbon form 925 (e.g., comprising a few layer graphene oxide having 3 to 5 carbon sheets or layers 960) may have substantially the same performance as the device in FIG. 7A. However, for example, the same device may or may not have substantially the same performance as the device in FIG. 7A when further oxidized to the carbon form 915.

In some embodiments, a double-layer device comprising at least one electrode comprising an unreduced or a reduced GO formed by the method provided herein has a capacitance (e.g., a peak capacitance) of greater than or equal to about 1 mF/cm$^2$, 2 mF/cm$^2$, 3 mF/cm$^2$, 4 mF/cm$^2$, 5 mF/cm$^2$, 6 mF/cm$^2$, 7 mF/cm$^2$, 8 mF/cm$^2$, 9 mF/cm$^2$, 10 mF/cm$^2$, 15 mF/cm$^2$, 20 mF/cm$^2$, 25 mF/cm$^2$, 30 mF/cm$^2$, 40 mF/cm$^2$, 50 mF/cm$^2$, 60 mF/cm$^2$, 70 mF/cm$^2$, 80 mF/cm$^2$, 90 mF/cm$^2$, 100 mF/cm$^2$, 110 mF/cm$^2$, 120 mF/cm$^2$, 130 mF/cm$^2$, 140 mF/cm$^2$, 150 mF/cm$^2$, 160 mF/cm$^2$, 170 mF/cm$^2$, 180 mF/cm$^2$, 190 mF/cm$^2$, 200 mF/cm$^2$, 210 mF/cm$^2$, 220 mF/cm$^2$, 230 mF/cm$^2$, 240 mF/cm$^2$, 250 mF/cm$^2$, 260 mF/cm$^2$, 270 mF/cm$^2$, 280 mF/cm$^2$, 290 mF/cm$^2$, 300 mF/cm$^2$, 310 mF/cm$^2$, 320 mF/cm$^2$, 330 mF/cm$^2$, 340 mF/cm$^2$, 350 mF/cm$^2$, 360 mF/cm$^2$, 370 mF/cm$^2$, 380 mF/cm$^2$, 390 mF/cm$^2$, 400 mF/cm$^2$, 410 mF/cm$^2$, 420 mF/cm$^2$, 430 mF/cm$^2$, 440 mF/cm$^2$, 450 mF/cm$^2$, 460 mF/cm$^2$, 470 mF/cm$^2$, 480 mF/cm$^2$, 490 mF/cm$^2$, 500 mF/cm$^2$, 550 mF/cm$^2$, 600 mF/cm$^2$, 650 mF/cm$^2$, 700 mF/cm$^2$, 750 mF/cm$^2$, 800 mF/cm$^2$, or more. In some embodiments, a double-layer device comprising at least one electrode comprising the unreduced or reduced GO formed by the method provided herein has a capacitance of greater than or equal to between 1 mF/cm$^2$ and 10 mF/cm$^2$, 10 mF/cm$^2$ and 100 mF/cm$^2$, 100 mF/cm$^2$ and 500 mF/cm$^2$, and 500 mF/cm$^2$ and 1000 mF/cm$^2$. In some embodiments, a double-layer device comprising at least one electrode comprising the unreduced or reduced GO formed by the method provided herein has a conductivity of greater than or equal to about 0.1 siemens per meter (S/m), 0.5 S/m, 1 S/m, 10 S/m, 15 S/m, 25 S/m, 50 S/m, 100 S/m, 200 S/m, 300 S/m, 400 S/m, 500 S/m, 600 S/m, 700 S/m, 800 S/m, 900 S/m, 1,000 S/m, 1,100 S/m, 1,200 S/m, 1,300 S/m, 1,400 S/m, 1,500 S/m, 1,600 S/m, or 1,700 S/m. As such, the GO may therefore be used in a device such as, for example, a double-layer device, both before and after (e.g., see FIG. 7A) reduction. The performance of the two materials in, for example, a double-layer device may be substantially the same.

In some embodiments, the conductivity, the surface area, or the C:O ratio, of the CBO or rCBO is measured by methylene blue absorption.

Devices Comprising Carbon-Based Oxides and Reduced Carbon-Based Oxides

In some embodiments, the methods described herein synthesize CBO and rCBO materials capable of forming high performance double-layer capacitors, the areal capacitance of which is at least about 228 mF/cm$^2$, wherein current methods may only be capable of forming double-layer capacitors, the areal capacitance of which is about 4.04 mF/cm$^2$. As such, the methods described herein are capable of synthesizing CBO and rCBO materials which are capable of forming double-layer capacitors with a greater capacitance (e.g., at least about 2, 5, 10, 15, 20, 25, 30, 35, 40, 45, 50, 55, or 60 times greater) than that formed by the CBO or rCBO materials formed by current methods.

Figure 6:
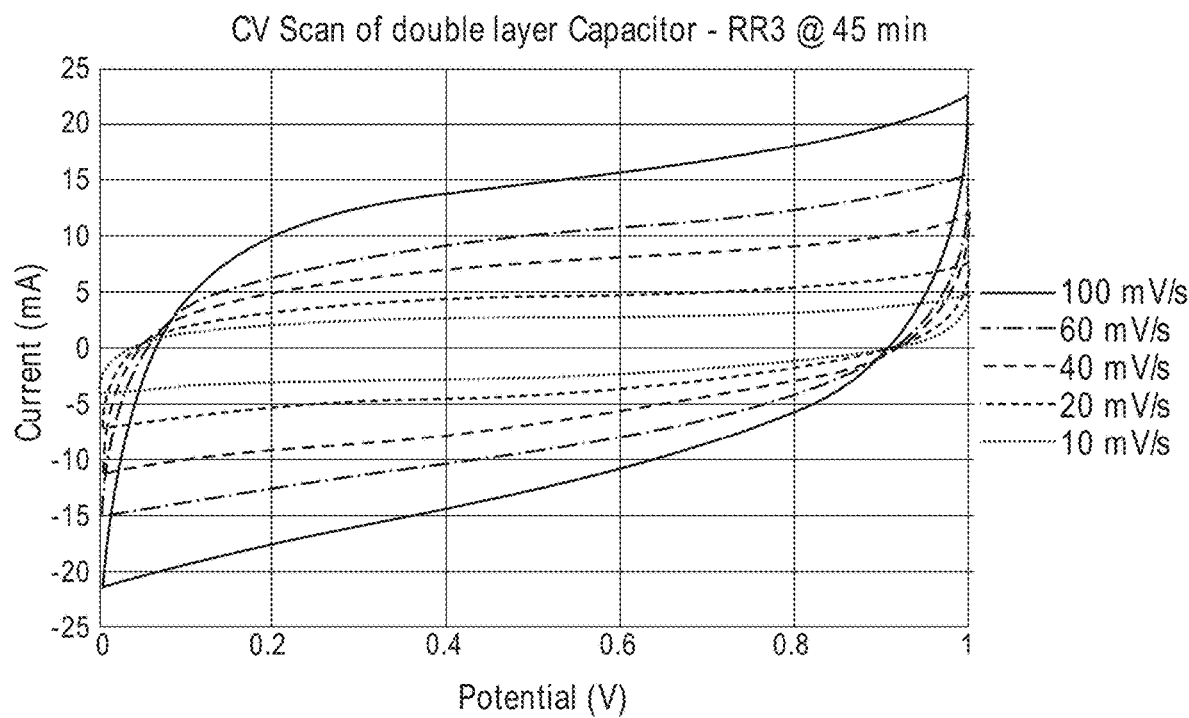
FIG. 6 is a cyclic voltammetry (CV) scan of an exemplary double-layer capacitor constructed from a CBO material with a 45 min stir time, at scan rates of 10 mV/s, 20 mV/s, 40 mV/s, 60 mV/s, and 100 mV/s, per embodiments described herein.

The performance characteristics of an exemplary double-layer device (double-layer capacitor) was constructed from the CBO formed by the method provided herein (RR 3 at 45 min) are shown in FIG. 6 and TABLE 1.

TABLE 1

| Scan Rate (mV/s) | Capacitance (mF) | Specific Capacitance (F/g) |
|---|---|---|
| 10 | 229 | 265 |
| 20 | 192 | 223 |
| 40 | 159 | 185 |
| 60 | 140 | 164 |
| 100 | 118 | 137 |

Figure 7A:
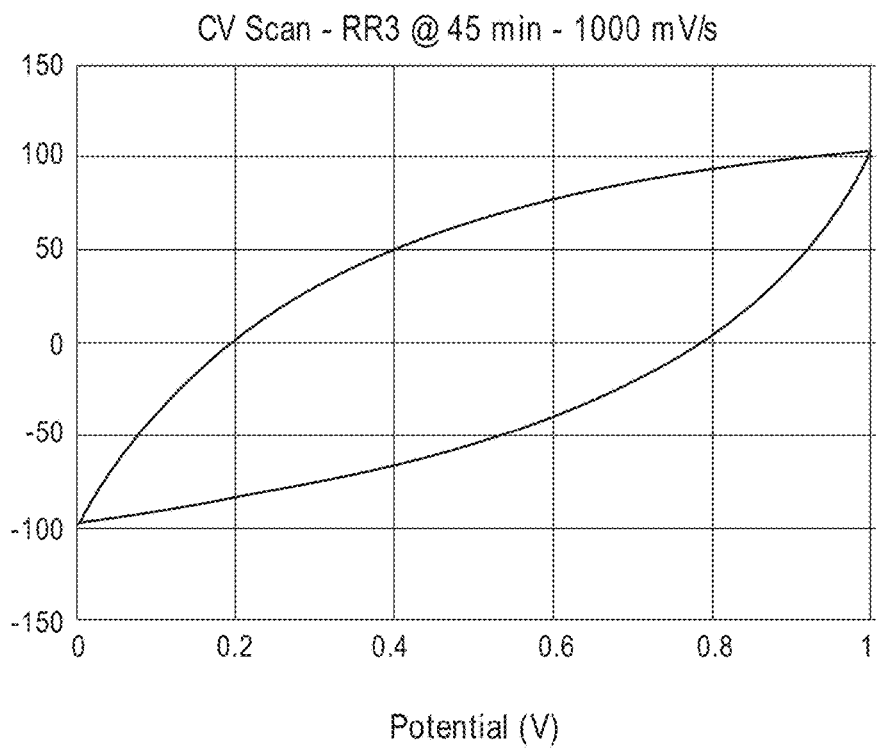
FIG. 7A is a cyclic voltammetry (CV) scan of an exemplary double-layer capacitor with electrodes comprising light-scribed CBO materials, at a scan rate of 1,000 mV/s, per embodiments described herein.
Figure 7B:
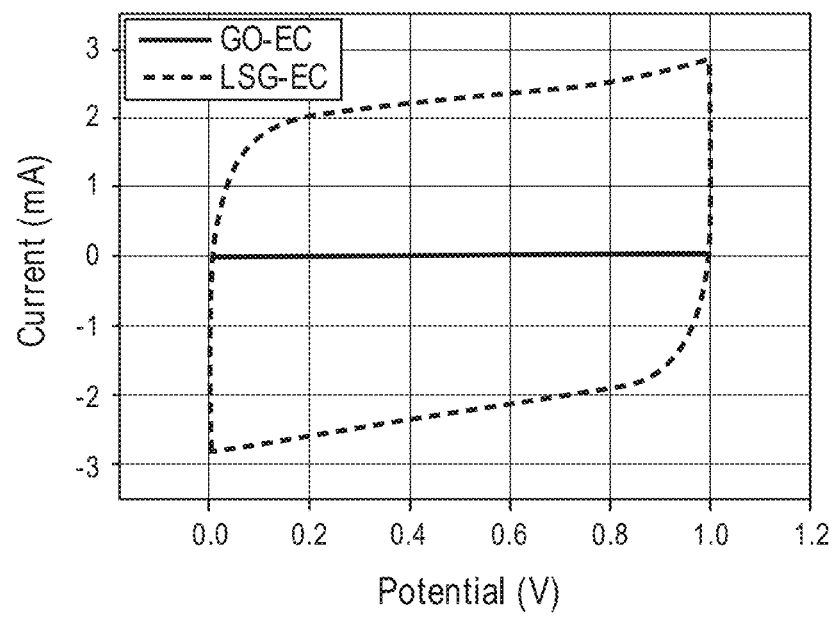
FIG. 7B is a cyclic voltammetry (CV) scan of an exemplary double-layer capacitor with electrodes comprising light-scribed CBO materials, and non-light-scribed CBO materials, at a scan rate of 1,000 mV/s, per embodiments described herein.

FIG. 7A shows an exemplary cyclic voltammetry (CV) scan at a scan rate of 1,000 mV/s of a double-layer capacitor with electrodes comprising light-scribed rGO (ICCN) produced by the methods provided herein. FIG. 7B shows an exemplary cyclic voltammetry (CV) scan at a scan rate of 1,000 mV/s of a double-layer capacitor with electrodes comprising light-scribed GO materials, and non-light-scribed GO materials. As a CV scan of the exemplary device comprising electrodes formed of an unreduced GO synthesized by the methods disclosed herein (not shown) is essentially equivalent to the CV scan of the light-scribed rGO (ICCN) produced by the methods provided, per FIG. 7A, the effects of light-scribing may be insubstantial. In contrast, light-scribing alters the performance characteristics of the exemplary GO materials, per FIG. 7B. In some embodiments, the light-scribed rGO (ICCN) produced by the methods provided herein exhibit a capacitance at 1000 mV/s that is at least about 35 times greater than a capacitance of the light-scribed GO materials, and non-light-scribed GO materials.

Figure 12:
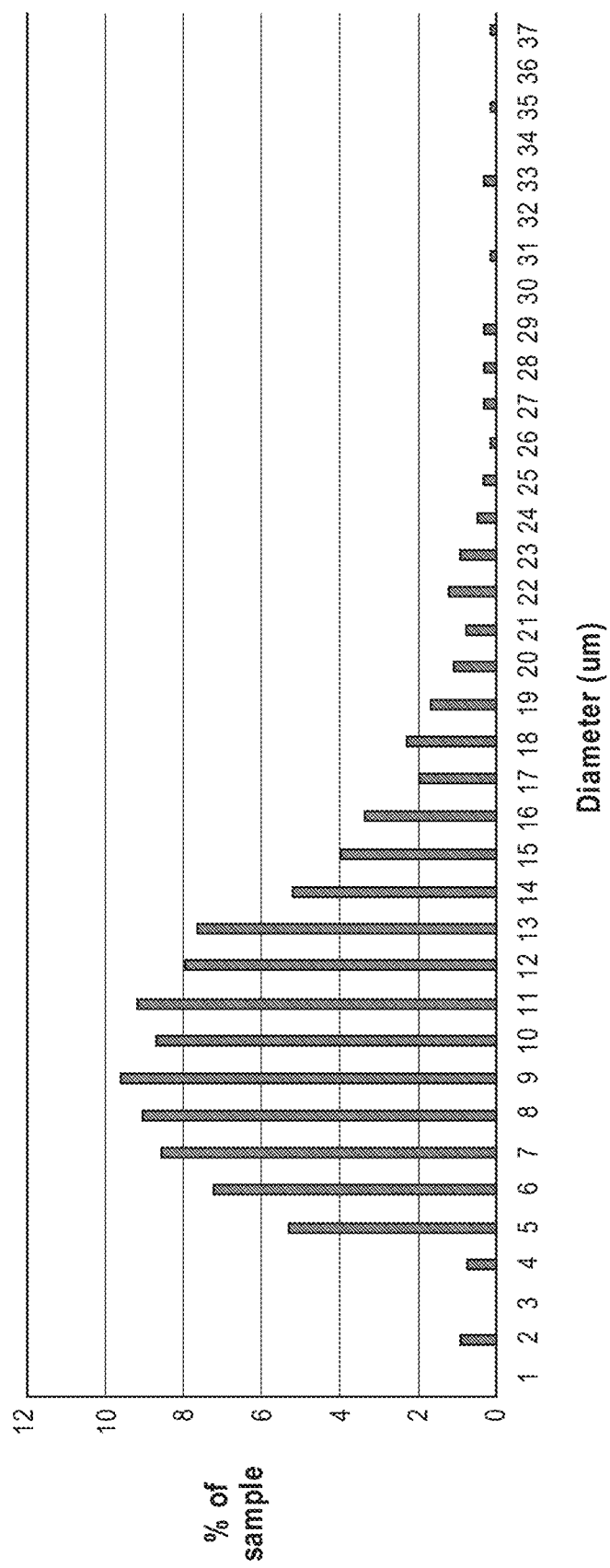
FIG. 12 is a particle distribution chart of an exemplary CBO, per embodiments described herein.
Figure 13:
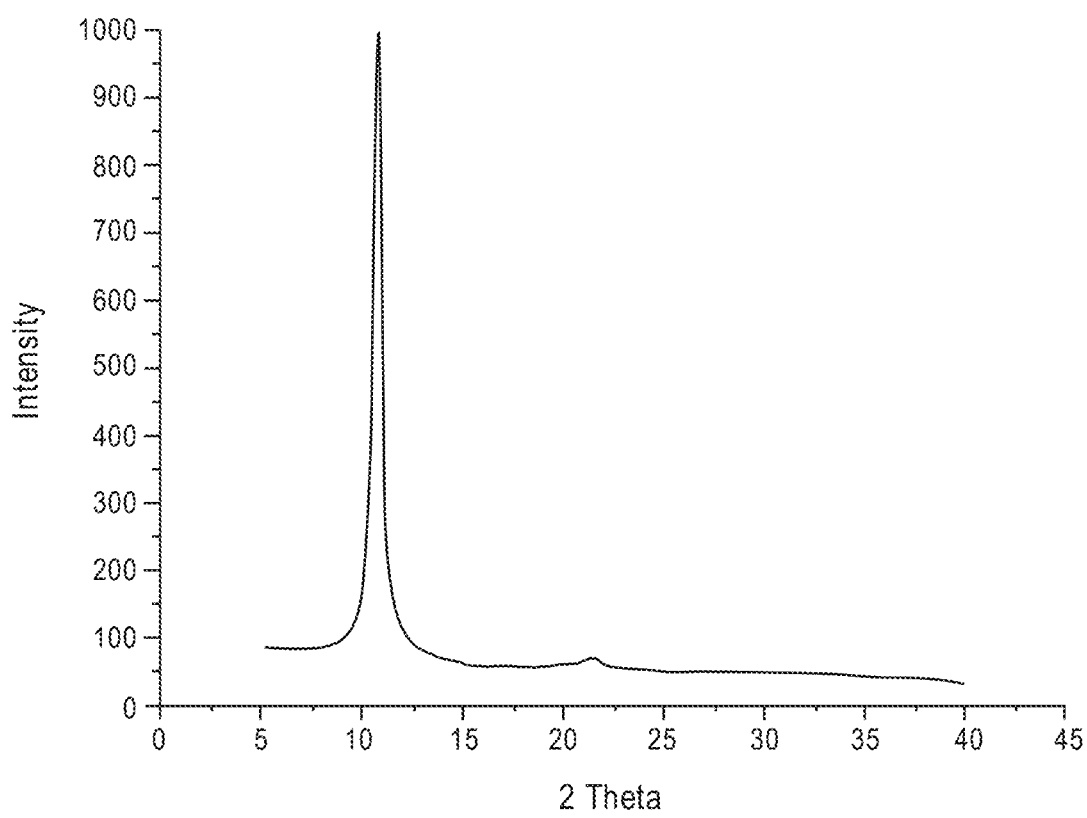
FIG. 13 is an X-Ray Diffraction (XRD) graph of an exemplary CBO, per embodiments described herein.
Figure 14:
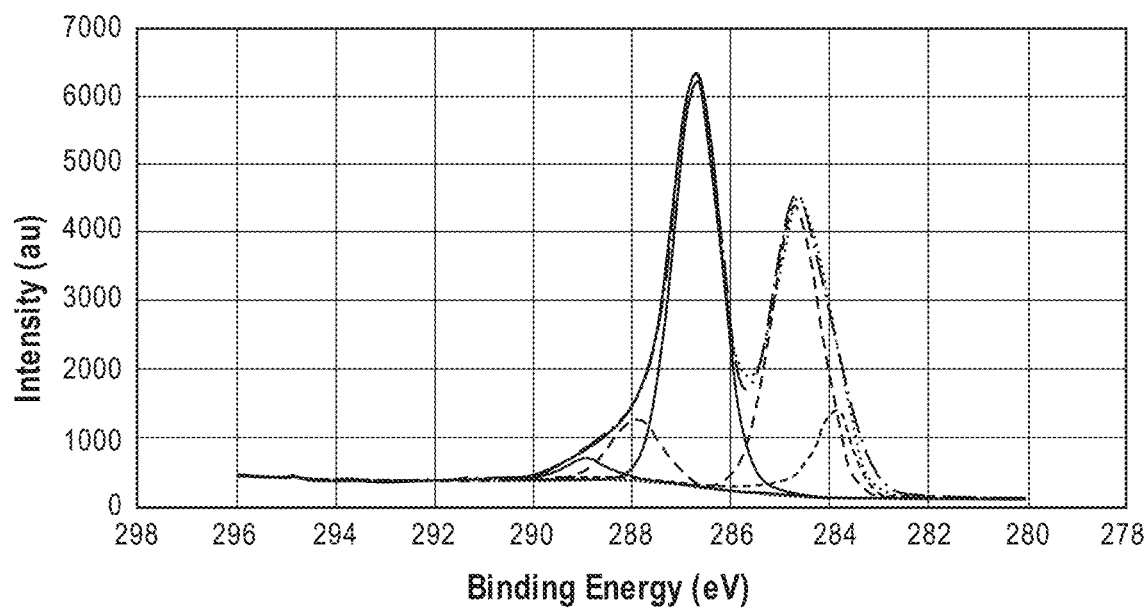
FIG. 14 is an X-ray Photoelectron Spectroscopy (XPS) graph of an exemplary CBO, per embodiments described herein.
Figure 15:
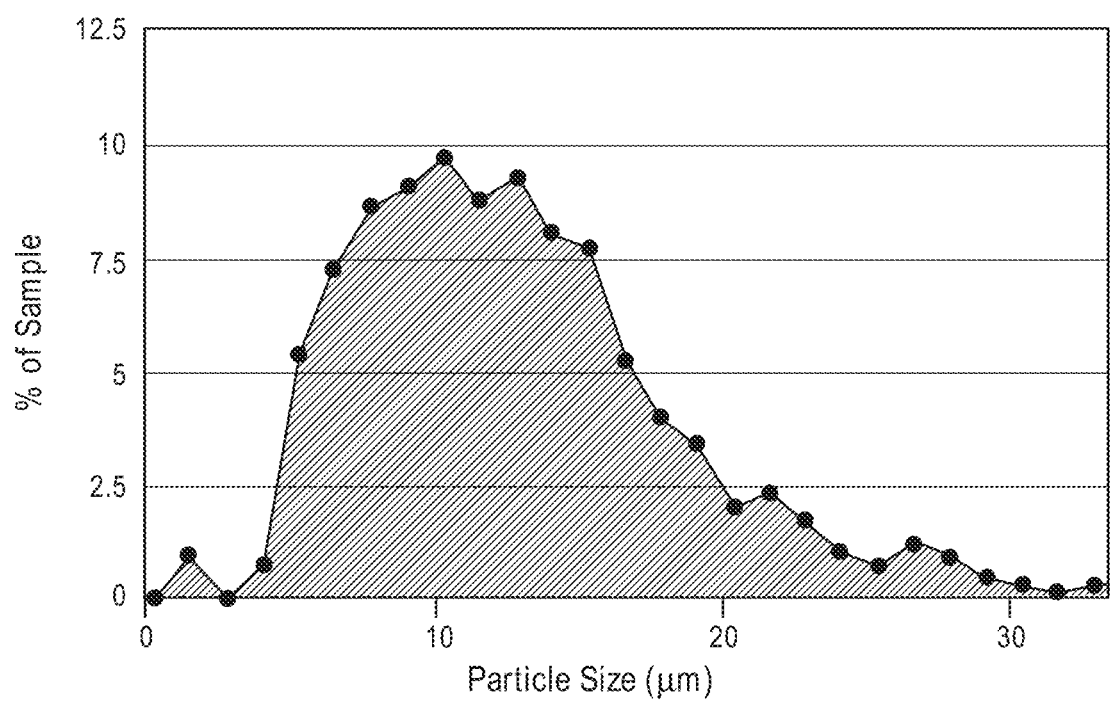
FIG. 15 is a particle size distribution chart of an exemplary rCBO, per embodiments described herein.
Figure 16:
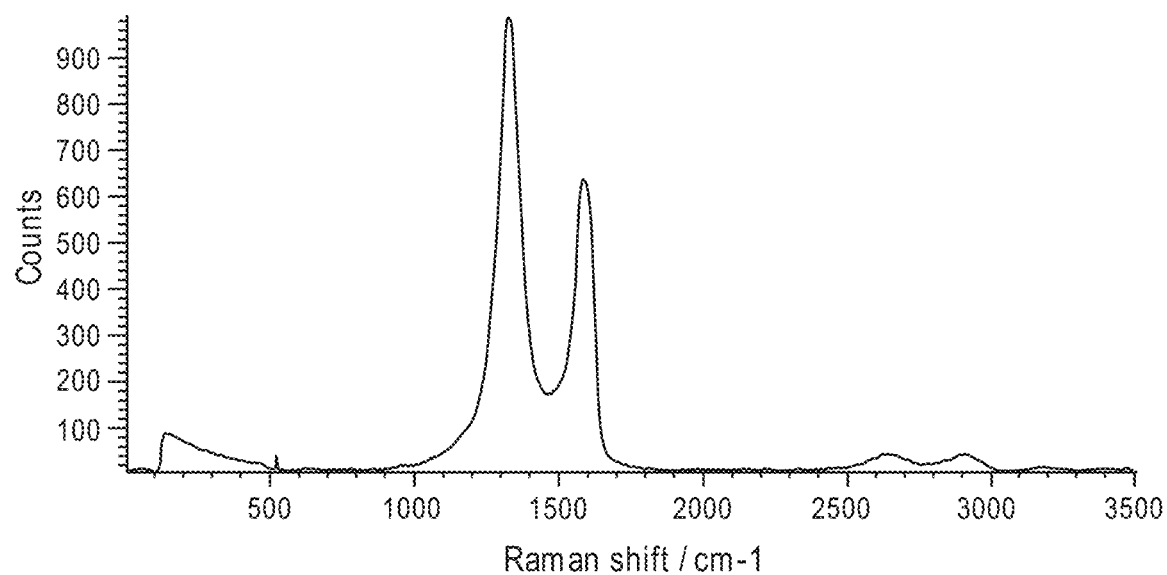
FIG. 16 is a Raman spectra of an exemplary rCBO, per embodiments described herein.

FIG. 12 is a particle distribution chart of an exemplary CBO, per embodiments described herein. FIG. 13 is an X-Ray Diffraction (XRD) graph of an exemplary CBO, per embodiments described herein. FIG. 14 is an X-ray Photoelectron Spectroscopy (XPS) graph of an exemplary CBO, per embodiments described herein. FIG. 15 is a particle size distribution chart of an exemplary rCBO, per embodiments described herein. FIG. 16 is a Raman spectra of an exemplary rCBO, per embodiments described herein.

Figure 17:
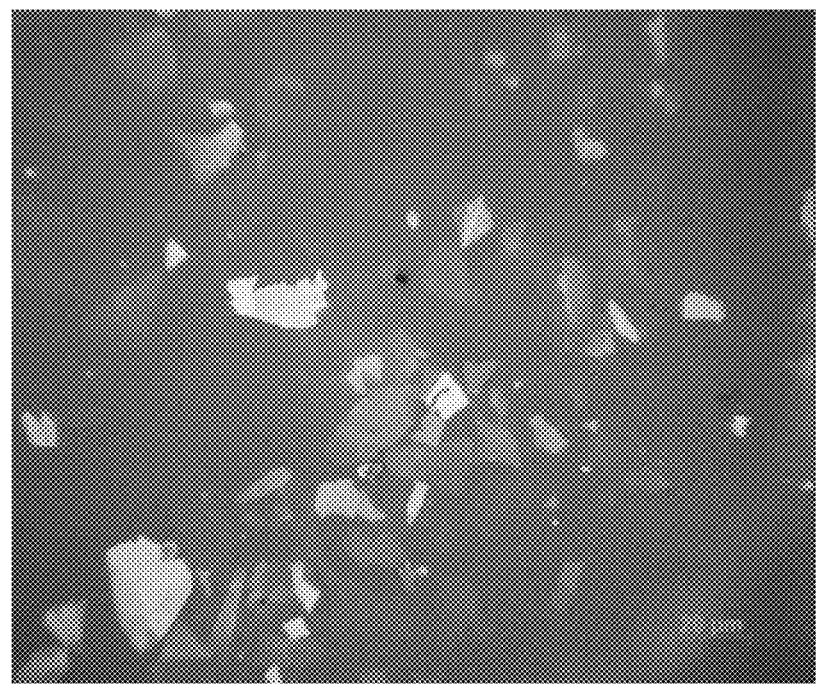
FIG. 17 is optical microscope image of sheets of an exemplary CBO on a silicon wafer, coated with $SiO_2$, per embodiments described herein.
Figure 18A:
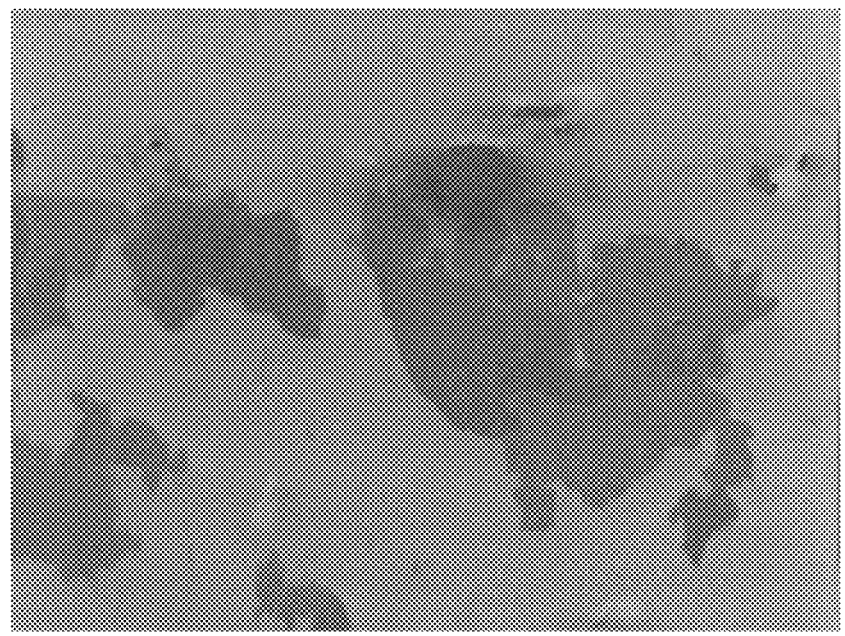
FIG. 18A is a low magnification scanning electron microscope (SEM) image of an exemplary CBO on a silicon wafer, coated with $SiO_2$, per embodiments described herein.
Figure 18B:
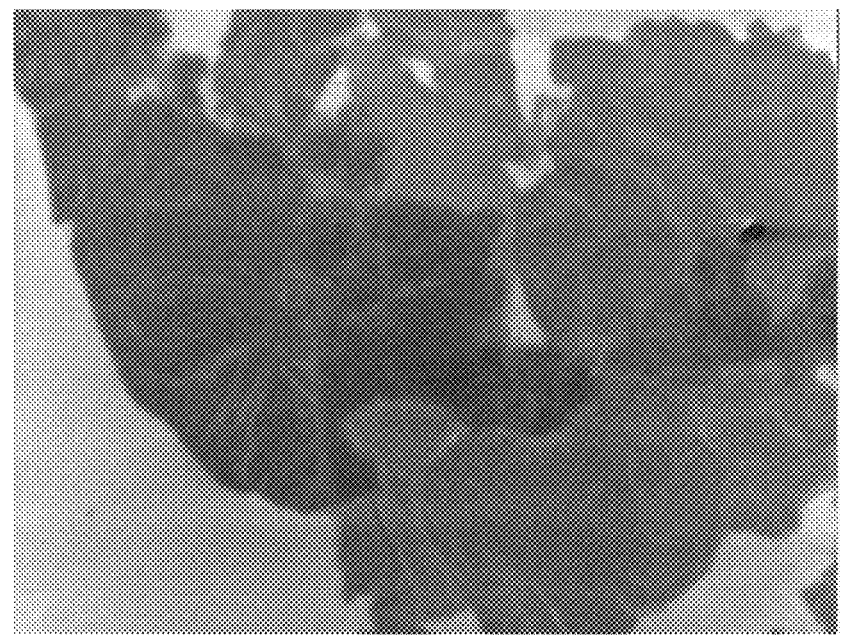
FIG. 18B is a high magnification scanning electron microscope (SEM) image of an exemplary CBO on a silicon wafer, coated with $SiO_2$, per embodiments described herein.

In some embodiments, exemplary sheets of GO material, per FIG. 17, are formed by drop-casting the GO material onto a silicon wafer, drying the GO material and the wafer for a period of time of about 12 hours, and coating the dried GO material with a thin layer of silicon dioxide (SiO$_2$). The exemplary optical microscope images in FIG. 17 of the device formed thereby display the lateral size distribution of the GO sheets. Low and high magnification scanning electron microscope (SEM) image of an exemplary GO material on a silicon wafer, coated with SiO$_2$ are show in FIGS. 18A and 18B, respectively.

Applications for Carbon-Based Oxide or Reduced Carbon-Based Oxide Materials

The CBO and rCBO materials described in the present disclosure may be used in a variety of applications including but not limited to: supercapacitors, batteries, energy storage device, catalysts, structural materials, water filtration, batteries, drug delivery, hydrogen storage, conductive inks, electronics, cars, aerospace technologies, inkjet printing, screen printing, printed circuit boards, radio frequency identification chips, smart fabrics, conductive coatings, gravure printing, flexographic printing, anti-static coatings, electrodes, electromagnetic interference shielding, printed transistors, memory, sensors, large area heaters, thermoelectric materials, lubricant, and thermal management systems.

In some embodiments, CBO and rCBO materials form reinforcements for polymers and oxides. In some embodiments, fibers formed from CBO and rCBO materials exhibit strong electrical and mechanical properties and serve as an alternative for carbon fibers currently used in car and aerospace industries. CBO and rCBO materials may be used in the fabrication of highly selective membranes that enable high flux rates and reduced energy consumption in filtering processes. CBO and rCBO electrodes may provide energy storage devices with high energy capacities. In some embodiments, CBO and rCBO materials exhibit may form supercapacitors with very high surface areas and capacitances. The water solubility and biocompatibility of some CBO and rCBO materials may form drug carrying devices. Finally, CBO and rCBO materials may be capable of efficiently storing hydrogen effectively.

Terms and Definitions

Unless otherwise defined, all technical terms used herein have the same meaning as commonly understood by one of ordinary skill in the art. As used in this specification and the appended claims, the singular forms "a," "an," and "the" include plural references unless the context clearly dictates otherwise. Any reference to "or" herein is intended to encompass "and/or" unless otherwise stated.

As used herein, and unless otherwise defined, the term "about" refers to a range of values within plus and/or minus 10% of the specified value.

As used herein, and unless otherwise defined, the term "graphite oxide" and "graphene oxide" are used interchangeably. In some instances, graphite oxide and graphene oxide are collectively referred to herein as "GO." For the purpose of this disclosure, the terms "reduced graphite oxide" and "reduced graphene oxide" are used interchangeably. In some instances, reduced graphite oxide and reduced graphene oxide are collectively referred to herein as "rGO."

As used herein, and unless otherwise defined, the term "CBO" and "rCBO" refer to a carbon-based oxide and a reduced carbon-based oxide, respectively.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method for producing a carbon-based oxide material comprising:
   forming a first solution comprising graphite and an acid;
   cooling the first solution to a temperature that is at most about 30° C.;
   adding a first oxidizing agent to the first solution to form a second solution;
   quenching the second solution to a temperature that is at most about 75° C. to form a carbon-based oxide material, and purifying the carbon-based oxide material, wherein the carbon-based oxide material is filtered until a pH from about 5 to about 7 is achieved, wherein reactions from the first oxidizing agent are neutralized;
   forming a third solution comprising the carbon-based oxide material and a second oxidizing agent; and
   heating the third solution to a temperature of at least about 45° C.

2. The method of claim 1, wherein the acid comprises perchloric acid, hydroiodic acid, hydrobromic acid, hydrochloric acid, sulfuric acid, p-toluenesulfonic acid, methanesulfonic acid, or any combination thereof.

3. The method of claim 1, wherein a mass of the acid is greater than a mass of the graphite by a factor of about 30 to about 180.

4. The method of claim 1, wherein the first solution comprising the graphite and the acid is cooled to a temperature from about −20° C. to about 30° C.

5. The method of claim 1, wherein the first oxidizing agent comprises oxygen, ozone, hydrogen peroxide, fluorite dioxide, lithium peroxide, barium peroxide, fluorine, chlorine, nitric acid, nitrate compounds, sulfuric acid, peroxydisulfuric acid, peroxymonosulfuric acid, chlorite, chlorate, perchlorate, halogen compounds, hypochlorite, hypohalite compounds, household bleach, hexavalent chromium compounds, chromic acids, dichromic acids, chromium trioxide, pyridinium chlorochromate, chromate compounds, dichromate compounds, permanganate compounds, potassium permanganate, sodium perborate, nitrous oxide, potassium nitrate, sodium bismuthate, or any combination thereof, and wherein a mass of the first oxidizing agent is greater than a mass of the graphite by a factor of about 1.5 to about 12.

6. The method of claim 1, wherein the first oxidizing agent is added to the first solution comprising the graphite and the acid over a period of time of about 15 minutes to about 180 minutes.

7. The method of claim 1, further comprising allowing the second solution comprising the first oxidizing agent to react at a temperature from about 10° C. to about 70° C., prior to quenching said second solution.

8. The method of claim 1, wherein quenching the second solution occurs via an ice bath, a water bath, one or more cooling coils, ice, water, addition of a third oxidizing agent to the second solution, or any combination thereof, and wherein a temperature of the second solution after quenching is from about 25° C. to about 75° C.

9. The method of claim 8, wherein the third oxidizing agent comprises oxygen, ozone, hydrogen peroxide, fluorite dioxide, lithium peroxide, barium peroxide, fluorine, chlorine, nitric acid, nitrate compounds, sulfuric acid, peroxydisulfuric acid, peroxymonosulfuric acid, chlorite, chlorate, perchlorate, halogen compounds, hypochlorite, hypohalite compounds, household bleach, hexavalent chromium compounds, chromic acids, dichromic acids, chromium trioxide, pyridinium chlorochromate, chromate compounds, dichromate compounds, permanganate compounds, potassium permanganate, sodium perborate, nitrous oxide, potassium nitrate, sodium bismuthate, or any combination thereof, and wherein a mass of the second oxidizing agent is greater than a mass of the graphite by a factor of about 1.5 to about 6.

10. The method of claim 1, wherein quenching the second solution occurs over a period of time of about 30 minutes to about 120 minutes.

11. The method of claim 1, further comprising agitating at least one of 1) the first solution comprising the graphite and acid, and 2) the second solution comprising the graphite, acid and first oxidizing agent, wherein said agitating occurs for a period of time of about 45 minutes to about 360 minutes.

12. The method of claim 1, further comprising allowing the second solution to react for a period of time of about 15 minutes to about 120 minutes after the second solution is quenched, wherein the second solution during reaction has a temperature that is about 15° C. to about 75° C.

13. The method of claim 1, wherein purifying the second solution comprises filtering the carbon-based oxide material through a first filter and concentrating the carbon-based oxide material.

14. The method of claim 1, wherein heating the third solution and adding the second oxidizing agent occur simultaneously.

15. The method of claim 1, wherein the third solution is heated from about 45° C. to about 180° C., and wherein heating the third solution occurs over a period of time of about 30 minutes to about 120 minutes.

16. The method of claim 1, wherein the second oxidizing agent comprises oxygen, ozone, hydrogen peroxide, fluorite dioxide, lithium peroxide, barium peroxide, fluorine, chlorine, nitric acid, nitrate compounds, sulfuric acid, peroxydisulfuric acid, peroxymonosulfuric acid, chlorite, chlorate, perchlorate, halogen compounds, hypochlorite, hypohalite compounds, household bleach, hexavalent chromium compounds, chromic acids, dichromic acids, chromium trioxide, pyridinium chlorochromate, chromate compounds, dichromate compounds, permanganate compounds, potassium permanganate, sodium perborate, nitrous oxide, potassium nitrate, sodium bismuthate, or any combination thereof.

17. The method of claim 16, wherein the second oxidizing agent is hydrogen peroxide.

18. The method of claim 1, capable of producing a throughput of carbon-based oxide material of about 0.1 pound/day to about 50 pounds/day.

19. The method of claim 1, further comprising adding a reducing agent to the third solution to form a reduced carbon-based oxide material.

20. The method of claim 19, wherein the reducing agent comprises sodium ascorbate, calcium ascorbate, potassium ascorbate, magnesium ascorbate, or any combination thereof.

21. The method of claim 19, wherein the reducing agent is added to the third solution over a period of time of about 10 minutes to about 60 minutes.

22. The method of claim 19, further comprising allowing the third solution and the reducing agent to react for a period of time of about 45 minutes to about 180 minutes.

23. The method of claim 19, further comprising agitating the third solution for a period of time of about 45 minutes to about 360 minutes.

24. The method of claim 19, further comprising purifying the reduced carbon-based oxide material, wherein purifying the reduced carbon-based oxide material comprises filtering with a second filter, flushing the third solution, or any combination thereof.

\* \* \* \* \*